(12) United States Patent
Romesberg et al.

(10) Patent No.: US 7,455,840 B2
(45) Date of Patent: Nov. 25, 2008

(54) COMPOSITIONS AND METHODS TO REDUCE MUTAGENESIS

(75) Inventors: Floyd Romesberg, La Jolla, CA (US); Nathaniel E. David, San Francisco, CA (US); Ryan Cirz, San Diego, CA (US)

(73) Assignees: The Scripps Research Institute, La Jolla, CA (US); Achaogen, Inc., San Francisco, CA (US)

(*) Notice: Subject to any disclaimer, the term of this patent is extended or adjusted under 35 U.S.C. 154(b) by 267 days.

(21) Appl. No.: 10/994,215

(22) Filed: Nov. 19, 2004

(65) Prior Publication Data

US 2006/0111302 A1    May 25, 2006

Related U.S. Application Data

(60) Provisional application No. 60/608,949, filed on Nov. 19, 2003.

(51) Int. Cl.
*A61K 31/47* (2006.01)
*A61K 38/02* (2006.01)
*A61K 39/40* (2006.01)

(52) U.S. Cl. .............. 424/164.1; 424/150.1; 514/2; 514/18; 514/19; 514/312

(58) Field of Classification Search ............ None
See application file for complete search history.

(56) References Cited

U.S. PATENT DOCUMENTS

| | | | |
|---|---|---|---|
| 5,945,285 A | 8/1999 | Mekalanos et al. | |
| 6,054,431 A | 4/2000 | Horwitz et al. | |
| 6,410,514 B1 | 6/2002 | Isaacs et al. | |
| 6,503,881 B2* | 1/2003 | Krieger et al. ............. | 514/2 |
| 2002/0022718 A1 | 2/2002 | Forsyth et al. | |
| 2002/0045592 A1 | 4/2002 | Zyskind et al. | |
| 2004/0029129 A1 | 2/2004 | Wang et al. | |
| 2004/0147006 A1 | 7/2004 | Bullock | |
| 2004/0185530 A1 | 9/2004 | Janjic et al. | |
| 2005/0108047 A1* | 5/2005 | David ........................ | 705/2 |

FOREIGN PATENT DOCUMENTS

JP    2002-114704 A    *    4/2002

OTHER PUBLICATIONS

Baker, "Battling Evolution to Fight Antibiotic Resistance," The Scientist, 2005, 19, 17 printed from http://www.the-scientist.com/2005/10/10/17/1, pp. 1-7.*
Harbottle et al., "Genetics of antimicrobial resistance," Anim. Biotechnol., 2006, 17, 11, abstract only.*

(Continued)

*Primary Examiner*—Jeffrey E Russel
(74) *Attorney, Agent, or Firm*—Quine Intellectual Property Law Group, P.C.

(57) ABSTRACT

The present invention provides methods and compositions for said inhibition of drug resistance. In one embodiment, said invention provides methods and compositions for said inhibition of antibiotic resistance. The invention generally involves said administration of achaogens, agents that inhibit said mutational process, to inhibit said evolution of drug resistance. Also, described herein are compositions that are suitable for use as achaogens.

5 Claims, 18 Drawing Sheets

OTHER PUBLICATIONS

Van Bambeke, "Quinolones in 2005: an update," Clin. Microbiol. Infect., 2005, 11, 256-80.*

Corkill et al., "High prevalence of the plasmid-mediated quinolone resistance determinant qnrA in multidrug-resistant Enterobacteriaceae from blood cultures in Liverpool, UK," J. Antimicrob. Chemo., 2005, 56, 115-7.*

Ginalski et al. "Practical lessons from protein structure prediction," Nuc. Ac. Res., 2005, 33, 1874.*

Cejka et al. "Short interfering RNA: tool or therapeutic?" Clin. Sci., 2006, 110, 47-58.*

Sutter et al. "Gene therapy for gastric cancer: is it promising?" World J Gastroenterol., 2006, 12, 380-7.*

Miyakawa et al. In Vitro Activity of the Antimicrobial Peptides . . . Infection And Immunity. Mar. 1996, vol. 64, No. 3, pp. 926-932.*

Yasuda et al. Inhibition of *Eschericia coli* RecA coprotease activities by DinI. The EMBO Journal. 1998, vol. 17, No. 11, pp. 3207-3216.*

Naslund et al. Inhibition of recA induction by the radioprotector 2-mercaptoethylamine. Mutation Research. 1992, vol. 282, pp. 203-207.*

Piddock et al. Correlation of Quinolone MIC and Inhibition of DNA . . . Antimicrobial Agents And Chemotherapy. Dec. 1990, vol. 34, No. 12, pp. 2331-2336.*

Miller et al. (2004) "SOS Response Induction by β-Lactams and Bacterial Defense Against Antibiotic Lethality" Science 305: 1629-1631.

Bearer, J.W., et al., "SOS Response Promotes Horizontal Dissemination of Antibiotic Resistance Genes," *Nature* (2004) 427:72-74.

Bhamre, S., et al., "An Aerobic *recA-,umuC*-Dependent Pathway of Spontaneous Base-Pair Substitution Mutagenesis in *Escherichia coli*," *Mutation Research* (2001) vol. 473:229-247.

Boshoff, H., et al., "DnaE2 Polymerase Contributes to In Vivo Survival and the Emergence of Drug Resistance in Mycobacterium Tuberculosis," *Cell* (2003) 113:183-193.

Cordell, S., et al., "Crystal Structure of the SOS Cell Division Inhibitor SulA and in Complex with FtsZ," *PNAS* (2003) 100(13): 7889-7894.

Frank, E.G., et al., "Regulation of SOS Mutagenesis by Proteolysis," *PNAS* (1996) 93: 10291-10296.

Liu, J., et al., "Antimicrobial Drug Discover Through Bacteriophage Genomics," *Nature Biotechnology*, (2004) 22(2): 185-1991.

Napolitano, R., et al., "All three SOS-inducible DNA polymerase (Pol II, Pol IV and Pol V) are involved in induced mutagenesis," *EMBO J.* (2000) 19:6259-6265.

Ramirez, B.E., et al., "Solutions Structure of DinI Provides Insight into its Mode of RecA Inactivation," *Protein Science* (2000) 9:2161-2169.

Riesentfeld, C., et al., "Adaptive Mutations Produce Resistance to Ciprofloxacin," *Antimicrobial Agents and Chemotherapy* (1997) 41(9): 2059-2060.

Roland, K.L., et al., "Reaction of LexA Repressor with Diisoprophyl Fluorophosphate," *The Journal of Biological Chemistry* (1990) 265(22): 12828-12835.

Rosenburg, S.M., "Evolving responsively: adaptive mutation," *Nat Rev Genet* (2001) 2:504-515.

Voloshin, O., et al., "A Model for the Abrogation of the SOS Response by an SOS Protein: a Negatively Charged Helix in DinI Mimics DNA in its Interaction with RecA," *Genes & Development* (2001) 15(4): 415-427.

Arunan, C. (1999) "Solid-phase synthesis of hydrophobic peptides n 1,6-hexanediol diacrylate crosslinked poly-styrene resin: comparison with Merrifield resin." *Peptide and Peptide Letters*, 6(6): 391-398.

Illenberger, S. (1998) "The endogenous and cell cycle-dependent phosphorylation of tau protein in living cells: implications for Alzheimer's disease." *Molecular Biology of the Cell*, 9: 1495-1512.

Allen and Nicas (2003) "Mechanism of action of oritavancin and related glycopeptide antibodies." *FEMS Microbiology Reviews*, 26: 511-532.

Ames et al. (1973) "An Improved Bacterial Test System for the Detection and Classification of Mutagens and Carcinogens." *Proceedings of the National Academy of Sciences*, USA, 70(3): 782-786.

Mehlotra et al. (2001) "Evloution of a unique Plasmodium falciparum chloroquine-resistance phenotype in association with pfcrt polymorphism in Papua New Guinea and South America." *Proceedings of the National Academy of Sciences*, USA, 98(22): 12689-12694.

Mehta et al. (1992) "In-Vivo Identification of Tumor Multidrug Resistance with Tritium-3-Colchicine." *Journal of Nucleic Medicine*, 33: 1373-1377.

* cited by examiner

SLAM Assay
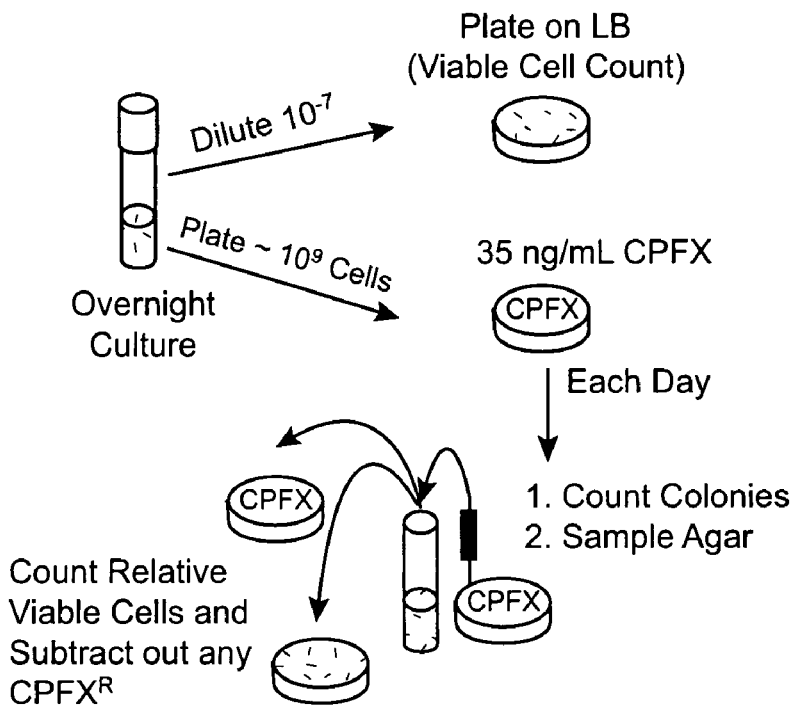
Verify Adaptive Mutation
Plate representative number of
day 2, day 3, ect.
colonies on 0.035 µg/ml CPFX
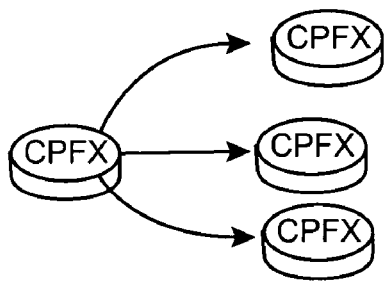
Fig. 2

Active Site Geometry of LexA
S119 attacks the C=O of Ala-Gly

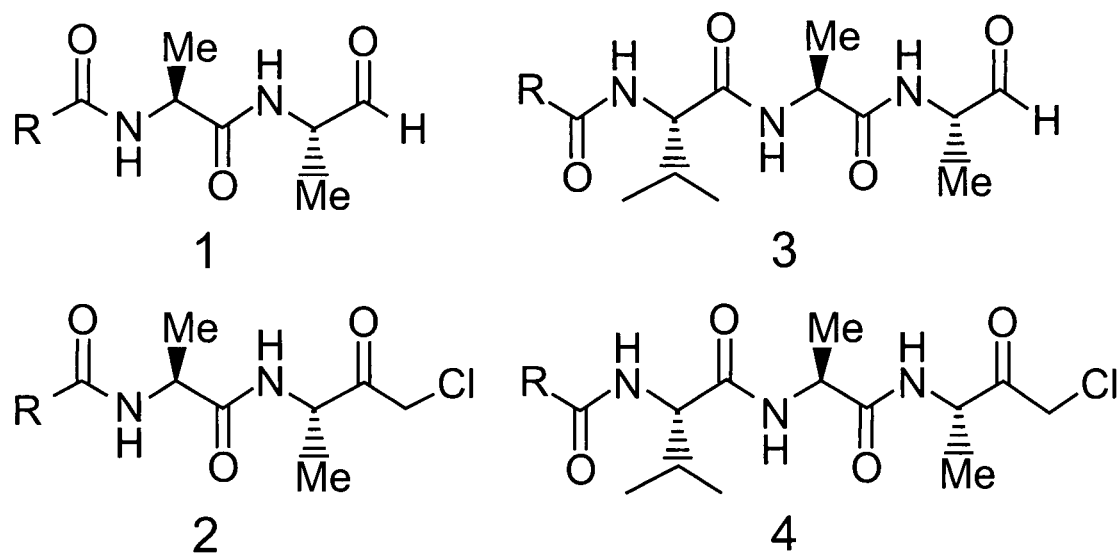
R = Me
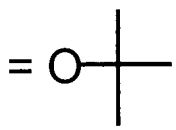
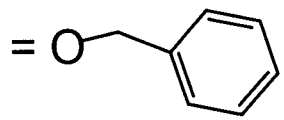
Fig. 16

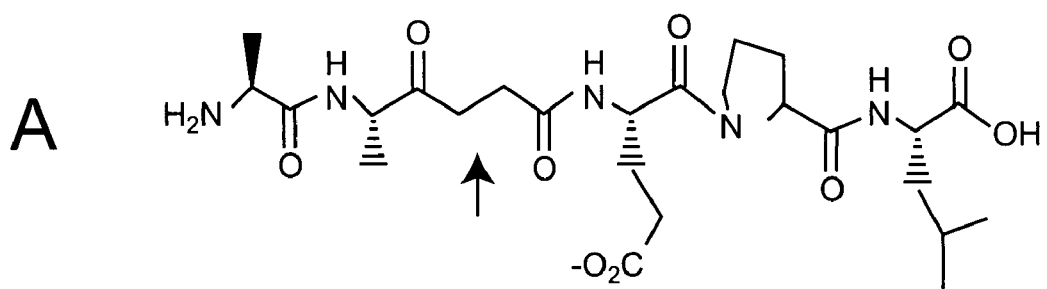
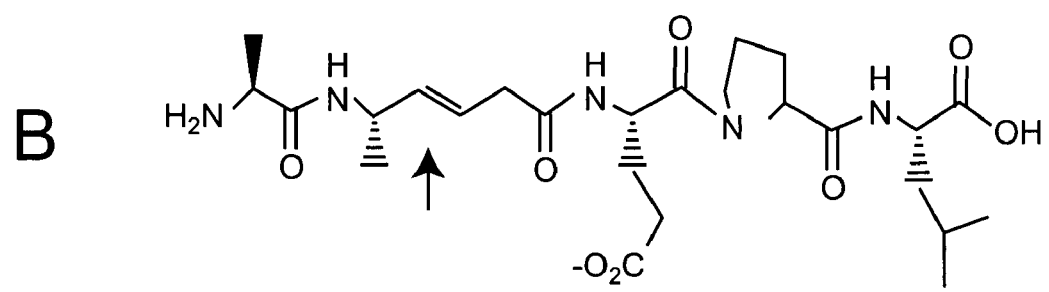
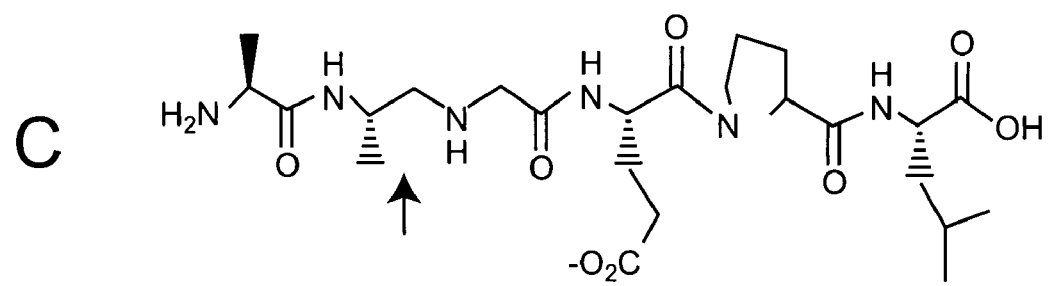
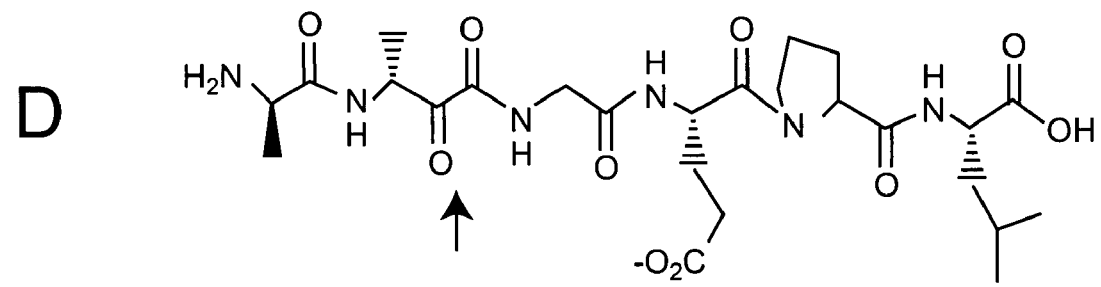
Fig. 17

| Primer Name | Sequence (5'>3') |
| --- | --- |
| camF | TCGAGATTTTCAGGAGCTAAG |
| camR | GCCGGCACCAATAACTGCCTT |
| dinB_CF(Kan) | GAGACACAACGTGGCTTTCCCTGGGATTATGATGTATACT |
| dinB_CR | GCTTCGTCATTCGTTCTGCTG |
| dinBNF | CGCGTGCTGATTAAAGACG |
| dinB_NR(Kan) | GCGGCTTTGTTGAATAAATCGGATTTTACGCATTGCTCACC |
| gyrA_1KbR | CAGGTTCATGATCTTCGGCTG |
| gyrA_OrfF | GATGAGCGACCTTGCGAGAG |
| gyrA_Seq | GTACACCGTCGCGTACTTTAC |
| kanF | GGAAAGCCACGTTGTGTCTC |
| kanR | CGATTTATTCAACAAAGCCGC |
| kanR_NdeI | GGTTGGCATATGCGATTTATTCAACAAAGCCGC |
| lacZ_CF(Kan) | GAGACACAACGTGGCTTTCCGGTCGCTACCATTACCAGTTG |
| lacZ_CR | CAGCCAACACAGCCAAACATC |
| lacZ_NF | CCATGCAAATGCTGAATGAGG |
| lacZ_NR(Kan) | GCGGCTTTGTTGAATAAATCGGGTCATAGCTGTTTCCTGTG |
| lexA_CF | GCGACACAACGTGGCTTTCCCATATCTCTGAGACCGCGATG |
| lexA_CR | GCTTAACCAGCGGATTTCAAG |
| lexA_NF_SphI | TTGGTTGCATGCCAATGGCCAATAATACCACTGG |
| lexA_OrfR_NdeI | GGTTGGCATATGCAGAGATATGTTACAGCCAGTC |
| lexA_S119A_QCF | CCTTCCTTATTCAAGCCGAATGGCGATTTCCTGCTGCGCGTCAGC |
| lexA_S119A_QCR | GCTGACGCGCAGCAGGAAATCGCCATTCGGCTTGAATAAGGAAGG |
| lexA_Seq | CAGGAAGAGGAAGGGGTTG |
| polB_CF(Kan) | GAGACACAACGTGGCTTTCCGGGCAACTTGGGCTATTTTGA |
| polB_CFSpec | CTTATGTCCACTGGGTTCGTGGGGCAACTTGGGCTATTTTGA |
| polB_CR | GGTTTGCTGAACACCAGTTTG |
| polB_NF | CATCGAAACCGGTGAAGTGG |
| polB_NR(Kan) | GCGGCTTTCTTGAATAAATCGCTGCGCCACGCTGAAAATCC |
| polB_NRSpec | CTAGCGAGGGCTTTACTAAGCCTGCGCCACGCTGAAAATCC |
| priA_CF(Kan) | GAGACACAACGTGGCTTTCCGGTTAAACCGCTCACGATGCG |
| priA_CR | GATGCGCACAGTCGCCAATCAGC |
| priA_NF | CCGCTGTTTTCGTGGTAATACG |
| priA_NR(Kan) | GCGGCTTTGTTGAATAAATCGGGCAACGGGCATAGCATCATC |
| recA_CF(Kan) | GAGACACAACGTGGCTTTCCGAAGGCGTAGCAGAAACTAAC |
| recA_CR | CGATAGAGCAGAAAACGCTG |
| recA_NF | GTTAAGTGAACAGGTTGGGC |
| recA_NR(Kan) | GCGGCTTTGTTGAATAAATCGGTCGATAGCCATTTTTACTCC |
| recB)CF(Kan) | GAGACACAACGTGGCTTTCCGAGGAGGCGTAATGAAATTGC |
| recB_CR | GCTTTGCGCCAGTAGAGCTTC |
| recB_NF | GCTATGCCGTGTTTGCGTTTC |
| recB)NR(Kan) | GCGGCTTTGTTGAATAAATCGGGCGACATCACTCATTCTTTTCAC |
| recD_CF(Kan) | GAGACACAACGTGGCTTTCCCGGGAATAAACGTAATTGCCG |
| recD_CR | GATTCGTCGCGCAACAATCAACG |
| recD_NF | CGCAATAAACAGGTGGAGATG |
| recD_NR(Kan) | GCGGCTTTGTTGAATAAATCGCAATTTCATTACGCCTCCTCC |
| recG_CF(Kan) | GAGACACAACGTGGCTTTCCCGTTACTCGAATGCGTAAAAGGCG |
| recG_CR | CGTAAGCTTGTCGTTGTTCC |
| recG_NF | GTTGGCGTACATGAAGTTC |
| recG_NR(Kan) | GCGGCTTTGTTGAATAAATCGGCGAGGTTTCATGGCACTTAC |
| ruvB_CF(Kan) | GAGACACAACGTGGCTTTCCGAAATGCCGTAAGTCGGATTG |
| ruvB_CR | CTGTCAATGACGATAAGCCCG |
| ruvB_NF | CACTTTGTGGTGCGTGAAGAC |
| ruvB_NR(Kan) | GCGGCTTTGTTGAATAAATCGGTCTGCTTCAATCATCCTTTACC |
| ruvC_CF(Kan) | GAGACACAACGTGGCTTTCCCGACTGCGTTAAGTTATACCG |
| ruvC_CR | CGTCGGGATCATTATCGGTC |
| ruvC_NF | CCATCATCTACGAAGGTTACG |
| ruvC_NR(Kan) | GCGGCTTTGTTGAATAAATCGGAGAATAATAGCCATCACGC |
| specF | ATTCCCCTGCTCGCGCAGGC |
| specR | GCTTAGTAAAGCCCTCGCTA |
| umuDC_CF(Kan) | GAGACACAACGTGGCTTTCCGTCAAATAAATATAGCGGCAGG |
| umuDC_CFCam | CTTAGCTCCTGAAAATCTCGAGTCAAATAAATATAGCGGCAGG |
| umuDC_CR | CGTGGCTGTTGATGGCGTTTAC |
| umuDC_NF | GTAAGGTTTTAATATCGCCG |
| umuDC_NR | GCGGCTTTGTTGAATAAATCGCATAATAATCTGCCTGAAGTTATAC |
| umuDC_NRCam | AAGGCAGTTATTGGTGCCGGCCATAATAATCTGCCTGAAGTTA |

Fig. 19

Peptide 1: RVAAGEPL. Peptide 2: VAAGEP (both C-term amides, commercial sourse)
Peptide 3: VAAGEPL (C-term acid, made in house)

SEQUENCE LISTING

```
<160> NUMBER OF SEQ ID NOS: 74

<210> SEQ ID NO 1
<211> LENGTH: 4
<212> TYPE: PRT
<213> ORGANISM: Artificial
<220> FEATURE:
<223> OTHER INFORMATION: synthetic peptide corresponding to LexA
      cleavage site

<400> SEQUENCE: 1

Val Ala Ala Gly
1
```

```
<210> SEQ ID NO 2
<211> LENGTH: 7
<212> TYPE: PRT
<213> ORGANISM: Artificial
<220> FEATURE:
<223> OTHER INFORMATION: synthetic peptide corresponding to LexA
      cleavage site

<400> SEQUENCE: 2

Val Ala Ala Gly Glu Pro Leu
1               5

<210> SEQ ID NO 3
<211> LENGTH: 10
<212> TYPE: PRT
<213> ORGANISM: Artificial
<220> FEATURE:
<223> OTHER INFORMATION: synthetic peptide corresponding to LexA
      cleavage site

<400> SEQUENCE: 3

Val Ala Ala Gly Glu Pro Leu Leu Ala Trp
1               5                   10

<210> SEQ ID NO 4
<211> LENGTH: 8
<212> TYPE: PRT
<213> ORGANISM: Artificial
<220> FEATURE:
<223> OTHER INFORMATION: synthetic peptide corresponding to LexA
      cleavage site

<400> SEQUENCE: 4

Arg Val Ala Ala Gly Glu Pro Leu
1               5

<210> SEQ ID NO 5
<211> LENGTH: 6
<212> TYPE: PRT
<213> ORGANISM: Artificial
<220> FEATURE:
<223> OTHER INFORMATION: synthetic peptide corresponding to LexA
      cleavage site

<400> SEQUENCE: 5

Val Ala Ala Gly Glu Pro
1               5

<210> SEQ ID NO 6
<211> LENGTH: 6
<212> TYPE: PRT
<213> ORGANISM: Artificial
<220> FEATURE:
<223> OTHER INFORMATION: synthetic peptide corresponding to LexA
      cleavage site

<400> SEQUENCE: 6

Ala Ala Gly Glu Pro Leu
1               5

<210> SEQ ID NO 7
<211> LENGTH: 4
<212> TYPE: PRT
<213> ORGANISM: Artificial
<220> FEATURE:
<223> OTHER INFORMATION: synthetic peptide corresponding to seqeunce
      N-terminal of LexA scissile bond

<400> SEQUENCE: 7
```

-continued

Arg Val Ala Ala
1

<210> SEQ ID NO 8
<211> LENGTH: 4
<212> TYPE: PRT
<213> ORGANISM: Artificial
<220> FEATURE:
<223> OTHER INFORMATION: synthetic peptide corresponding to seqeunce
      C-terminal of LexA scissile bond

<400> SEQUENCE: 8

Gly Glu Pro Leu
1

<210> SEQ ID NO 9
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 9 tcgagattt caggagctaa g                                          21

<210> SEQ ID NO 10
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 10
gccggcacca ataactgcct t                                         21

<210> SEQ ID NO 11
<211> LENGTH: 40
<212> TYPE: DNA
<213> ORGANISM: Artificial
<220> FEATURE:
<223> OTHER INFORMATION: synthetic oligonucleotide primer

<400> SEQUENCE: 11
gagacacaac gtggctttcc ctgggattat gatgtatact                     40

<210> SEQ ID NO 12
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 12
gcttcgtcat tcgttctgct g                                         21

<210> SEQ ID NO 13
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 13
cgcgtgctga ttaaagacg                                            19

<210> SEQ ID NO 14
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 14
gcggctttgt tgaataaatc ggattttacg cattgctcac c        41

<210> SEQ ID NO 15
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 15
caggttcatg atcttcggct g        21

<210> SEQ ID NO 16
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 16
gatgagcgac cttgcgagag        20

<210> SEQ ID NO 17
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 17
gtacaccgtc gcgtacttta c        21

<210> SEQ ID NO 18
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 18
ggaaagccac gttgtgtctc        20

<210> SEQ ID NO 19
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 19
cgatttattc aacaaagccg c        21

<210> SEQ ID NO 20
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 20
ggttggcata tgcgatttat tcaacaaagc cgc                            33

<210> SEQ ID NO 21
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 21
gagacacaac gtggctttcc ggtcgctacc attaccagtt g                   41

<210> SEQ ID NO 22
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 22
cagccaacac agccaaacat c                                         21

<210> SEQ ID NO 23
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 23
ccatgcaaat gctgaatgag g                                         21

<210> SEQ ID NO 24
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 24
gcggctttgt tgaataaatc gggtcatagc tgtttcctgt g                   41

<210> SEQ ID NO 25
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 25
gagacacaac gtggctttcc catatctctg agaccgcgat g                   41

<210> SEQ ID NO 26
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 26
gcttaaccag cggatttcaa g                                         21

<210> SEQ ID NO 27
<211> LENGTH: 34

```
<212> TYPE: DNA
<213> ORGANISM: Artificial
<220> FEATURE:
<223> OTHER INFORMATION: synthetic oligonucleotide primer

<400> SEQUENCE: 27
ttggttgcat gccaatggcc aataatacca ctgg                               34

<210> SEQ ID NO 28
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 28
ggttggcata tgcagagata tgttacagcc agtc                               34

<210> SEQ ID NO 29
<211> LENGTH: 45
<212> TYPE: DNA
<213> ORGANISM: Artificial
<220> FEATURE:
<223> OTHER INFORMATION: synthetic oligonucleotide primer

<400> SEQUENCE: 29
ccttccttat tcaagccgaa tggcgatttc ctgctgcgcg tcagc                   45

<210> SEQ ID NO 30
<211> LENGTH: 45
<212> TYPE: DNA
<213> ORGANISM: Artificial
<220> FEATURE:
<223> OTHER INFORMATION: synthetic oligonucleotide primer

<400> SEQUENCE: 30
gctgacgcgc agcaggaaat cgccattcgg cttgaataag gaagg                   45

<210> SEQ ID NO 31
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 31
caggaagagg aagaagggtt g                                             21

<210> SEQ ID NO 32
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 32
gagacacaac gtggctttcc gggcaacttg ggctattttg a                       41

<210> SEQ ID NO 33
<211> LENGTH: 42
<212> TYPE: DNA
<213> ORGANISM: Artificial
<220> FEATURE:
<223> OTHER INFORMATION: synthetic oligonucleotide primer

<400> SEQUENCE: 33
```
cttatgtcca ctgggttcgt ggggcaactt gggctatttt ga          42

<210> SEQ ID NO 34
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 34
ggtttgctga acaccagttt g                                  21

<210> SEQ ID NO 35
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 35
catcgaaacc ggtgaagtgg                                    20

<210> SEQ ID NO 36
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 36
gcggctttgt tgaataaatc gctgcgccac gctgaaaatc c            41

<210> SEQ ID NO 37
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 37
ctagcgaggg ctttactaag cctgcgccac gctgaaaatc c            41

<210> SEQ ID NO 38
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 38
gagacacaac gtggctttcc ggttaaaccg ctcacgatgc g            41

<210> SEQ ID NO 39
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 39
gatgcgcaca gtcgccaatc agc                                23

<210> SEQ ID NO 40
<211> LENGTH: 22
<212> TYPE: DNA
<213> ORGANISM: Artificial

```
<220> FEATURE:
<223> OTHER INFORMATION: synthetic oligonucleotide primer

<400> SEQUENCE: 40
ccgctgtttt cgtggtaata cg                                              22

<210> SEQ ID NO 41
<211> LENGTH: 42
<212> TYPE: DNA
<213> ORGANISM: Artificial
<220> FEATURE:
<223> OTHER INFORMATION: synthetic oligonucleotide primer

<400> SEQUENCE: 41
gcggctttgt tgaataaatc gggcaacggg catagcatca tc                        42

<210> SEQ ID NO 42
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 42
gagacacaac gtggctttcc gaaggcgtag cagaaactaa c                         41

<210> SEQ ID NO 43
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 43
cgatagagca gaaaacgctg                                                 20

<210> SEQ ID NO 44
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 44
gttaagtgaa caggttgggc                                                 20

<210> SEQ ID NO 45
<211> LENGTH: 42
<212> TYPE: DNA
<213> ORGANISM: Artificial
<220> FEATURE:
<223> OTHER INFORMATION: synthetic oligonucleotide primer

<400> SEQUENCE: 45
gcggctttgt tgaataaatc ggtcgatagc cattttact cc                         42

<210> SEQ ID NO 46
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 46
gagacacaac gtggctttcc gaggaggcgt aatgaaattg c                         41
```

```
<210> SEQ ID NO 47
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 47
ggtttgcgcc agtagagctt c                                              21

<210> SEQ ID NO 48
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 48
gctatgccgt gtttgcgttt c                                              21

<210> SEQ ID NO 49
<211> LENGTH: 45
<212> TYPE: DNA
<213> ORGANISM: Artificial
<220> FEATURE:
<223> OTHER INFORMATION: synthetic oligonucleotide primer

<400> SEQUENCE: 49
gcggctttgt tgaataaatc gggcgacatc actcattctt ttcac                    45

<210> SEQ ID NO 50
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 50
gagacacaac gtggctttcc cgggaataaa cgtaattgcc g                        41

<210> SEQ ID NO 51
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 51
gattcgtcgc gcaacaatca acg                                            23

<210> SEQ ID NO 52
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 52
cgcaataaac aggtggagat g                                              21

<210> SEQ ID NO 53
<211> LENGTH: 42
<212> TYPE: DNA
<213> ORGANISM: Artificial
<220> FEATURE:
<223> OTHER INFORMATION: synthetic oligonucleotide primer
```

<400> SEQUENCE: 53
gcggctttgt tgaataaatc gcaatttcat tacgcctcct cc                              42

<210> SEQ ID NO 54
<211> LENGTH: 44
<212> TYPE: DNA
<213> ORGANISM: Artificial
<220> FEATURE:
<223> OTHER INFORMATION: synthetic oligonucleotide primer

<400> SEQUENCE: 54
gagacacaac gtggctttcc cgttactcga atgcgtaaaa ggcg                            44

<210> SEQ ID NO 55
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 55
cgtaagcttg tcgttgttcc                                                      20

<210> SEQ ID NO 56
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 56
gttggcgtac atgaagttc                                                       19

<210> SEQ ID NO 57
<211> LENGTH: 42
<212> TYPE: DNA
<213> ORGANISM: Artificial
<220> FEATURE:
<223> OTHER INFORMATION: synthetic oligonucleotide primer

<400> SEQUENCE: 57
gcggctttgt tgaataaatc ggcgacctttt catggcactt ac                             42

<210> SEQ ID NO 58
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 58
gagacacaac gtggctttcc gaaatgccgt aagtcggatt g                              41

<210> SEQ ID NO 59
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 59
ctgtcaatga cgataagccc g                                                    21

<210> SEQ ID NO 60

```
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 60
cactttgtgg tgcgtgaaga c                                              21

<210> SEQ ID NO 61
<211> LENGTH: 44
<212> TYPE: DNA
<213> ORGANISM: Artificial
<220> FEATURE:
<223> OTHER INFORMATION: synthetic oligonucleotide primer

<400> SEQUENCE: 61
gcggctttgt tgaataaatc ggtctgcttc aatcatcctt tacc                      44

<210> SEQ ID NO 62
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 62
gagacacaac gtggctttcc cgactgcgtt aagttatacc g                         41

<210> SEQ ID NO 63
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 63
cgtcgggatc attatcggtc                                                 20

<210> SEQ ID NO 64
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 64
ccatcatcta cgaaggttac g                                               21

<210> SEQ ID NO 65
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 65
gcggctttgt tgaataaatc ggagaataat agccatcacg c                         41

<210> SEQ ID NO 66
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 66
```
attccsctgc tcgcgcaggc                                                    20

<210> SEQ ID NO 67
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 67
gcttagtaaa gccctcgcta                                                    20

<210> SEQ ID NO 68
<211> LENGTH: 42
<212> TYPE: DNA
<213> ORGANISM: Artificial
<220> FEATURE:
<223> OTHER INFORMATION: synthetic oligonucleotide primer

<400> SEQUENCE: 68
gagacacaac gtggctttcc gtcaaataaa tatagcggca gg                           42

<210> SEQ ID NO 69
<211> LENGTH: 43
<212> TYPE: DNA
<213> ORGANISM: Artificial
<220> FEATURE:
<223> OTHER INFORMATION: synthetic oligonucleotide primer

<400> SEQUENCE: 69
cttagctcct gaaaatctcg agtcaaataa atatagcggc agg                          43

<210> SEQ ID NO 70
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 70
cgtggctgtt gatggcgttt ac                                                 22

<210> SEQ ID NO 71
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 71
gtaaggtttt aatatcgccg                                                    20

<210> SEQ ID NO 72
<211> LENGTH: 46
<212> TYPE: DNA
<213> ORGANISM: Artificial
<220> FEATURE:
<223> OTHER INFORMATION: synthetic oligonucleotide primer

<400> SEQUENCE: 72
gcggctttgt tgaataaatc gcataataat ctgcctgaag ttatac                       46

<210> SEQ ID NO 73
<211> LENGTH: 43
<212> TYPE: DNA

```
<213> ORGANISM: Artificial
<220> FEATURE:
<223> OTHER INFORMATION: synthetic oligonucleotide primer

<400> SEQUENCE: 73
aaggcagtta ttggtgccgg ccataataat ctgcctgaag tta                    43

<210> SEQ ID NO 74
<211> LENGTH: 18
<212> TYPE: DNA
<213> ORGANISM: Artificial
<220> FEATURE:
<223> OTHER INFORMATION: synthetic oligonucleotide

<400> SEQUENCE: 74
ttgttgttgt tgttgttg                                                18
```

COMPOSITIONS AND METHODS TO REDUCE MUTAGENESIS

CROSS-REFERENCE

This application claims the benefit under 35 U.S.C. §119 (e) of U.S. Provisional Patent Application No. 60/608,949, filed Nov. 19, 2003, which is hereby incorporated herein by reference in its entirety for all purposes.

STATEMENT OF GOVERNMENT INTEREST

This invention was made with government support under Contract No. N00014-03-1-0126 awarded by the Office of Naval Research. The government has certain rights in this invention.

BACKGROUND

Drug resistance is an ever increasing problem in modern medicine impacting the treatment of conditions as diverse as bacterial infections, viral infections, protozoan infections, fungal infections, and cancer.

In particular, the worldwide emergence of antibiotic-resistant bacteria threatens to undo the dramatic advances in human health that followed the discovery of these drugs. Antibiotic drug resistance is especially acute with tuberculosis, which infects one-third of all humans, most of whom live in the developing world. The health care establishment is countering this challenge by trying to create new antibiotics and by limiting the use of those already available. However, this approach has not yet produced the desired effect, as the prevalence of resistant strains continues to increase.

Drug resistance is also a problem with viruses, including the human immunodeficiency virus ("HIV"). In fact, HIV drug resistance is rapidly becoming an epidemic. One study of HIV infected patients between 1996 and 1999, shows that about 78% of patients harbored viruses that were resistant to at least one class of drugs, 51% had viruses that were resistant to two classes of drugs, and 18% had viruses that were resistant to three classes of drugs. Thus, HIV drug therapies must constantly evolve to keep pace with the evolution of resistance.

Drug resistance is also a problem during cancer therapy. It is estimated that half of all cancer patients are cured, mostly by a combination of surgery, radiotherapy and/or chemotherapy. However, some cancers can only be treated by chemotherapy, and in those cases, only one in five patients survives long-term. It is believed that the overriding reason for this poor result is drug resistance, wherein the tumors are either innately resistant to the drugs available, or else are initially sensitive but evolve resistance during treatment and eventually re-grow. Allen J D, et al. Cancer Research (2002) 62, 2294-2299.

Drug resistance also occurs with protozoa such as *Plasmodium* spp., the genus of protozoa responsible for malaria. In recent years, drug resistance has become one of the most important problems in malaria control. Resistance in vivo has been reported to all anti-malaria drugs except artemisinin and its derivatives. This necessitates the use of drugs which are more expensive and may have dangerous side effects.

Thus, there is a great need for compounds that inhibit the mutations that confer drug resistance and methods for using such compounds to treat and prevent drug resistant conditions.

SUMMARY OF THE INVENTION

The present invention relates to compositions comprising, consisting essentially of, or consisting of achaogens. Achaogens are compounds that reduce the rate of induced mutagenesis. Achaogens can include nucleic acids, peptide nucleic acids, phage, phagemids, polypeptides, peptidomimetics, antibodies, small or large organic or inorganic molecules or any combination of the above. Achaogens can be naturally occurring or non-naturally occurring (e.g., recombinant) and are preferably isolated and/or purified.

In preferred embodiments an achaogen interacts with or binds to a gene product that increases rate of mutation in a cell or an organism. Examples of such gene products include RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD or any homologs or analogs thereof.

In some embodiments, an achaogen interacts with or binds to LexA or any homolog or analog thereof to reduce the rate of mutation in a cell or an organism. Such an achaogen can, for example, interact with or bind to LexA's (or homolog of LexA's) cleavage site or active site. In some embodiments, an achaogen interferes with LexA's (or a homolog of LexA's) autocleavage, which is required for induced mutagenesis by binding to the active site of LexA (or homolog of LexA).

Such an achaogen can comprise, consist essentially of, or consist of a polypeptide or peptidomimetic of a polypeptide that binds LexA, thus preventing LexA's autoproteolysis activity. Examples of such polypeptide (and peptidomimetics thereof) include those comprising, consisting essentially of, or consisting of dipeptide Ala-Ala, tripeptide Val-Ala-Ala, or SEQ ID NO: 1, 2, or 3. In some embodiments wherein the achaogen comprises an Ala-Gly bond, the bond may be modified so that it is not cleavable under normal physiological conditions. In some embodiments, the polypeptide or peptidomimetic is C-terminally modified, e.g., such that it is electrophilic.

In some embodiments, an achaogen of the present invention is one of Formula I,

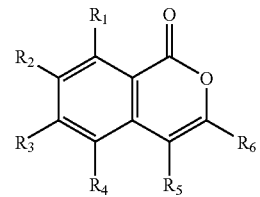

wherein where $R_1$, $R_2$, $R_3$, $R_4$, $R_5$, and $R_6$ are each independently selected from the group consisting of —(CHR$_a$)$_x$-L-R$_b$, where x is selected from the group consisting of 0, 1, 2, 3, or 4; L is a single bond or —C(O)—, —NHC(O)—, —OC(O)—, —S(O)$_j$, where j is 0, 1, or 2; R$_a$ is a moiety selected from the group consisting of H, (C$_1$-C$_6$)alkyl, halogen, (C$_1$-C$_6$)fluoroalkyl, (C$_1$-C$_6$)alkoxy, —C(O)OH, —C(O)—NH$_2$, —(C$_1$-C$_6$)alkylamine, —C(O)—(C$_1$-C$_6$)alkyl, —C(O)—(C$_1$-C$_6$)fluoroalkyl, —C(O)—(C$_1$-C$_6$)alkylamine, and —C(O)—(C$_1$-C$_6$)alkoxy; and R$_b$ is H, OH, halogen, NH$_2$, CN, N$_3$, or a moiety, optionally substituted with 1-3 independently selected substituents, selected from the group consisting of alkyl, alkenyl, alkoxy, mercaptyl, alkylamine, alkynyl, aryl, cycloalkyl, cycloalkenyl, and a heterocycle; in addition, $R_1$ and $R_2$, $R_2$ and $R_3$, $R_3$ and $R_4$, and $R_5$ and $R_6$, can optionally form a substituted or unsubstituted ring structure.

In some embodiments, an achaogen is an isolated and purified serine protease inhibitor.

In some embodiments, an achaogen functions as a negative regulator of induced mutagenesis. Such an achaogen can comprise, consist essentially of, or consist of a gene product that reduces the rate of mutation in a cell or an organism (e.g., PsiB, DinI, Lon protease, ClpXP protease, a serine protease inhibitor). In some embodiments, an achaogen is a phage or a phagemid carrying a recombinant nucleic acid encoding a gene product that reduces the rate of mutations in a cell or an organism.

In some embodiments, an achaogen is a nucleic acid that is complementary to a nucleic acid encoding a gene product that increases the rate of induced mutations (e.g., RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD, or homologs or analogs thereof). Such achaogens can be used as antisense nucleic acids, zinc fingers, RNAi or ribozymes to hybridize with and reduce the transcription and/or translation of such gene products.

The present invention also relates to pharmaceutical formulations whose active ingredient is an achaogen that reduces the rate of mutation in a cell or an organism. Such pharmaceutical compositions can be formulated for local or systemic delivery. Any of the pharmaceutical formulations herein can include additional therapeutic agent(s) such as, for example, antibiotics, antineoplastic agents, antifungal agents, antiprotozoan agents, and antiviral agents.

The invention herein also relates to methods of treating an organism suffering from a condition that may become drug resistant by administering to the organism an effective amount of an achaogen. An organism treated by the present invention can be an animal (e.g., a domesticated animal such as a cow, pig, horse, or a chicken, an avian, or a human) or a plant. The condition treated can be any condition that, when treated, results in drug resistance, including, for example, bacterial infections, viral infections, protozoan infections, fungal infections, and the abnormal cell growth associated with cancer. In particular, the present invention relates to methods of treating an organism suffering from a bacterial infection. The bacterial infection is one that may become resistant, or is resistant, to one or more antibiotic treatments.

The present invention also relates to methods for screening a cell, a group of cells of an organism, or an entire organism for the acquisition of drug resistance. Screening for drug resistance involves detecting mutations in an organism (or a cell or group of cells of an organism) in genes associated with induced mutation or detecting levels of protein expression of genes associated with induced mutation. For example in *E. coli*, such genes include, but are not limited to, a gene for a 16S rRNA, a gene for a 23S rRNA, clpXP, dinB, dinI, dnaE2, gyrA, gyrB, katG, inhA, ion protease, a gene for a L4 ribosomal methylases, lexA, lon protease, norA, recA, recN, psiB, parC, parE, polB, psiB, rpoS, rpoB, sxt, umuC, umuD, uvrA, uvrB, and uvrD. The presence of a mutation in such genes and/or the level of gene expression of such genes can be detected using a diagnostic tool such as a microarray or by sequencing techniques known in the art (e.g., PCR).

The present invention also relates to methods for screening for agents that interact with naturally occurring compositions that induce mutagenesis, e.g., RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD, or a LexA-RecA complex, or homologs or fragments thereof. Such methods include contacting a candidate agent from a library of candidate agents with a naturally composition that induce mutagenesis e.g., RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD, or a LexA-RecA complex, or homologs, analogs, or fragment thereof; and, in this manner, detecting a candidate agent that specifically binds to one or more of the compositions that induces mutagenesis. Such candidate agents can then be further modified to enhance binding to the naturally occurring composition.

The present invention also relates to methods for screening agents that interact with RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD, LexA-RecA complex, or any homolog, analog, or fragment thereof. Such methods include identifying a crystal complex of RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD, the LexA-RecA complex, or any homolog, analog, or fragment thereof; obtaining atomic coordinates of the crystal; and using the atomic coordinates with one or more molecular modeling techniques to identify an agent that interacts with the above molecules.

The present invention also provides kits. The kits described herein include at least one container comprising one or more achaogens that inhibit induced mutation along with direction for use. The kit may also include a second container of another therapeutic agent (e.g., an antibiotic, an antiviral, an antifungal, an antineoplastic, or an antiprotozoan medication). The achaogen and the second therapeutic agent can be combined prior to administration or may be administered separately. A kit can also include a diagnostic tool for determining if an organism or a cell or group of cells is partially or fully drug resistant.

BRIEF DESCRIPTION OF THE DRAWINGS

FIG. 2 illustrates a stressful lifestyle adaptive mutation (SLAM) assay.

FIG. 4A illustrates the enzyme's active cleft with its substrate. FIG. 4B illustrates the active cleft without its substrate.

FIG. 5A illustrates a crystal structure of the non-cleavable conformation of LexA. FIG. 5B illustrates the cleavable conformation of LexA.

FIG. 16 illustrates exemplary non-covalent peptidomimetic inhibitors of LexA.

FIG. 17 illustrates various covalent peptidomimetics inhibitors of LexA.

FIG. 19 illustrates oligonucleotide primers used in construction of disruption cassettes (SEQ ID NOs: 9-73).

DETAILED DESCRIPTION OF THE INVENTION

I. Definitions

Figure 1:
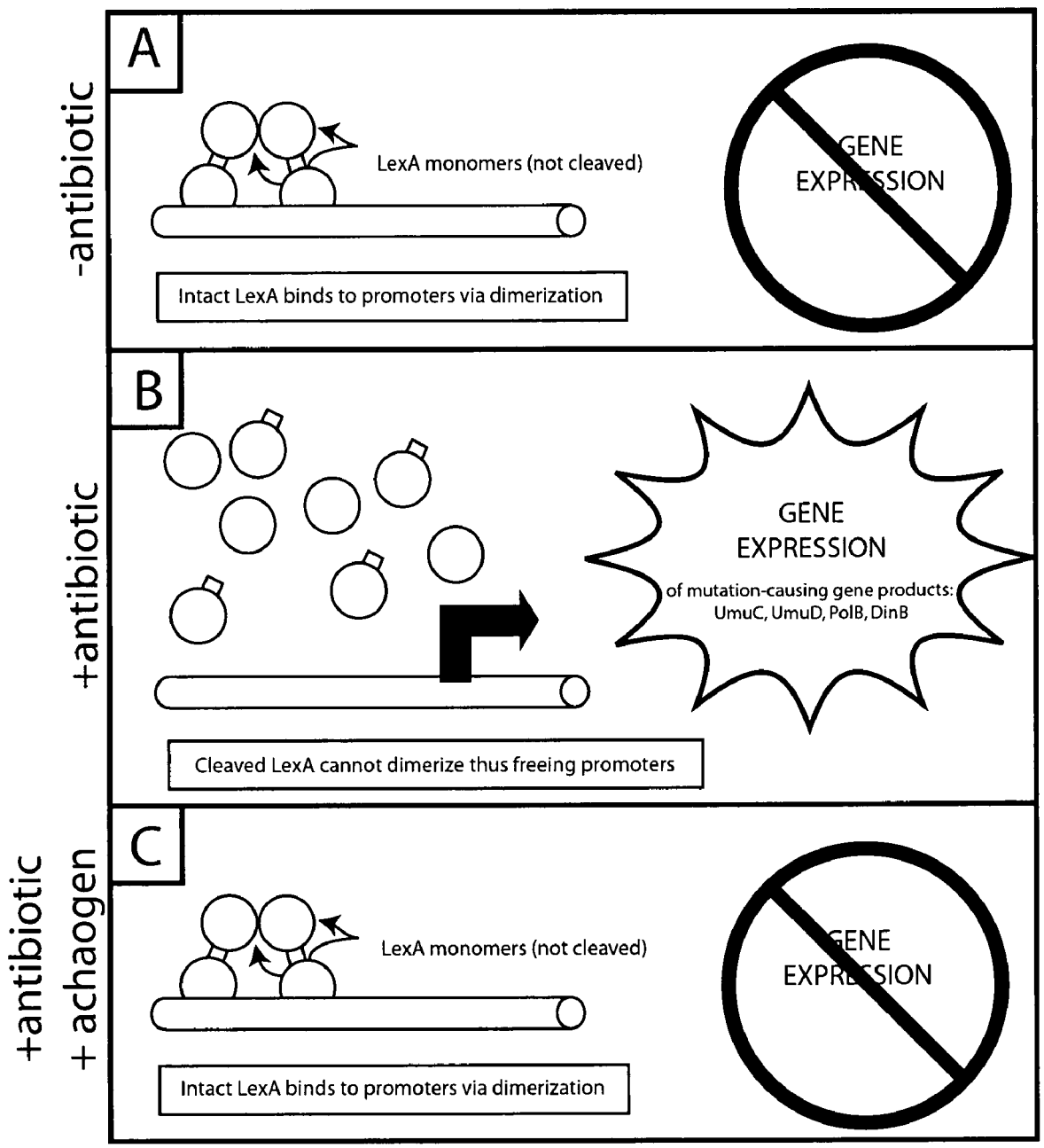
FIG. 1 illustrates the cellular function of LexA under normal conditions, under the condition of cellular stress, due to ciprofloxacin exposure and under the condition of cellular stress in the presence of an achaogen.

The term "Ac" as used herein is synonymous to the term "acetylated."

The term "achaogen" as used herein refers to an agent that inhibits the mutational process. That is, exposure of a cell or an organism to an achaogen results in a decrease in mutation frequency. The mutation frequency may be of an entire multicellular organism, a single celled organism, a population of cells, or some cells of an organism (as in the case of cancer). In some preferred embodiments, an achaogen reduces the rate of mutation by at least 2-fold, more preferably by at least 4-fold, more preferably by at least 6-fold, or more preferably by at least 8-fold order of magnitude. In some preferred embodiments, an achaogen reduces resistance to a single drug, more preferably, at least two drugs, more preferably, at least 3 drugs, or more preferably, at least 4 drugs, or more preferably, at least 5 drugs.

An "alkoxy" group refers to a (alkyl)O— group, where alkyl is as defined herein.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The "alkyl" moiety may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group could also be a "lower alkyl" having 1 to 8 carbon atoms. The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkylamine" refers to the —N(alkyl)$_x$H$_y$ group, where x and y are selected from the group x=1, y=1 and x=2, y=0. When x=2, the alkyl groups, taken together, can optionally form a cyclic ring system.

The term "alkenyl" refers to a type of alkyl group in which the first two atoms of the alkyl group form a double bond that is not part of an aromatic group. That is, an alkenyl group begins with the atoms —C(R)=C—R, wherein R refers to the remaining portions of the alkenyl group, which may be the same or different. Non-limiting examples of an alkenyl group include —CH=CH, —C(CH$_3$)=CH, —CH=CCH$_3$ and —C(CH$_3$)=CCH$_3$. The alkenyl moiety may be branched, straight chain, or cyclic (in which case, it would also be known as a "cycloalkenyl" group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. Non-limiting examples of an alkynyl group include —C—CH, —C≡CCH$_3$ and —C≡CCH$_2$CH$_3$. The "R" portion of the alkynyl moiety may be branched, straight chain, or cyclic.

An "amide" is a chemical moiety with formula —C(O) NHR or —NHC(O)R, where R is selected from the group consisting of alkyl, cycloalkyl, aryl, heteroaryl (bonded through a ring carbon) and heteroalicyclic (bonded through a ring carbon).

The term "amino acid" or "residue" as used herein includes any one of the twenty naturally occurring amino acids, the D-form of any one of the naturally-occurring amino acids, non-naturally occurring amino acids, and derivatives, analogs, and mimetics thereof. Any amino acid, including naturally occurring amino acids, may be purchased commercially or synthesized by methods known in the art. Examples of non-naturally-occurring amino acids include norleucine ("Nle"), norvaline ("Nva"), β-Alanine, L- or D-naphthalanine, ornithine ("Orn"), homoarginine (homoArg) and others well known in the peptide art, including those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Common amino acids may be referred to by their full name, standard single-letter notation, or standard three-letter notation for example: A, Ala, alanine; C, Cys, cysteine; D, Asp, aspartic; E, Glu, glutamic acid; F, Phe, phenylalanine; G, Gly, glycine; H, His, histidine; I, Ile isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine. Any and all of the amino acids in the compositions herein can be naturally occurring, synthetic, and derivatives or mimetics thereof. When the amino acid residues contain one or more chiral centers, any of the D, L, meso, threo or erythro (as appropriate) racemates or mixtures thereof, fall within the scope of this invention. In general, if it is desired to rely on non-enzymatic means of hydrolysis, D isomers should be used. On the other hand, L isomers may be more versatile since they can be susceptible to both non-enzymatic as well as potential targeted enzymatic hydrolysis, and are more efficiently transported by amino acid or dipeptidyl transport systems in the gastrointestinal tract. The amino acids herein can be naturally occurring or synthetic.

The term "analog" as used herein refers to a composition that retains the same structure or function (e.g., binding to a receptor) as a polypeptide or nucleic acid herein. Examples of analogs include peptidomimetics, peptide nucleic acids, small and large organic or inorganic compounds, as well as derivatives and variants of a polypeptide or nucleic acid herein. The term "derivative" or "variant" as used herein refers to a peptide or nucleic acid that differs from the naturally occurring polypeptide or nucleic acid by one or more amino acid or nucleic acid deletions, additions, substitutions or side-chain modifications. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality or size.

Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino acid with alanine), or alternatively, in which a naturally-occurring amino acid is substituted with a non-conventional amino acid. Preferably, amino acid substitutions are conservative.

Amino acid substitutions are typically of single residues, but may be of multiple residues, either clustered or dispersed. Additions encompass the addition of one or more naturally occurring or non-conventional amino acid residues. Deletion encompasses the deletion of one or more amino acid residues.

As stated above peptide derivatives include peptides in which one or more of the amino acids has undergone side-chain modifications. Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivitisation, for example, to a corresponding amide. Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl groups of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Proline residue may be modified by, for example, hydroxylation in the 4-position. Other derivatives contemplated by the present invention include a range of glycosylation variants from a completely unglycosylated molecule to a modified glycosylated molecule. Altered glycosylation patterns may result from expression of recombinant molecules in different host cells.

The term "aromatic" or "aryl" refers to an aromatic group which has at least one ring having a conjugated pi electron system and includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon.

The term "bond" or "single bond" refers to a chemical bond between two atoms, or two moieties when the atoms joined by the bond are considered to be part of larger substructure.

The term "complementary" as used herein describes two nucleotides that can associate with one another (e.g., form hydrogen bonds with one another). For example, adenine is complementary to thymine as they can form two hydrogen bonds.

The term "covalent" as used herein to describe a bond refers to a chemical bond between two species, and may involve single bonds or multiple bonds. The term "covalent" does not include hydrophobic/hydrophilic interactions, Hydrogen-bonding, van der Waals interactions, hydrophobic effect, and ionic interactions, which are deemed non-covalent.

A "cyano" group refers to a —CN group.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

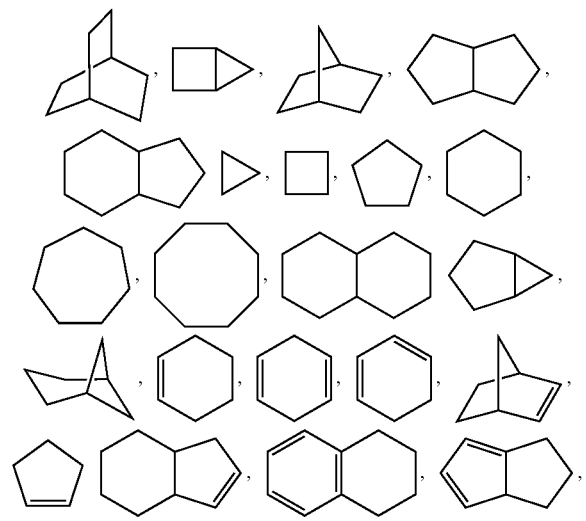

and the like.

The term "effective amount" as used herein refers to that amount of composition necessary to achieve the indicated effect.

The term "ester" refers to a chemical moiety with formula —COOR, where R is selected from the group consisting of alkyl, cycloalkyl, aryl, heteroaryl (bonded through a ring carbon) and heteroalicyclic (bonded through a ring carbon).

The terms "gene(s)" refers to a nucleic acid sequence (DNA, RNA, or analogs and/or combinations thereof) that encodes through its template or messenger RNA a sequence of amino acids characteristic of a specific peptide. The term "gene" can includes intervening, non-coding regions, as well as regulatory regions, and can include 5' and 3' ends. Examples of genes associated with induced mutations include but are not limited to lexA, recA, umuD, umuC, dinB, polB, etc., and any homologs, analogs or fragments thereof.

The term "gene product(s)" as used herein refers to is meant to include RNA transcribed from a gene, or a polypeptide encoded by a gene or translated from RNA. Such polypeptides can be unmodified translated polypeptides or post-translationally modified polypeptides (e.g., glycosylated, phosphonylated, cleaved, etc.). Examples of gene products that are associated with induced mutagenesis include LexA, RecA, PolB, Pol IV, UmuD, UmuC, and any homologs, analogs and fragments thereof.

The term "halo" or, alternatively, "halogen" means fluoro, chloro, bromo or iodo. Preferred halo groups are fluoro, chloro and bromo.

The terms "haloalkyl," "haloalkenyl," "haloalkynyl" and "haloalkoxy" include alkyl, alkenyl, alkynyl and alkoxy structures that are substituted with one or more halo groups or with combinations thereof. The terms "fluoroalkyl" and "fluoroalkoxy" include haloalkyl and haloalkoxy groups, respectively, in which the halo is fluorine.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Illustrative examples of heteroaryl groups include the following moieties:

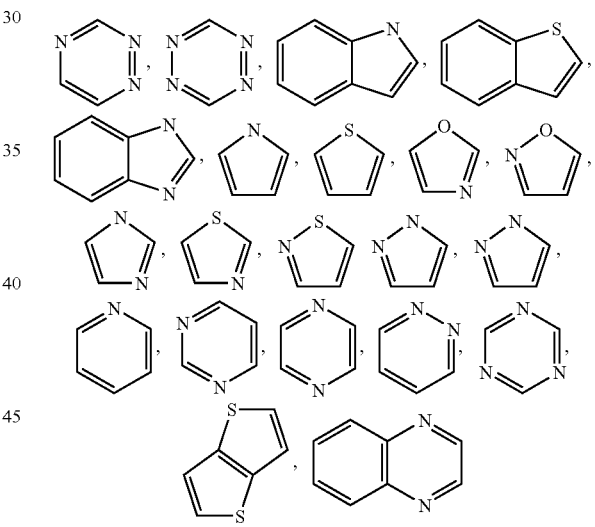

and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. The heterocyclic groups include benzo-fused ring systems and ring systems substituted with one or two oxo (=O) moieties such as pyrrolidin-2-one.

A "heteroalicyclic" group refers to a cycloalkyl group that includes at least one heteroatom selected from nitrogen, oxygen and sulfur. The radicals may be fused with an aryl or heteroaryl. Illustrative examples of heterocycloalkyl groups include:

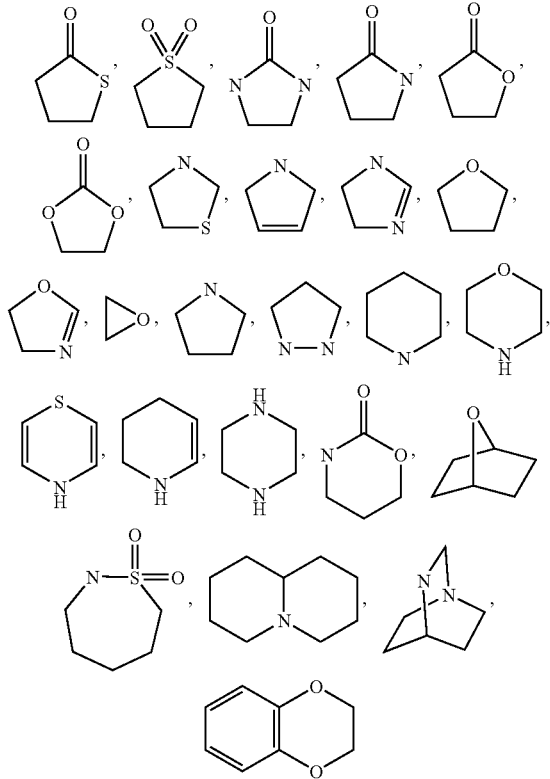

and the like. The term heteroalicyclic also includes all ring forms of the carbohydrates, including but not limited to the monosaccharides, the disaccharides and the oligosaccharides.

The term "homolog" or "homologous" as used herein refers to homology with respect to structure and/or function. With respect to sequence homology, sequences are homologs if they are at least 50%, preferably at least 60%, more preferably at least 70%, more preferably at least 80%, more preferably at least 90%, more preferably at least 95% identical, more preferably at least 97% identical, or more preferably at least 99% identical. The term "substantially homologous" refers to sequences that are at least 90%, more preferably at least 95% identical, more preferably at least 97% identical, or more preferably at least 99% identical. Homologous sequences can be the same functional gene in different species.

The term "hybridize" refers to interaction of a nucleotide sequence with a second nucleotide sequence. Such interaction can be, e.g., in solution or on a solid support, such as cellulose or nitrocellulose. If a nucleic acid sequence binds to a second nucleotide sequence with high affinity, it is said to "hybridize" to the second nucleotide sequence. The strength of the interaction between the two sequences can be assessed by varying the stringency of the hybridization conditions. Under highly stringent hybridization conditions only highly complementary nucleotide sequences hybridize.

The term "inhibition" or "inhibit" when referring to the activity of an achaogen refers to prevention or any detectable reduction in mutation rate.

An "isocyanato" group refers to a —NCO group.

The term "isolated" as used herein refers to a compound or molecule (e.g., a polypeptide or a nucleic acid) that is relatively free of other compounds or molecules such as proteins, lipids, nucleic acids or other molecules it normally is associated with in a cell. In general, an isolated polypeptide constitutes at least about 75% by weight of a sample containing it, more preferably about 90% of a sample containing it, more preferably about 95% of the sample containing it, or more preferably about 99% of a sample containing it.

An "isothiocyanato" group refers to a —NCS group.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

A "mercaptyl" group refers to a (alkyl)S— group.

The term "moiety" refers to a specific segment or functional group of a molecule. Chemical moieties are often recognized chemical entities embedded in or appended to a molecule.

The term "nucleic acid" as used herein refers to a ribo- or deoxyribonucleosides, ribo- or deoxyribonucleotides, ribo- or deoxyoligonucleotides, oligonucleotide sequence or polynucleotide sequence, or any variants, homologs, fragments, analogues or derivatives thereof. The nucleotide sequence may be naturally occurring or synthetic. It may be double-stranded or single-stranded whether representing the sense or antisense strand.

The terms "nucleophile" and "electrophile" as used herein have their usual meanings familiar to synthetic and/or physical organic chemistry. Carbon electrophiles typically comprise one or more alkyl, alkenyl, alkynyl or aromatic ($sp^3$, $sp^2$, or sp hybridized) carbon atoms substituted with any atom or group having a Pauling electronegativity greater than that of carbon itself. Examples of carbon electrophiles include but are not limited to carbonyls (aldehydes, ketones, esters, amides), oximes, hydrazones, epoxides, aziridines, alkyl-, alkenyl-, and aryl halides, acyls, sulfonates (aryl, alkyl and the like). Other examples of carbon electrophiles include unsaturated carbon atoms electronically conjugated with electron withdrawing groups, examples being the 6-carbon in alpha-unsaturated ketones or carbon atoms in fluorine substituted aryl groups. Methods of generating carbon electrophiles, especially in ways which yield precisely controlled products, are known to those skilled in the art of organic synthesis.

The term "optionally substituted" means that the referenced group may be substituted with one or more additional group(s) individually and independently selected from alkyl, cycloalkyl, aryl, heteroaryl, heteroalicyclic, hydroxy, alkoxy, aryloxy, mercapto, alkylthio, arylthio, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof. The protecting groups that may form the protective derivatives of the above substituents are known to those of skill in the art and may be found in references such as Greene and Wuts, above.

The term "organism" as used herein includes all living cells including microorganisms (e.g., viruses, bacteria, protozoa), plants, and animals (e.g., humans, birds, reptiles, amphibians, fish, and domesticated animals, such as cows, chicken, pigs, dogs, and goats).

The term "polypeptide" refers to any composition that includes two or more amino acids joined to each other by a peptide bond or peptidomimetic thereof. The term includes both short chains, which are also commonly referred to in the art as peptides, oligopeptides and oligomers, for example, and to longer chains, which generally are referred to in the art as proteins. The term "polypeptide" includes all polypeptides as described below. It will be appreciated that polypeptides often contain amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "peptidomimetic" as used herein refers to molecules which mimic an aspect of a polypeptide structure.

The term "purified" refers to a material (e.g., compound, molecule, or structure of interest) that is relatively free of other materials that it normally is associated with and is preferably at least 0.1%, 1%, 10%, 20%, 30%, 40%, 50%, 60%, 70%, 80%, 90%, 91%, 92%, 93%, 94%, 95%, 96%, 97%, 98%, 99% or 100% of total weight of the material.

The term "recombinant" as used herein refers with reference to material (e.g., a cell, a nucleic acid, a protein, or a vector) indicates that such material has been modified by the introduction of a heterologous material (e.g., a cell, a nucleic acid, a protein, or a vector). Thus, for example, recombinant cells express genes that are not found within the native (non-recombinant) form of the cell or express native genes that are otherwise abnormally expressed, under expressed or not expressed at all.

A "sulfinyl" group refers to a —S(=O)—R, where R is selected from the group consisting of alkyl, cycloalkyl, aryl, heteroaryl (bonded through a ring carbon) and heteroalicyclic (bonded through a ring carbon)

A "sulfonyl" group refers to a —S(=O)-2-R, where R is selected from the group consisting of alkyl, cycloalkyl, aryl, heteroaryl (bonded through a ring carbon) and heteroalicyclic (bonded through a ring carbon)

A "thiocyanato" group refers to a —CNS group.

The term "treatment" or "treating" as used herein refers to reducing or alleviating symptoms in a subject, preventing symptoms from worsening or progressing, or inhibition, elimination, or prevention of the infection, disorder or symptoms in a subject who is free therefrom.

II. In General

The particular mechanism by which a cell modulates its cellular environment to control mutation has been studied genetically in *E. coli* by monitoring mutation-mediated reversion or forward mutation of a gene required for cell growth. Reversion of a mutation occurs when a second mutation restores the function that was lost as a result of the first mutation. The second mutation causes a change in the DNA that either reverses the original alteration or compensates for it. The rate at which the second mutation occurs reflects the mutation rate of the bacteria under a set of conditions and can thus be used to measure induced mutation.

In *E. coli*, genes whose effect contributes to induced mutation are part of the SOS response system. The SOS response system in bacteria is a programmed series of gene derepression events which result in the induction of proteins involved in DNA replication, cell division, transposon mobility, lateral gene transfer, error-prone transleasion DNA synthesis, etc. which together result in an increased number of mutations. See Nickoloff, J. et al., (1998) DNA Damage and Repair (Totowa, N.J.: Humana Press); Huisman, O., Nature (1981) 290, 797-799; Kuan, C., et al., J. Bacteriol. (1992) 174, 6872-6877; and Matic, I., et al., Cell (1995) 80, 507-515. It is postulated that the SOS response process in bacteria is activated when a cell senses that its replicative polymerase (e.g., Pol III) has stalled.

The stalling of the replication polymerase Pol III, results in the accumulation of ssDNA. It is the ssDNA which binds to and activates RecA. RecA is a multifunctional protein known in *E. coli* to mediate both recombination and the induction of SOS responses to stress. Activated RecA binds to and activates the proteolysis of LexA and UmuD. See Goodman, M F, Annu. Rev. Biochem. (2002) 71:17-50; Nickoloff, J A and Hoekstra, M F (eds.) DNA Damage and Repair (Humana Press, Totowa, N.J., 1998).

Figure 5B:
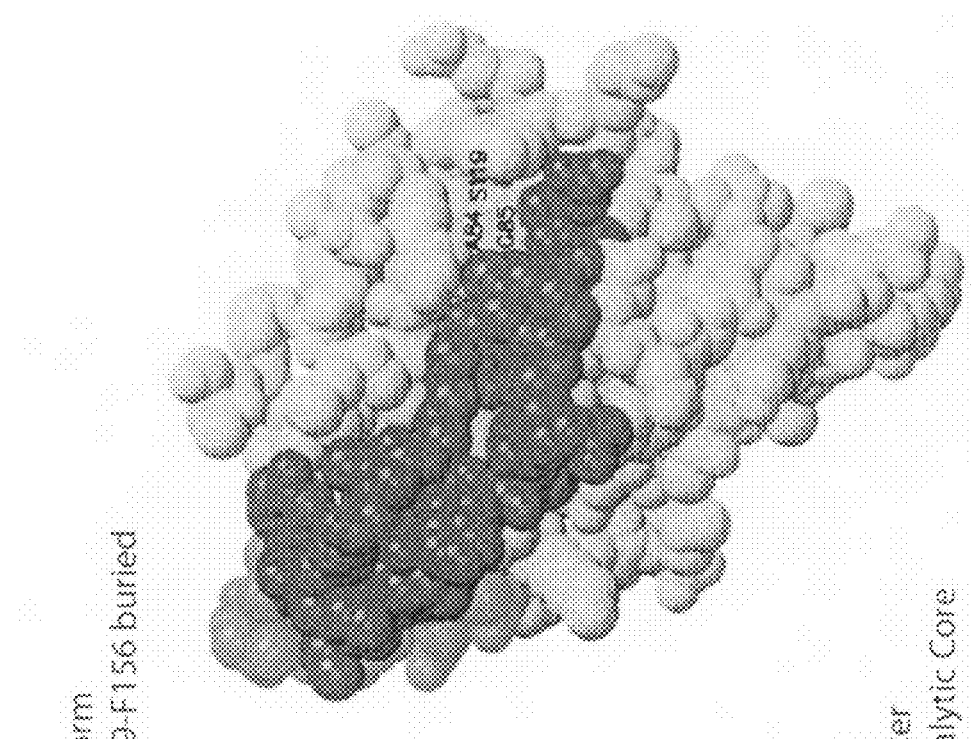
FIGS. 5A and 5B illustrate crystal structures of LexA in two conformations.
Figure 5A:
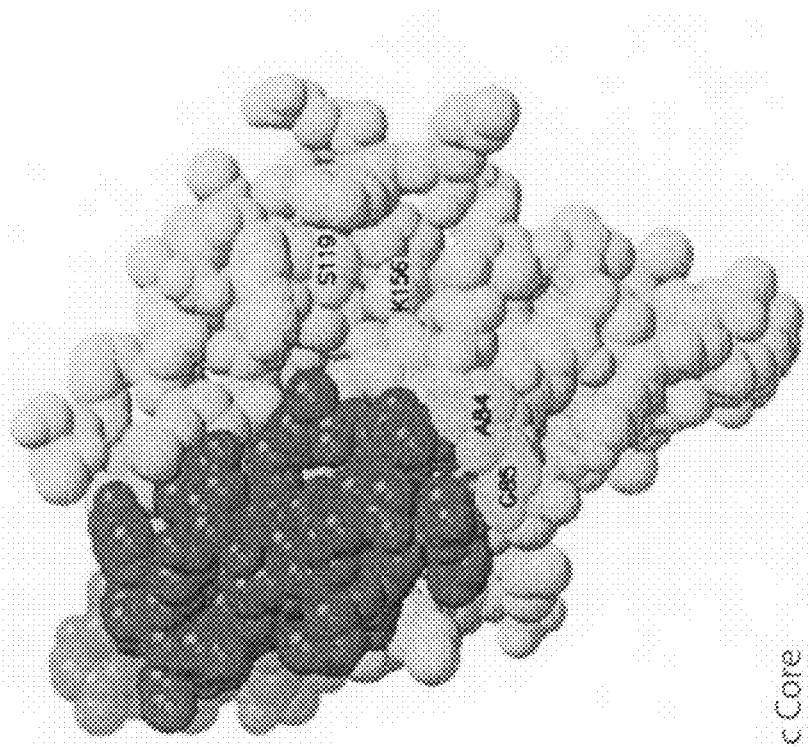

LexA proteolysis is an autocleavage reaction of the Ala84-Gly85 scissile bond of LexA. This cleavage bond separates LexA's DNA binding domain from its dimerization domain, destroying the protein's ability to repress genes that modulate induced mutagenesis. (Such genes include error-prone polymerases such as Pol IV and both subunits of Pol V as well as genes selected from the group consisting of 16S rRNA, 23S rRNA, clpXP, dinB, din, dnaE2, gyrA, gyrB, katG, inhA, lon protease, L4 ribosomal methylases, lexA, norA, recA. recN, psiB, parC, parE, polB, rpoS, rpoB, sxt, umuC, umuD, uvrA, uvrB, and uvrD.) Binding to RecA induces a conformational change in LexA, from a conformation that cannot undergo the self-cleavage reaction to one that can. Upon binding activated RecA, a loop containing Ala84 and Gly85 of LexA moves into the active site, which is a cleft located on the surface of the protein with a catalytic serine-lysine dyad at one end (FIGS. 5A-5B). The catalytic residues (Ser119 and Lys156) catalyze the peptidase reaction in a manner similar to that of serine proteases. See Roland, K L., *J. Biol. Chem.* (1990) 265, 12828-12835; van Diji, et al., *J. Biol. Chem.* (1995) 270, 3611-3618; Slilaty, S N., *Prot. Engineer.* (1991) 4, 919-922; and Leung, D., *J. Med. Chem.* (2000) 43, 305-341.

FIG. 1 depicts the state of LexA under normal conditions and under the condition of cellular stress due to ciprofloxacin exposure. Under normal conditions, as illustrated in FIG. 1A, LexA represses genes whose corresponding protein products are involved in the cellular response to stress, including gene products that cause mutation. See Goodman, M F, Annu. Rev. Biochem. (2002) 71:17-50; Nickoloff, J A, and Hoekstra, M F (eds.), DNA Damage and Repair, (Humana Press, Totowa, N.J., 1998). LexA monomers are bound to DNA, stabilized via interactions between adjacently bound LexA monomers. Each LexA monomer contains a dimerization domain that enables LexA to bind DNA cooperatively, as the LexA monomers bind DNA at adjacent operator sites and thereby stabilize one another's binding via inter-protein contacts. The binding of LexA dimers to their cognate binding sites prevents access of RNA polymerase to LexA-controlled promoters, keeping the intracellular concentrations of SOS response gene products low.

FIG. 1B illustrates what happens when bacteria are exposed to certain antibiotics (e.g., ciprofloxacin). See Mamber, S W., Antimicrob. Agents Chemother. (1993) 37:213-217; Riesenfeld, C., (1997) 41:2059-2060; Phillips, I., J. Antimicrob. Chemother., (1987) 20:631-638; Luo, Y., Cell (2001) 106:585-594; Shinagawa, H., *Proc. Nat'l. Acad. Sci. USA* (1988) 85:1806-1810; Rehrauer, W M., *J. Biol. Chem.* (1996) 271:23865-23873; and Balashov, S., *J. Mol. Biol.* (2002) 315:513-527. Such exposure activates the SOS response via the ssDNA-mediated activation of RecA. RecA has been shown to form a complex with ssDNA and ATP. This complex initiates recombination and also catalyzes the autoproteolysis of LexA.

Autoproteolysis of LexA results in the cleavage of LexA between its N and C terminal domains. After the proteolytic separation of the DNA binding and dimerization domains, LexA no longer cooperatively binds DNA to repress gene expression. As a result, SOS gene products are produced. Such SOS gene products include, for example, Pol IV and Pol V, which are encoded by dinB and umuDC, respectively. These gene products (and their analogs and homologs) may have different names in other organisms. Pol IV and Pol V (a heterodimer of UmuC and two copies of UmuD', a product of RecA-mediated cleavage of UmuD) are both error-prone, mutation-causing polymerases. It is the derepression of these polymerases which synthesize DNA with low fidelity, which is responsible for the increased rate of mutation at times of stress. Thus, the inhibition of the production or activity of these mutation causing polymerases may inhibit the evolution of antibiotic resistance. See also Yeiser, B., *Proc. Natl. Acad. Sci. USA* (2002) 99:8737-3841; McKenzie, G J., *Proc. Natl. Acad. Sci. USA* (2000) 97:6646-6651; Goodman, M F., *Curr. Opin. Genet. Dev.* (2000) 10:162-168; Shinagawa, H. in *Stress-Inducible Cellular Responses* (eds. Feige, U., Morimoto, R. I., Yahara, I. & Polla, B.) BirkhSuser Verlag, Basel, 1996; Sutton, M D., *Annu. Rev. Genet.* (2000) 34:479-497; Brotcorne-Lannoye, A., *Proc. Natl. Acad. Sci. USA* (1986) 83:3904-3908; Bull, H J., *Genetics* (2000) 154:1427-1437; Bull, H J., *Proc. Natl. Acad. Sci. USA*, (2001) 98:8334-8341; Kim, B., *Cell* (1993) 73:1165-1173; Napolitano, R., *EMBO* (2000) 19:6259-6265; Tang, M., *Nature* (2000) 404: 1014-1018; and Prakash, S., *Genes. Dev.* (2002) 16:1872-1883.

FIG. 1C illustrates what happens if an achaogen prevents LexA cleavage. In this scenario, the achaogen prevents the proteolysis of LexA, despite the presence of the antibiotic. As a result, the bacteria are not able to accelerate their rate of mutation, significantly decreasing their ability to evolve antibiotic resistance. Inhibition of mutation with an achaogen can be achieved via multiple strategies, including: (1) the inhibition of RecA (or any RecA ortholog) activation (2) the inhibition of RecA (or any RecA ortholog) binding to LexA or UmuD (or any LexA or UmuD ortholog) or any other yet to be identified component of the induced mutational response, or (3) the use of small molecules to inhibit the proteolysis of LexA or UmuD (or any LexA or UmuD ortholog).

One example of a gene associated with modulating induced mutagenesis is dnaE2. dnaE2 has been implicated in the emergence of drug resistance in *Mycobacterium tuberculosis* (MTB). See Boshoff, H., *Cell.* (2003) Vol. 113, 183-193. It has been suggested that MTb contains two functionally redundant replicative DNA polymerases: DnaE1 and DnaE2. See Boshoff, H., *Cell.* (2003) Vol. 113, 183-193. It has further been shown that mutations conferring resistance to rifampicin (Rif) in MTb are mediated primarily by dnaE2 as deletion of the gene prevents the accumulation of mutations conferring resistance. Thus, it has been suggested that DnaE2 is an error-prone translesion polymerase responsible for mutation conferring resistance to Rif.

Currently, MTb is commonly treated with an initial intensive 2-month regimen comprising multiple antibiotics: rifampicin (RIF), isoniazid (INH), pyrazinamide (PZA), and ethambutol (EMB) or streptomycin (SM), to ensure that mutants resistant to a single drug do not emerge and compromise therapy. See MMWR *Morb. Mortal Wkly. Rep.* (1993) 42 (RR-7). During the next 4 months, only RIF and INH are administered. INH and RIF are potent anti-MTb drugs that kill more than 99% of tubercular bacilli within 2 months of initiation of therapy. See Mitchison D A. *Bulletin International Union Against Tuberculosis* (1985) 65:30-7. Using these drugs in conjunction with each other, and possibly other drugs, shortens anti-MTb therapy from 18 months to 6 months. However, 2% of patients initiating multi-drug therapy develop drug resistant MTb by the end of the therapy, even with perfect compliance with the prescribed regimen.

III. Achaogens

In bacterial cells, as the cellular concentration of full-length LexA decreases due to LexA auto-proteolysis, the SOS genes are derepressed sequentially, in an order that depends on the affinity of their promoters for the LexA repressor. The first genes that are derepressed encode direct repair functions, including uvrA, uvrB, and uvrD. The cell first attempts to repair the damage, but if the damage persists, the next genes to be derepressed include recA, recN, and other genes that mediate more drastic recombinational repair pathways. Finally, if the damage still persists, the cell will first derepress dinB (which encodes the error-prone polymerase Pol IV) and then later derepress umuC and umuD (which encode the two subunits of the error-prone polymerase PolV). In this manner, only when the environment has become sufficiently lethal does the cell permit elevated rates of mutation.

An achaogen of the present invention is any agent that inhibits the mutation process in a cell, group of cells within an organism, or an entire organism. In particular, an achaogen is an agent that inhibits the mutation process, which is triggered in response to environmental stress or DNA damage.

Examples of environmental stresses that can induce mutagenesis or DNA damage include: drug treatment, UV radiation, restricted nutrients, etc.

A cell or an organism that may be undergoing or affected by induced mutations can be prokaryotic or eukaryotic. Examples of prokaryotic cells/organisms contemplated by the present invention include any of the bacterial strains disclosed herein. Examples of eukaryotic cells/organisms contemplated by the present invention include mammals, avians, plants, and in particular, humans. Thus, an organism whose mutation rate is reduced by an achaogen can be a microorganism (e.g., a virus or a bacterium) or a multicellular organism (e.g., a plant or animal).

The present invention relates to compositions comprising, consisting essentially of, and consisting of achaogens. As such a composition of the present invention can optionally include a second agent.

An achaogen can be naturally occurring or non-naturally occurring. An achaogen of the present invention is preferably isolated and/or purified. An achaogen of the present invention can comprise or consist of a nucleic acid, a polypeptide, a peptidomimetic, a peptide nucleic acid ("PNA"), an antibody, a phage, a phagemid, or a small or large organic or inorganic molecule. Salts, prodrugs, homologs or analogs of any of the achaogens herein are also a feature of the invention.

In some embodiments, an achaogen modulates, reduces, or inhibits the rate of mutation in a cell or an organism by interacting with or binding to a gene product that increases the rate of mutation either directly or indirectly. Examples of such gene products include, but are not limited to, RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD, or any homologs, analogs, fragments, or combinations thereof. Of course, an achaogen need not bind or interact with all of the above gene products. In some embodiments, an achaogen binds or interacts with only 1, 2, 3, 4, 5, 6, 7, 8, 9, 10, or 11 of the above gene products. For example, in some embodiments an acachaogen binds to or interacts with RecA. However, this is but one example of an achaogen and therefore in some embodiments, an achaogen does not bind to or interact with RecA. In other embodiments, an achaogen does not interact or bind to RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, or UvrD, or a homolog thereof.

Such modulation or inhibition can be mediated by an achaogen that is a direct inhibitor, competitive inhibitor or other form of inhibitor of such gene products. For example, an achaogen of the present invention can modulate or inhibit the rate of mutation by binding or interacting with a gene product that increases the rate of mutation, either covalently or non-covalently. In other examples, an achaogen can modulate or inhibit the rate of mutation by binding or interacting with a gene product that reduces the rate of mutation, either covalently or non-covalently.

In some embodiments, an achaogen is an inhibitor of RecA activation or RecA binding to ssDNA (e.g., a small molecule or peptidomimetic that interferes with RecA binding to ssDNA). This is but one example of an achaogen contemplated by the present invention, and as such, an achaogen of the present invention can one other than an achaogen that interacts with or binds to RecA.

In some embodiments, an achaogen is an inhibitor of LexA autocleavage (e.g., a peptidomimetic that competes with the cleavage site of LexA) or of a homolog or LexA. LexA is highly conserved in clinically relevant bacterial species (see Table 1 below). Thus, an achaogen contemplated by the present invention is one that interacts with or binds to LexA or any homolog, analogs, or fragments thereof and which can used to reduce induced mutations in a wide spectrum of bacterial infections.

TABLE 1

| LexA ortholog | Identical | Similar |
| --- | --- | --- |
| Escherichia coli K12 | 100% | 100% |
| Escherichia coli K12 0157 | 100% | 100% |
| Vibrio cholerae | 73% | 84% |
| Haemophilus influenzae | 67% | 83% |
| Pseudomonas syringae | 43% | 62% |
| Bacillus anthracis | 36% | 55% |
| Enterococcus faecalis | 35% | 50% |
| Staphylococcus aureus | 33% | 52% |
| Streptomyces coelicolor | 35% | 51% |

An achaogen interacting with LexA, preferably interacts with the "cleavage site" (substrate loop) of LexA or the "active site" of LexA. The "cleavage site" of LexA is a peptide sequence of LexA which includes the dipeptide bond Ala84-Gly85. In some embodiments, the cleavage site of LexA is preferably less than 50 amino acids in length, less than 40 amino acids in length, less than 30 amino acids in length, less than 20 amino acids in length, more preferably less than 15 amino acids in length, more preferably less than 10 amino acids in length, or more preferably less than 6 amino acids in length.

In some embodiments, the cleavage site of LexA comprises or consists of a polypeptide having amino acid sequence of VAAG (SEQ ID NO: 1), VAAGEPL (SEQ ID NO: 2) or VAAGEPLLAW (SEQ ID NO: 3), or any homolog or analog thereof.

The "active site" or substrate loop site of LexA comprises of a peptide sequence of LexA which includes Ser119 and Lys156. In some embodiments, the active site of LexA is less than 100 amino acids in length, more preferably less than 90 amino acids in length, more preferably less than 80 amino acids in length, more preferably less than 70 amino acids in length, more preferably less than 60 amino acids in length, or more preferably less than 50 amino acids in length.

Thus, in some embodiments, an achaogen interacts with either the cleavage site or the active site of LexA. Such interactions can be covalent or a non-covalent. Such achaogen can be a competitive inhibitor for the active site, a molecular decoy for LexA, or a specific protease that cleaves LexA.

In some embodiments, an achaogen is a peptide fragment of the LexA cleavage site or a peptidomimetic that mimics a LexA cleavage site, thereby competitively binding to LexA's internal active site preventing autoproteolysis. Examples of such achaogens include peptide fragments VAAG (SEQ ID NO: 1), VAAGEPL (SEQ ID NO: 2), VAAGEPLLAW (SEQ ID NO: 3), or any homologs or analogs thereof. Preferably such peptides and/or peptidomimetics or analogs thereof are isolated. Preferably, such peptides and/or peptidomimetics or analogs thereof include at least one non-cleavable bond. More preferably, the Ala-Gly bond is modified to be a non-cleavable bond.

Examples of non-cleavable peptidomimetics of the cleavage site of LexA are illustrated in FIGS. 15A-15D. In each of FIGS. 15A-15D the Ala84-Gly85 scissile bond was replaced with a non-cleavable analog. Such non-cleavable analogs include a keto-moiety (FIG. 15A), a trans-olefin moiety (FIG. 15B), a reduced amide moiety (FIG. 15C), and a α-keto moiety (FIG. 15D). In more preferred embodiments, a peptidomemtic of fewer than 10 amino acids spanning the scissile bond is constructed. For example, in FIGS. 16A-16D, a peptidomimetic of the AAGEPL (SEQ ID NO: 6) peptide with a replacement group replacing the Ala84-Gly85 scissile bond can include a keto-moiety (see FIG. 16A), trans-olefin moiety (FIG. 16B), reduced amide moiety (FIG. 16C), or α-keto moiety (FIG. 16D).

Figure 4A:
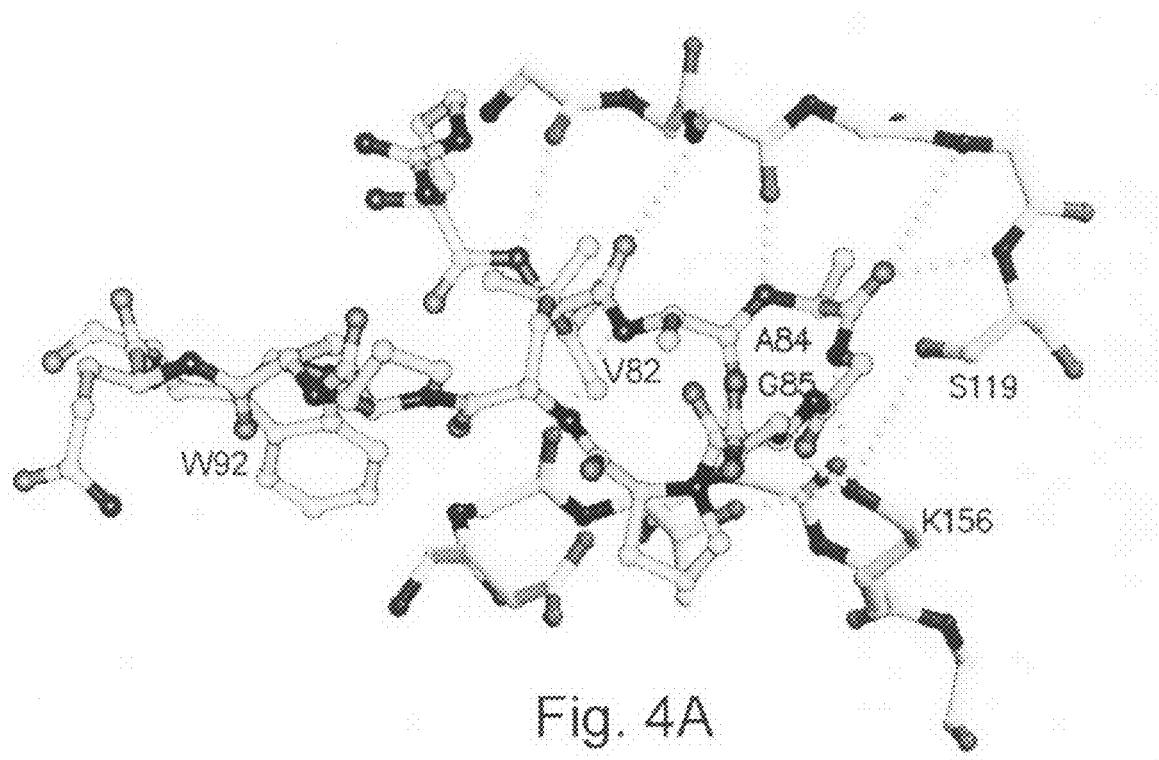
FIGS. 4A and 4B illustrate a portion (VAAG, SEQ ID NO: 1) of peptide VAAGEPLLAW (SEQ ID NO: 3) of the LexA substrate loop.
Figure 4B:
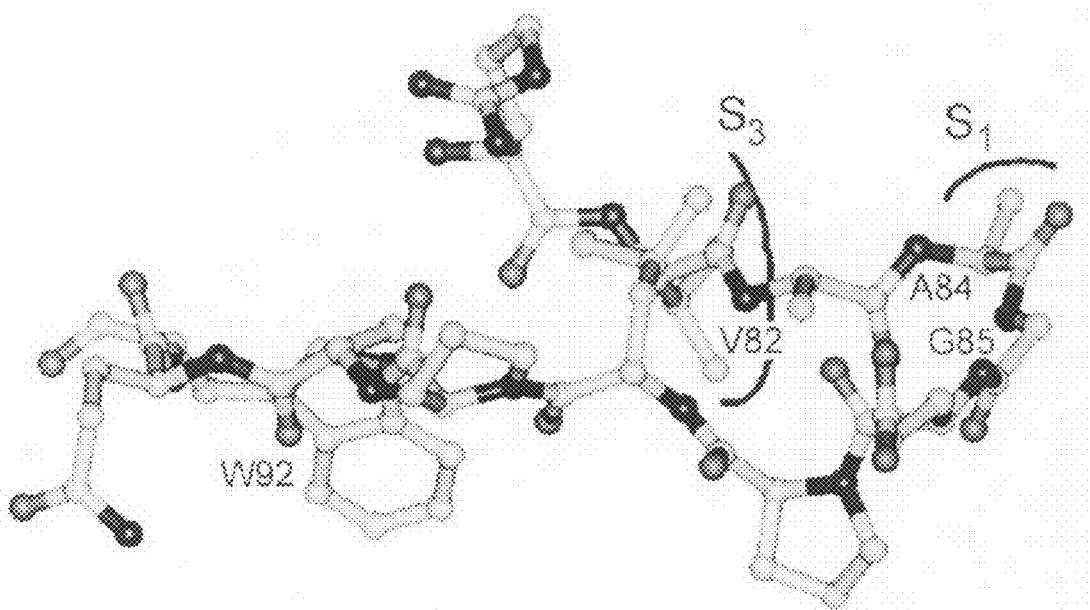

As depicted in FIGS. 4A and 4B, it is believed that a portion (e.g., VAAG) of LexA's cleavage site becomes situated within LexA's substrate loop during LexA's auto-proteolysis reaction. FIG. 4A depicts the enzyme's active cleft with its substrate. FIG. 4B depicts the substrate loop alone. Residues Arg81 to Ala84 of the cleavage site pack snugly in the cleft of the substrate loop with the side chains of Ala84 and Val82 hydrophobically packed in the S1 and S3 sites of the active site cleft (FIG. 4A). Interestingly, while quite distant from the scissile bond, mutation of Gln92 to Trp91 dramatically increases the affinity for the corresponding peptide in the active site, by increasing favorable interactions.

The crystal structure of *E. coli* LexA in both cleavable and non-cleavable conformations has been determined to 1.8 angstroms resolution (see FIGS. 5A-5B, respectively). See Luo, Y., Pfuetzner, R. A., Mosimann, S., Paetzel, M., Frey, E. A., Cherney, M., Kim, B., Little, J. W., and Strynadka N. C., Crystal structure of LexA: a conformational switch for regulation of self-cleavage. Cell, (2001) Vol. 106, 585-594. The structure suggests that the P sites located to the N-terminal side of the scissile bond make more important contact than the P site, located on the C-terminal side of the scissile bond.

Figure 6:
FIG. 6 illustrates the geometry of the active site of LexA and the position of S119 where it is poised to attack the C=O of Ala-Gly dipeptide.
Figure 7:
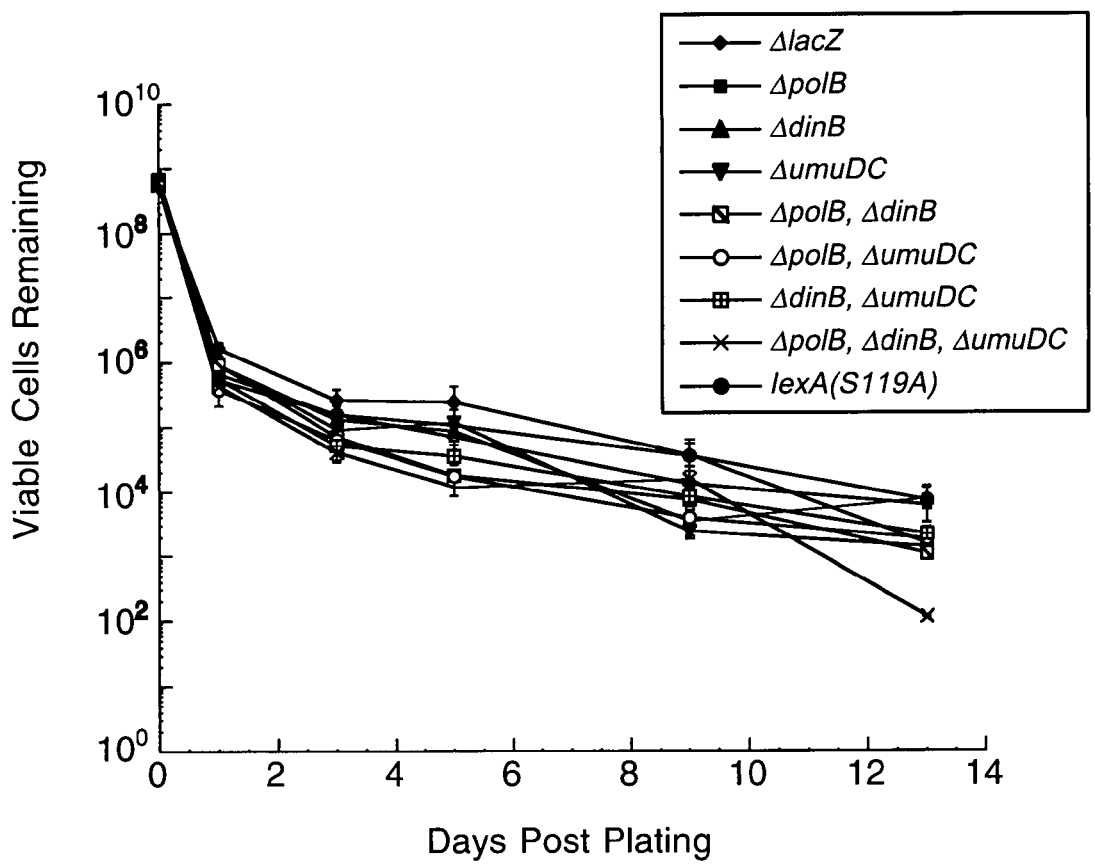
FIG. 7 illustrates a number of viable ciprofloxacin sensitive cells remaining on solid media (LB containing 35 ng/ml ciprofloxacin) as a function of time for SOS and polymerase deficient *E. coli* strains.

FIG. 6 depicts the LexA self-cleavage complex in which Ser119 (S119) of LexA attacks the C=O of the Ala84-Gly85 scissile peptide bond. It is suggested that Ser119 serves as the reactive nucleophile and attacks the Ala84-Gly85 peptide bond in manner analogous to a serine protease, while the uncharged Lys156 activates the Ser119 hydroxyl group. See Rolan K I, et al., J. Biol. Chem., (1990) 265, 22:12828-12835. Thus, the present invention contemplates a mutated LexA, having mutations in either or both the cleavage site or active site to disrupt substrate binding without disrupting the dimer formation of LexA. Such an achaogen can be a mutated LexA polypeptide (or homolog, analog, or fragment thereof). Such an achaogen can also be a nucleic acid encoding the mutated LexA polypeptide (or a homolog, analog, or fragment thereof).

Thus, in some embodiments, the present invention contemplates an achaogen that binds to the active site nucleotphile Ser119. Preferably such an achaogen binds to Ser119 covalently. This is but one example of an achaogen of the present invention, and in some embodiments, an achaogen is one other than an achaogen that binds to the active site nucleophile Ser119.

In some embodiments, such an achaogen comprises a peptide sequence located immediately to the N-terminal of the LexA scissile bond, or any homolog or analog thereof. Such achaogens comprise, consisting essentially of, or consist of a dipeptide Ala-Ala, a tripeptide Val-Ala-Ala or polypeptide Arg-Val-Ala-Ala (SEQ ID NO: 7), or any homolog or analog thereof. Such polypeptides, peptidomimetics, or analogs are preferably C-terminally modified to enhance its binding to the nucleophilic Ser119. These achaogens are one example of the achaogens contemplated herein, and as such, in some embodiments, an achaogen is one other than those comprising, consisting essentially of, or consisting of a dipeptide Ala-Ala, a tripeptide Val-Ala-Ala or polypeptide Arg-Val-Ala-Ala (SEQ ID NO: 7), or any homolog or analog thereof.

In some embodiments, such an achaogen comprises a peptide sequence located immediately to the C-terminus of the LexA scissile bond, or any homolog or analog thereof. Such peptides can include a dipeptide Gly-Glu, a tripeptide Gly-Glu-Pro or a peptide sequence of Gly-Glu-Pro-Leu (SEQ ID NO: 8), or any homolog or analog thereof. Such polypeptide, peptidomimetic, or analog thereof is preferably N-terminally modified to enhance its binding to the nucleophilic Ser119. These achaogens are one example of the achaogens contemplated herein, and as such, in some embodiments, an achaogen is one other than those comprising, consisting essentially of, or consisting of a dipeptide Gly-Glu, a tripeptide Gly-Glu-Pro or a peptide sequence of Gly-Glu-Pro-Leu (SEQ ID NO: 8), or any homolog or analog thereof.

Preferred C- and N-terminal modification that enhance binding of the peptide/peptidomimetic/analog to Ser119 are electrophile modifications. Examples of electrophile modifications include peptide aldehydes, trifluoroketones, chloromethyl ketones, and alpha-keto heterocycles. Examples of aldehydes and chlormethyl ketone analogs of the Ala-Ala dipeptide to the N-terminal of the scissile bond are illustrated in FIG. 17, compounds 1 and 2. Examples of the aldehydes and chloromethyl ketone analogs of the Val-Ala-Ala tripeptide to the N-terminal of the scissile bond are illustrated in FIG. 17, compounds 3 and 4.

Achaogens that interact with LexA are but one example of the achaogens contemplated herein, and as such, an achaogen of the present invention can be an achaogen other than one that interacts with or binds to LexA. In some embodiments, an achaogen is one other than that which interacts with the LexA cleavage site or the LexA active site.

In some embodiments, an achaogen is an inhibitor of RecA/LexA complex formation (e.g., a small molecule or peptidomimetic that interferes with the RecA/LexA complex formation). Again, this is but one example of an achaogen, and as such, an achaogen of the present invention can be an achaogen other than one that inhibits the RecA/LexA.

Any of the achaogen peptides or peptidomimetics herein can be further modified for slower release or degradation (e.g., using D-amino acid residues, PEG-terminus, etc.).

Synthesis of polypeptides and analogs thereof is known by those skilled in the art. In any of the embodiments herein, it is preferable that a peptide or a peptidomimetic of the present inventions fit within the substrate binding site. Therefore, a peptide or peptidomimetic of the present invention is preferably less than about 60 Angstroms, more preferably less than about 45 Angstroms, more preferably less than about 30 Angstroms, or more preferably less than about 15 Angstroms.

Figure 13:
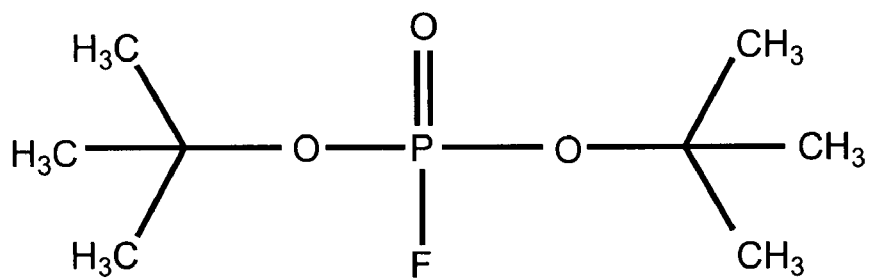
FIG. 13 illustrates the structure of serine protease inhibitor, diisopropyl fluorophosphate.
Figure 14:
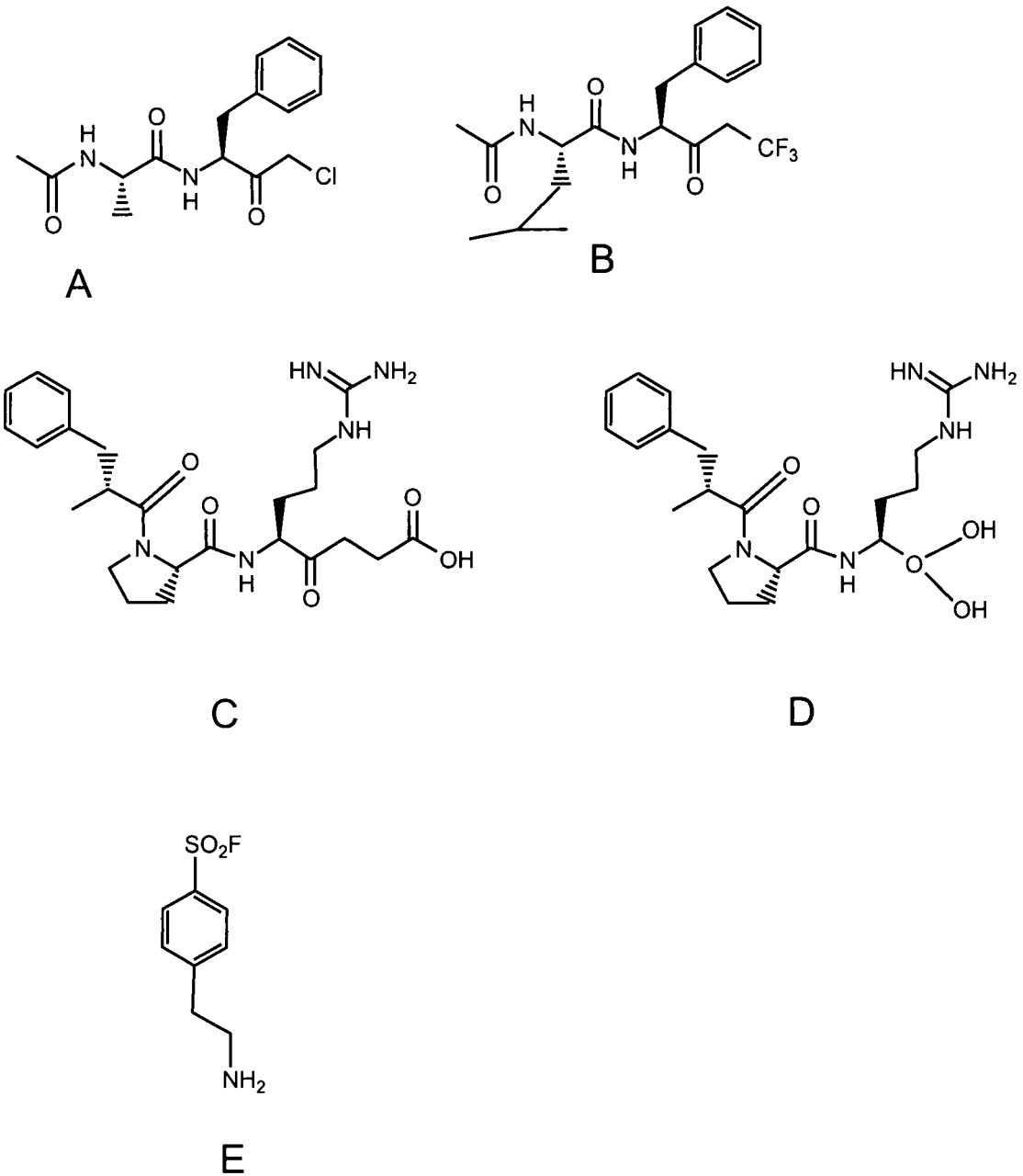
FIGS. 14A-14E illustrate structures of exemplary serine protease inhibitors A-E.

In some embodiments, an achaogen is a protease inhibitor, or more preferably a serine protease inhibitor. It is believed that LexA and UmuD are serine-lysine diad proteases that undergo proteolysis reactions that are critical for the induction of mutation in multiple bacterial species. See Roland, K L, et al. J. Biol. Chem. (1990) 265:12828-12835; Little, J W. J. Bacteriol. (1993) 175:4943-4950; Kim, B, et al. Cell 1993, 73:1165-1173; and Slilaty, S N, Prot. Engineer. (1991) 4:919-922. The catalytic residues of LexA (Ser119 and Lys156) catalyze the peptidase reaction in a manner similar to that of serine proteases. See Roland, K. L., J. Biol. Chem. (1990) 265, 12828-12835. Moreover, it has been shown that the serine protease inhibitor, diisopropyl fluorophosphates (DFP), inhibits auto-cleavage of LexA and that Ser119 was the only serine residue to react with DFP. See Roland, K L., J. of Biol. Chem., (1990) 265(22):12828-12835. (Structure of DFP is illustrated in FIG. 13.). However, these are but a few examples of achaogens and in some embodiments an achaogen is one other than a protease inhibitor or a serine protease inhibitor.

Thus, in some embodiments, an achaogen that comprises, consists essentially of, or consists of a protease inhibitor or a serine protease inhibitor or analog thereof preferably reduces the rate of induced mutations by at least a significant amount, e.g., at least 2%, 5%, 10%, 20%, 30%, 40%, 50%, 60%, 70%, 80%, 90%, or more. Methods of detecting levels of induced mutations are disclosed herein or are known in the art.

Examples of serine protease inhibitors that may be achaogens include DFP (diisopropyl fluorophosphates, a small molecule), AEBSF (aminoethyl-benzene sulfonyl fluoride), aprotinin (trypsin inhibitor from bovine lung), antipain, antithrombin III (e.g., from human plasma), (alpha)1-antitrypsin, APMSF (4-amidinophenyl-methane sulfonyl-fluoride), chymostatin, leupeptin-hemisulfate, Pefabloc S C (4-(2-aminoethyl)-benzenesulfonyl fluoride), PMSF (phenylmethyl sulfonyl fluoride), phosphoramidon, TLCK (1-chloro-3-tosylamido-7-amino-2-heptanone), TPCK (1-chloro-3-tosylamido-4-phenyl-2-butanone), and trypsin inhibitor from soybean. Additional examples of serine protease inhibitors contemplated by the present invention are depicted in FIGS. 14A-14E.

Achaogens that are serine protease inhibitors can be optimized using methods similar to those used to successfully design inhibitors of thrombin, factor Xa, elastase, tryptase, complement convertase, and hepatitis C—NS3 protease. See Vacca, J. P. Annu. Rep. Med. Chem. (1998) 33, 81-90; Verstraete, M. Haemostasis (1996) 26; Morishima, Y., Thromb. Haemost. (1997) 78, 1366-1371; Edwards, P. D., Med. Res. Rev. (1994) 14; and Rice, K. D., Curr. Pharm. Des. (1998) 4, 381-396; Oda, M., *Jpn. J. Pharmacol.* (1990) 52, 23-34; Steinkuhler, C., *Biochemistry* (1998) 37, 8899-8905; and Linas-Brunet, M., et al. *Bioorg. Med. Chem. Lett.* (1998) 8, 1713-1718.

Achaogens that comprise, consist essentially of, or consist of a protease inhibitor or serine protease inhibitor can be naturally occurring or synthetic. In one embodiment, an achaogen comprises, consists essentially of, or consists of an organic molecule that is a protease inhibitor. In particular, in some embodiments an achaogen can include a heterocyclic molecules that can act as protease inhibitors. By way of example only, an achaogen of the present invention can include a heterocyclic compounds having the general structure of Formula (I):

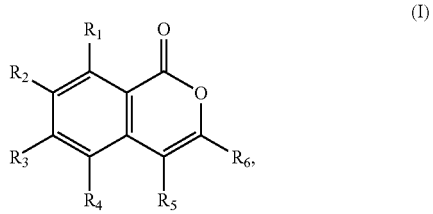

(I)

where $R_1$, $R_2$, $R_3$, $R_4$, $R_5$, and $R_6$ are each independently selected from the group consisting of $—(CHR_a)_x-L-R_b$, where x is selected from the group consisting of 0, 1, 2, 3, or 4; L is a single bond or —C(O)—, —NHC(O)—, —OC(O)—, —S(O)$_j$, where j is 0, 1, or 2; $R_a$ is a moiety selected from the group consisting of H, $(C_1-C_6)$alkyl, halogen, $(C_1-C_6)$fluoroalkyl, $(C_1-C_6)$alkoxy, —C(O)OH, —C(O)—NH$_2$, —$(C_1-C_6)$alkylamine, —C(O)—$(C_1-C_6)$alkyl, —C(O)—$(C_1-C_6)$fluoroalkyl, —C(O)—$(C_1-C_6)$alkylamine, and —C(O)—$(C_1-C_6)$alkoxy; and Rb is H, OH, halogen, NH$_2$, CN, N$_3$, or a moiety, optionally substituted with 1-3 independently selected substituents, selected from the group consisting of alkyl, alkenyl, alkoxy, mercaptyl, alkylamine, alkynyl, aryl, cycloalkyl, cycloalkenyl, and a heterocycle; in addition, $R_1$ and $R_2$, $R_2$ and $R_3$, $R_3$ and $R_4$, and $R_5$ and $R_6$, can optionally form a substituted or unsubstituted ring structure. Compounds having the structure of Formula (I) are also known as isocoumarins. The ability of compounds to act as achaogens, including compounds having the structure of Formula (I), as well as other heterocyclic protease inhibitors, other protease inhibitors, and other organic compounds, can be ascertained using the methods and techniques described herein.

Compounds of Formula (I) may be synthesized using standard synthetic techniques known to those of skill in the art or using methods known in the art in combination with methods described herein. In addition, several of the compounds of Formula (I) may be purchased from various commercial suppliers. As a further guide the following synthetic methods may be utilized.

Selected examples of covalent linkage products and precursor functional groups (i.e., a nucleophile and an electrophile) which yield them are given in the Table entitled "Examples of Covalent Linkages and Precursors Thereof." Precursor functional groups are shown as electrophilic groups and nucleophilic groups. The functional group on the organic substance may be attached directly, or attached via any useful spacer or linker. Thus, Table 2 may be utilized to synthesize or add further functionality to a precursor compound in order to synthesize additional compounds having the structure of Formula (I). For example, (a) an isocoumarin bearing an alkyl halide group can react with another compound having a thiol group in order to form an isocoumarin having a thioether group; (b) an isocoumarin having an amine group can react with a compound having an aryl halide group to form an isocoumarin having an aryl amine group; or (c) an isocoumarin having a carboxylic acid group can react with a compound having a hydrazide group to form an isocoumarin having a hydrazine group.

TABLE 2

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Covalent Linkage Product | Electrophile | Nucleophile |
| Carboxamides | carboxylic acids | amines/anilines |
| Esters | carboxylic acids | Alcohols |
| Hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |

TABLE 2-continued

Examples of Covalent Linkages and Precursors Thereof

| Covalent Linkage Product | Electrophile | Nucleophile |
|---|---|---|
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In some embodiments, a compound of Formula (I) can include a protecting group. The term "protecting group" refers to chemical moieties that block at least some reactive moieties and prevent such groups from participating in chemical reactions until the protective group is removed (or "cleaved"). In one aspect, a particular reagent bears at least three different functional groups and the desired product is synthesized by reacting only one of those three functional groups. Such a desired product may be made by protecting the two functional groups that are not supposed to be modified, thus leaving the third functional group available for further reaction. Once this further reaction has occurred, the other two functional groups may be restored by cleaving the protecting groups. The resulting compound has thus been modified at only one of the three potential sites.

Protective groups that are cleaved under disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester derivatives as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd0-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Examples of blocking/protecting groups may be selected from:

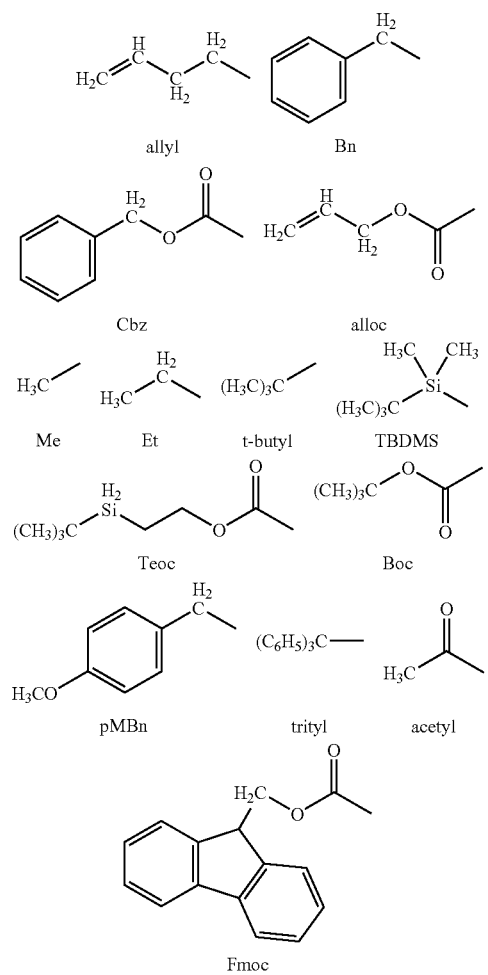

Other protecting groups are described in Greene and Wuts, Protective Groups in Organic Synthesis, 3rd Ed., John Wiley & Sons, New York, N.Y., 1999, which is incorporated herein by reference in its entirety.

Any of the achaogens presented herein may possess one or more chiral centers and each center may exist in the R or S configuration. The achaogens presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns. It ill be appreciated that the invention herein is not limited to any given compound herein and that, in certain embodiments, the achaogen of interest is a molecule other than a compound of Formula I as described herein.

The methods and formulations described herein can include the use of N-oxides, crystalline forms (also known as polymorphs), or pharmaceutically acceptable salts of achaogens having the structure of Formula (I), as well as active metabolites of these achaogens having the same type of activity. All tautomers are included within the scope of the achaogens presented herein. In addition, the achaogens described herein can exist in unsolvated as well as solvated forms with pharmaceutically acceptable solvents such as water, ethanol, and the like. The solvated forms of the compounds presented herein are also considered to be disclosed herein.

In some embodiments, an achaogen is other than a protease inhibitor, other than a serine protease inhibitor, other than a synthetic protease inhibitor, other than a naturally occurring protease inhibitor, other than a synthetic serine protease inhibitor, or other than a naturally occurring protease inhibitor.

The development of inhibitors against proteases similar to LexA and UmuD has been accomplished using established drug design methods. See Vacca, J P., *Annu. Rep. Med. Chem.* (1998) 33:81-90; Verstraete, M, *Haemostasis* (1996) 26 Suppl. 4: 70-77; Morishima, Y., *Thromb. Haemost.* (1997) 78:1366-1371; Edwards, P D, et al. *Med. Res. Rev.* (1994) 14(2): 127-94; Rice, K D, et al. *Curr. Pharm. Des.* (1998) 4:381-396; Oda, M, et al. *Jpn. J. Pharmacol.* (1990) 52:23-34; Steinkuhler, C., *Biochemistry*, (1998) 37:8899-8905; Llinas-Brunet, M., *Bioorg. Med. Chem. Lett.* (1998) 8:1713-1718; and Boger, D L., *Bioorg. Med. Chem. Lett.*, (2001) 11:1517-1520.

In some embodiments, an achaogen can be a naturally occurring agent or an analog of a naturally occurring agent that is a negative regulator of induced mutations. Examples of naturally occurring agents that are negative regulators of induced mutations include, but are not limited to, DinI, PsiB, ClpXP, Lon protease, and any fragments, homologs, or analogs thereof. These are but just a few examples of achaogens and in some embodiments; an achaogen is other than an isolated and/or purified DinI, PsiB, ClpXP, or a Lon protease. Also, in some embodiments, an achaogen is one other than a naturally occurring agent or an analog of a naturally occurring agent that acts as a negative regulator of induced mutations.

It is believed that chromosomally encoded DinI and F-Plasmid encoded PsiB bind to RecA and inhibit LexA auto-cleavage and/or UmuD cleavage. See McKenzie, G., *Proc. Natl. Aced. Sci. USA* (2000) 97, 6646-6651; Bagadasarian, M., et al., *Mol. Microbiol.* (1992) 6, 885-893; Yasuda, T., *EMBO J.* (1998) 17, 3207-3216. Experiments show that when released from repression by lexA deletion (in a sulA deletion background, required for survival) PsiB is capable of completely suppressing induced mutation even though the SOS response is fully induced. If under the same circumstances, psiB is also deleted, the hypermutable state is fully manifested. Furthermore, it is known that PsiB competes with both LexA and UmuD for binding to RecA, while DinI competes only with UmuD. See Yasuda, T., et al., *EMBO J.* 1998, 17:3207-3216; Yasuda, T., *EMBO* (2001) 20:1192-1202; and Bagadasarian, M., *Mol Microbiol.* (1992) 6:885-893.

Furthermore, induced mutation may be under negative regulation by proteases. For example, in bacteria induced mutation is negatively regulated or inhibited by one or more proteases, e.g., ClpXP and Lon proteases. See Frank, E, G., et al., *Proc. Ned. Aced. Sci. USA* (1996) 93, 10291-10296. Lon protease degrades $UmuD_2$ and UmuC proteins, while ClpXP specifically proteolyzes UmuD' of a UmuD'/UmuD heterodimer. These proteases are thought to ensure rapid exit from the hypermutable state once suitable mutations have been acquired.

Thus, in some embodiments an achaogen of the present invention may be an isolated and/or purified DinI, PsiB, ClpXP, Lon protease, or fragments, homologs, or analogs thereof. In particular, the present invention contemplates the use of peptidomimetics of DinI, PsiB, ClpXP, Lon protease, or any fragments, homologs or analogs thereof to reduce the rate of mutation in a cell or an organism. In other embodiments, an achaogen of the present invention is other than isolated and/or purified DinI, PsiB', ClpXP, Lon protease, or fragments, homologs, or analogs thereof.

In any of the embodiments herein, achaogens can be proteins or peptidomimetics of gene products that inhibit induced mutation (e.g., PsiB, DinI, ClpXP protease, Lon protease, and homologs thereof) modified for increased affinity for their target protein (e.g., RecA. LexA, or UmuD) by rational design or library-based selections or screens (for example, phage display or high-throughput screening). Achaogen peptide mimics may be designed based on the amino acid sequence of appropriate proteins or peptide fragments, modified for improved function, including improved target binding (for example, RecA or LexA in *E. coli*) or improved pharmacokinetics (for example, improved stability, cell permeability, or target specificity).

IV. Nucleic Acids

In some embodiments, an achaogen comprises or consists of a nucleic acid encoding a negative regulator of induced mutations. Examples of negative regulators of induced mutations include DinI, PsiB, ClpXP, Lon protease, and any fragments, homologs or analogs thereof. In preferred embodiments, such nucleic acids are isolated. These are but a few examples of the achaogens herein and in some embodiments an achaogen is one other than an isolated nucleic acid encoding DinI, PsiB, ClpXP, or Lon protease.

In some embodiments the present invention contemplates an achaogen comprising a phage particle wherein the phage particle's genome comprises of a nucleic acid encoding a negative regulator of induced mutations. For example, an achaogen of the present invention may be a bacteriophage whose genome encodes DinI, PsiB, ClpXP, Lon protease, or any fragments, homologs or analogs thereof. Preferably such phage is isolated. In addition, nucleic acid molecules that enhance the transcription and/or translation of PsiB or DinI are also contemplated by the invention herein. Phage and phagemids are but one example of the achaogens contemplated herein and in some embodiments an achaogen is one that does not include phage or a phagemid as described above.

In some embodiments, the present invention contemplates achaogens that bind to genes or regulators of genes that increase the rate of induced mutation (e.g., dinB, lexA, recA, recB, recC, recD, recF, recG, recN, polB, priA, ruvA, ruvB, ruvC, umuC, umuD, uvrA, uvrB, and uvrD). Such achaogens can include, for example, an antisense nucleic acid, a ribozyme, a zinc finger, an RNAi, or a triple helix nucleic acid the bind to or interact with a gene product that increases rate of mutation in a cell or an organism (e.g., RecA, RecB, RecC, RecD, RecF, RecG, RecN, LexA, UmuC, UmuD, PolB, PolIV, Poly, PriA, RuvA, RuvB, RuvC, UmuC, UmuD, UvrA, UvrB, UvrD, and any homolog or analogs thereof). When such an achaogen is introduced into a cell or an organism susceptible to or experiencing induced mutations, it can inhibit the rate of such induced mutations. The above embodiment is but one example of an achaogen and in some embodiments an achaogen is one other than a nucleic acid that specifically binds to a gene that increases the rate of induced mutation, or is one other than a nucleic acid that specifically binds to a nucleic acid encoding RecA, RecB, RecC, RecD, RecF, RecG, RecN, LexA, UmuC, UmuD, PolB, PolIV, Poly, PriA, RuvA, RuvB, RuvC, UmuC, UmuD, UvrA, UvrB, or UvrD or a nucleic acid complementary thereof.

In some embodiments, an achaogen can include, for example, a nucleic acid that encodes a negative regulator of the induced mutation system (e.g., psiB, dinI, lon, or clpXP protease) or any homolog, analog or negative regulator fragment thereof. This is but one example of an achaogen herein and in some embodiments an achaogen does not include a nucleic acid that encodes a negative regulator of induced mutagenesis or one or more of psiB, dinI, lon, and clpXP protease.

Any of the nucleic acids can be cloned (e.g., from a cDNA library), and inserted into a vector. Vectors may be constructed using methods, such as those disclosed in Sambrook, J. et al. "Molecular Cloning, A Laboratory Manual," (Cold Spring Harbor Press, Plainview, N.Y. 1989), and Ausubel, F. M. et al. "Current Protocols in Molecular Biology", (John Wiley & Sons, New York, N.Y., 1989), are incorporated herein by reference for all purposes. Vectors may be used to produce desired gene product(s) (e.g., PsiB, DinI, Lon protease, and ClpXP protease) by inserting an expression cassette into the vector, which includes a promoter and/or start codon and/or a regulatory sequence. Expression cassettes and regulatory sequences may be selected based on the host cell. An expression vector of the present invention may be used to transfer a host cell. The host cell is then maintained under appropriate condition that will allow for the expression of the nucleic acids (e.g. psiB, dinI, lon, or clpXP).

The vectors herein may also be used for phage therapy. Methods for phage therapy are disclosed in U.S. Pat. No. 6,054,312, which is incorporated herein by reference for all purposes. In particular, the present invention contemplates the use of phage therapy as a means of importing and integrating exogenous nucleic acids into a bacterial cell. In some embodiments, a nucleic acid that encodes for a negative regulator of an induced mutation response (e.g., DinI, PsiB, ClpXP protease, or Lon protease, or any homolog thereof, or fragment thereof) is inserted into a phage plasmid, also known as phagemid. Phagemids combine features of plasmids and phages. Phagemids contain an origin of replication and packaging signal of the filamentous phage, as well as a plasmid origin of replication. Other elements that are useful for cloning and/or expression of foreign nucleic acid molecules are generally also present. Such elements include, without limitation, selectable genes, multiple cloning site, primer sequences. The phagemids may be packaged into phage particles upon rescue by a helper phage. As used herein, "phage particles" refers to particles containing either a phage genome or a phagemid genome. The particles may contain other molecules in addition to the phage genome and capsid proteins.

Many phage vectors and phagemids are commercially available. For example, the pEGFP vector series (Clontech; Palo Alto, Calif.), M13mp vectors (Pharmacia Biotech, Sweden), pCANTAB SE (Pharmacia Biotech), pBluescript series (Stratagene Cloning Systems, La Jolla, Calif.) and others may be used. Other vectors are available in the scientific community (see, e.g., Smith, in Vectors: A Survey of Molecular Cloning Vectors and their Uses, Rodriquez and Denhardt, eds., Butterworth, Boston, pp 61-84, 1988) or may be constructed using standard methods (Sambrook et al., Molecular Biology: A Laboratory Approach, Cold Spring Harbor, N.Y., 1989; Ausubel et al., Current Protocols in Molecular Biology, Greene Publishing, N.Y., 1994) guided by the principles discussed below In preferred embodiments, phage particles are used to deliver nucleic acids that encode gene products that inhibit induced mutation in a cell or an organism. For example, the phage can be administered to any organism affected by or susceptible to a bacterial infection. The use of phage technology to target bacterial cells is often referred to as phage therapy. One of the benefits of phage therapy is that phage are bacteria specific. Thus, while the bacteria are transfected with the exogenous nucleic acids, surrounding mammalian cells are not affected. Furthermore, phage is able to withstand harsh environments and conditions such as those common to the mammalian digestive tract; thus, they are suited for oral/systemic formulations and administration.

In any of the embodiments herein, nucleic acids herein can be inserted into vectors that can replicate in eukaryotic cells (e.g., mammalian cells). In preferred embodiments, such constructs include a transcription terminator sequence, a polyadenylation sequence, a splice donor and acceptor sites, and an enhancer. Other elements useful for expression and maintenance of the construct in mammalian cells or other eukaryotic cells may also be incorporated. Because portions of the constructs are produced in bacterial cells, elements that are necessary or enable propagation in bacteria are incorporated.

The promoter that controls expression of the transgene should be active or activatable in the targeted cell. The targeted cell may be mammalian, avian, plant, or the like. Applications of the present invention will involve transfection of mammalian cells, including human, canine, feline, equine, or the like. The choice of the promoter will depend in part upon the targeted cell type and the degree or type of control desired. Promoters that are suitable within the context of the present invention include, without limitation, constitutive, inducible, tissue specific, cell type specific, temporal specific, or event-specific.

Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), bovine papilloma virus promoter, and adenovirus promoter. In addition to viral promoters, cellular promoters are also amenable within the context of this invention. In particular, cellular promoters for the so-called 'housekeeping' genes are useful (e.g., beta-actin). Viral promoters are often stronger promoters than cellular promoters.

In any of the embodiments herein, a nucleic acid achaogen may be inserted into a viral vector. Viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acids (oligonucleotides) may be administered locally or systemically such that they are permanently incorporated into the genome of the targeted cells, (e.g., tumor cells). Alternatively the treatment may have to be repeated periodically. A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccine virus, adenovirus, herpes viruses including HSV and EBV, and retroviruses. Many gene therapy protocols in the prior art have employed disabled murine retroviruses.

V. Antibodies

An achaogen of the present invention can also include an antibody that specifically binds to and inactivates a gene product that increases the rate of mutation in a cell or an organism. Examples of such gene products include but are not limited to, LexA, Pol II, Pol IV, Pol V, RecA, RecN, UmuC, UmuD, UvrA, UvrB, UvrD, and any homologs, analogs and fragments thereof. In some embodiments, an antibody of the present invention specifically binds to LexA in its cleavable conformation. In some embodiments, an antibody of the present invention binds to RecA, RecB, RecC, RecD, RecF, RecG, Rec N, LexA, UmuC, UmuD, PolB, PolIV, PoIV, PriA, RuvA, RuvB, RuvC, UmuC, UmuD, UvrA, UvrB, UvrD in its activated conformation.

The antibodies useful herein can be whole antibodies, single-chain antibodies, and antigen-binding fragments thereof. Preferably the antibodies include, but are not limited to, Fab, Fab' and F(ab')2, Fd, single-chain Fvs (scFv), single-chain antibodies, disulfide-linked Fvs (sdFv) and fragments comprising either a VL or VH domain. An antibody herein can be polyclonal, monoclonal, chimeric, or humanized. The antibodies herein can be derived from any animal including birds and mammals. Preferably, an antibodyherein is derived from a murine, rabbit, goat, guinea pig, camel, horse, or chicken. More preferably, an antibody is from a human or has been humanized. The antibodies herein may be used to reduce mutation rate in a cell or an organism (whether prokaryotic or eukaryotic).

In some embodiments, an antibody of the present invention is generated using an epitope-bearing polypeptide wherein the epitope-bearing polypeptide comprises or consists of the active site or the cleavage site of LexA. For example, an epitope-bearing polypeptide can comprise or consist of SEQ ID NO: 1, 2, or 3 (VAAG, VAAGEPL, or VAAGEPLLAW). Generally speaking, an epitope-bearing polypeptide of the present invention is about 1-50 amino acids in length, more preferably about 2-40 amino acids in length, more preferably about 3-30 amino acids in length, more preferably about 4-25 amino acids in length, or more preferably 5-10 amino acids in length. In some embodiments, an epitope-bearing polypeptide of the present invention comprises a peptide sequence of LexA including Ser119 and/or Lys156 of LexA.

The antibodies herein can be prepared by any suitable method known in the art. For example, Jones et al., Nature (1986) 321: 522-525 discloses replacing the CDRs of a human antibody with those from a mouse antibody. Marx, Science (1985) 229:455-456 discusses chimeric antibodies having mouse variable regions and human constant regions. Rodwell, Nature (1989) 342:99-100 discusses lower molecular weight recognition elements derived from antibody CDR information. Clackson, Br. J. Rheumatol. (1991) 3052:36-39 discusses genetically engineered monoclonal antibodies, including Fv fragment derivatives single chain antibodies, fusion proteins chimeric antibodies and humanized rodent antibodies. Reichman et al., Nature (1988) 332:323-327 discloses a human antibody on which rat hypervariable regions have been grafted. Verhoeyen, et al., Science (1988) 239: 1534-1536 describes grafting of a mouse antigen binding site onto a human antibody.

In yet another embodiment, antibodies able to withstand expression in bacterial cells are introduced into bacteria using phage. Such antibodies could bind to and inactivate the function of bacterial genes required for induced mutation (e.g., RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD, and any homologs, analogs and fragments thereof).

In addition, those skilled in the art are enabled to design and produce peptidomimetics having binding characteristics similar or superior to the complementary determining region of the antibodies herein. Horwell et al., Bioorg. Med. Chem. (1996) 4: 1573; Liskamp et al., Recl. Trav. Chim. Pays—Bas1 (1994) 113; Gante et al., Angew. Chem. Int. Ed. Engl. (1994) 33:1699; Seebach et al., Helv. Chim. Acta (1996) 79:913). Accordingly, the present invention also contemplates analogs and peptidomimetics of the antibodies herein.

VI. Polymerase Inhibitors as Achaogens

In any of the embodiments herein, an achaogen can be used to modulate biochemical pathway(s) that induce mutations. Such biochemical pathway(s) comprise proteases, DNA binding proteins, helicases, DNA polymerases, as well as other proteins. See Goodman, M F: Error-prone repair DNA polymerases in prokaryotes and eukaryotes. *Annu Rev Biochem* 2002, 71:17-50; Nickoloff, J A, Hoekstra, M F (eds.) *DNA Damage and Repair* (Humana Press, Totowa, N.J., 1998). Thus, in some embodiments, an achaogen comprises a composition that specifically binds to and inhibits an activity of gene products that induces mutation, such as a gyrase, helicase, error prone DNA polymerase, etc. Examples of such gene products include: RecA, RecB, RecC, RecD, RecF, RecG, Rec N, LexA, UmuC, UmuD, PolB, PolIV, Poly, PriA, RuvA, RuvB, RuvC, UmuC, UmuD, UvrA, UvrB, UvrD, and any homologs, analogs, or mutation inducing fragments thereof.

The evolution of antibiotic resistance can also be prevented via the inhibition of the function of the inducible, non-replicative, mutation-causing polymerases. Such polymerases include Pol II, Pol IV and Pol V in *E. coli* or their functional analogs in other species (e.g., DnaE2 in MTb). In essence, the invention herein attempts to force bacteria into using a 'high fidelity' means of re-initiating DNA replication at a stalled replication fork. For example, methods that force the bacterium to use a 'high fidelity' replication pathways would reduce mutability and thus disfavor the evolution of antibiotic resistance. In *E. coli*, inactivation of Pol II, Pol IV or Pol V via gene disruption has been shown to result in a significant decrease in the emergence of ciprofloxacin resistance.

Inactivation of a single mutation-causing polymerase (i.e., DnaE2) in MTb weakens the induced mutational response required for the evolution of resistance to rifampicin in vitro and in vivo. See Boshoff, H I M, Reed, M B., *Cell* (2003) 113:183-193. However, it is likely that other mutation-causing polymerases continue to function to facilitate resistance. Hence, in a preferred embodiment, the function of many or all mutation-causing polymerases is inhibited simultaneously, either by inhibiting their production (at the level of gene regulation as described above via the inhibition of LexA proteolysis) or their function (at the level of polymerase enzymatic activity). Due to the relaxed selectivity within the mutation-causing polymerase active sites, and further due to the inability of these error-prone enzymes to remove nucleotide miss-pairs via an enzymatic 3' to 5' exonuclease activity, these polymerases will recognize, incorporate, and not remove nucleoside analogs rejected by the replicative polymerases. Therefore, nucleoside analogs (e.g., dideoxy nucleosides with modified nucleobases or sugar rings) could selectively inhibit these mutation-causing polymerases while not inhibiting higher fidelity polymerases. In one embodiment, a single inhibitor that inhibits multiple mutation-causing polymerases can be used, resulting in a far stronger suppression of mutation than could be achieved via the inhibition of a single error-prone polymerase.

Thus, the present invention relates to compositions and methods that inhibit DNA polymerases, more preferably inducible DNA polymerase II, IV, and/or V, or more preferably inducible DNA polymerase IV and/or V. Such compositions (e.g., achaogens) include small molecules, antisense nucleic acids, polypeptides, glycopeptides, lipids, dideoxy-nucleotides, and mimetics, derivatives or variants thereof that can bind the above polymerases, thus inhibiting their enzymatic activity, bind to the above polymerase transcript, thus blocking translation.

In any of the embodiments herein, an achaogen reduces the rate of mutation in a cell or an organism by at least 2 fold, more preferably by at least 3 fold, more preferably by at least 4 fold, or more preferably by at least 5 fold. In any of the embodiments herein, an achaogen reduces the rate of mutation in a cell or an organism by at least 2%, 5%, 10%, 20%, 50%, 60%, 70%, 80%, 90%, or a greater percent than the rate of mutation without the achaogen.

Also, in some embodiments, an achaogen inhibits the acquisition of at least 1, 2, 3, 4, 5, 6, 7, 8, 9, 10, 20, 30, 40, 50, 60, 70, 80, 90 or 100 substitution mutations. In some embodiments, an achaogen inhibits the occurance of at least 1, 2, 3, 4, 5, 6, 7, 8, 9, 10, 20, 30, 40, 50, 60, 70, 80, 90 or 100 deletion/insertion mutations.

VII. Pharmaceutical Formulations

The present invention contemplates pharmaceutical formulations comprising an achaogen in an effective amount to achieve a therapeutic or prophylactic effect and a pharmaceutically effective carrier.

The actual effective amount will depend upon the condition being treated, the route of administration, the drug treatment used to treat the condition, and the medical history of the patient. Determination of the effective amount is well within the capabilities of those skilled in the art. The effective amount for use in humans can be determined from animal models. For example, a dose for humans can be formulated to achieve circulating concentrations that have been found to be effective in animals. The effective amount of an achaogen can vary if the achaogen is coformulated with another therapeutic agent (e.g., an antibiotic, an antineoplastic agent, an antiviral agent, an antiprotozoan agent, etc.). It is contemplated that lower dosages will be needed in such cases as a result of a synergistic effect of both active ingredients.

Preferably, an effective amount of an active ingredient (e.g., an achaogen or second therapeutic agent) is from about 0.0001 mg to about 500 mg active agent per kilogram body weight of a patient, more preferably from about 0.001 to about 250 mg active agent per kilogram body weight of the patient, still more preferably from about 0.01 mg to about 100 mg active agent per kilogram body weight of the patient, yet still more preferably from about 0.5 mg to about 50 mg active agent per kilogram body weight of the patient, and most preferably from about 1 mg to about 15 mg active agent per kilogram body weight of the patient. In terms of weight percentage, a pharmaceutical formulation of an active agent (e.g., an achaogen or second therapeutic agent) preferably comprises of an amount from about 0.0001 wt. % to about 10 wt. %, more preferably from about 0.001 wt. % to about 1 wt. %, and more preferably from about 0.01 wt. % to about 0.5 wt. %.

In any of the formulations herein, the achaogen can be formulated as a salt, a prodrug, or a metabolite. Such formulations can also include an additional therapeutic agent(s) such as an antibiotic, an antiviral agent, an antifungal agent, an antiprotozoan agent, and/or an antineoplastic agent.

Examples of antibiotics that may be coformulated with an achaogen include aminoglycosides, carbapenems, cephalosporins, cephems, glycopeptides, fluoroquinolones/quinolones, macrolides, oxazolidinones, penicillins, streptogramins, sulfonamides, and tetracyclines.

Aminoglycosides are a group of antibiotics found to be effective against gram-negative. Aminoglycosides are used to treat complicated urinary tract infections, septicemia, peritonitis and other severe intra-abdominal infections, severe pelvic inflammatory disease, endocarditis, mycobacterium infections, neonatal sepsis, and various ocular infections. They are also frequently used in combination with penicillins and cephalosporins to treat both gram-positive and gram-negative bacteria. Examples of aminoglycosides include amikacin, gentamycin, tobramycin, netromycin, streptomycin, kanamycin, paromomycin, and neomycin.

Carbapenems are a class of broad spectrum antibiotics that are used to fight gram-positive, gram-negative, and anaerobic microorganisms. Carbapenems are available for intravenous administration, and as such are used for serious infections which oral drugs are unable to adequately address. For example, carbapenems are often used to treat serious single or mixed bacterial infections, such as lower respiratory tract infections, urinary tract infections, intra-abdominal infections, gynecological and postpartum infections, septicemia, bone and joint infections, skin and skin structure infections, and meningitis. Examples of carbapenems include imipenem/cilastatin sodium, meropenem, ertapenem, and panipenem/betamipron.

Cephalosporins and cephems are broad spectrum antibiotics used to treat gram-positive, gram-negative, and spirochaetal infections. Cephems are considered the next generation cephalosporins with newer drugs being stronger against gram negative and older drugs better against gram-positive. Cephalosporins and cephems are commonly substituted for penicillin allergies and can be used to treat common urinary tract infections and upper respiratory infections (e.g., pharyngitis and tonsillitis). Cephalosporins and cephems are also used to treat otitis media, some skin infections, bronchitis, lower respiratory infections (pneumonia), and bone infection (certain members), and are a preferred antibiotic for surgical prophylaxis. Examples of cephalosporins include cefixime, cefpodoxime, ceftibuten, cefdinir, cefaclor, cefprozil, loracarbef, cefadroxil, cephalexin, and cephradineze. Examples of cephems include cefepime, cefpirome, cefataxidime pentahydrate, ceftazidime, ceftriaxone, ceftazidime, cefotaxime, cefteram, cefotiam, cefuroxime, cefamandole, cefuroxime axetil, cefotetan, cefazolin sodium, cefazolin, cefalexin.

Fluroquinolones/quinolones are antibiotics used to treat gram-negative infections, though some newer agents have activity against gram-positive bacteria and anaerobes. Fluroquinolones/quinolones are often used to treat conditions such as urinary tract infections, sexually transmitted diseases (e.g., gonorrhea, chlamydial urethritis/cervicitis, pelvic inflammatory disease), gram-negative gastrointestinal infections, soft tissue infections, pphthalmic infections, dermatological infections, sinusitis, and respiratory tract infections (e.g., bronchitis, pneumonia, and tuberculosis). Fluroquinolones/quinolones are used in combination with other antibiotics to treat conditions, such as multi-drug resistant tuberculosis, neutropenic cancer patients with fever, and potentially anthrax. Examples of fluoroquinolones/quinolones include ciproflaxacin, levofloxacin, and ofloxacin, gatifloxacin, norfloxacin, lomefloxacin, trovafloxacin, moxifloxacin, sparfloxacin, gemifloxacin, and pazufloxacin.

Glycopeptides and streptogramins represent antibiotics that are used to treat bacteria that are resistant to other antibiotics, such as methicillin-resistant *staphylococcus aureus* (MRSA). They are also be used for patients who are allergic to penicillin. Examples of glycopeptides include vancomycin, teicoplanin, and daptomycin.

Macrolides are broad spectrum antibiotics and are an important alternative to penicillins and cephalosporins. Macrolides are often used to treat respiratory tract infections (e.g., otitis media, chronic sinusitis, bronchitis, pharyngitis, pneumonia, tonsillitis, and strep throat), sexually transmitted diseases (e.g., nfections of the cervix and urinary tract, genital ulcer disease in men, syphilis), and opportunistic infections (e.g., pneumonia and *mycobacterium avium* complex (MAC) infection). Examples of macrolides include erythromycin, clarithromycin, azithromycin, axithromycin, dirithromycin, troleandomycin, oleandomycin, roxithromycin, and telithromycin.

Oxazolidinones are commonly admisntered to treat gram-positive infections. Carbapenems are used to treat gram-positive, gram-negative, and/or anaerobes. Oxazolidinones are commonly used as an alternative to other antibiotic classes for bacteria that have developed resistance. Examples of oxazolidinones include linezolid.

Penicillins are broad spectrum used to treat gram-positive, gram-negative, and spirochaetal infections. Conditions that are often treated with penicillins include pneumococcal and meningococcal meningitis, dermatological infections, ear infections, respiratory infections, urinary tract infections, acute sinusitis, pneumonia, and lyme disease. Examples of penicillins include penicillin, amoxicillin, amoxicillin-clavulanate, ampicillin, ticarcillin, piperacillin-tazobactam, carbenicillin, piperacillin, mezocillin, benzathin penicillin G, penicillin V potassium, methicillin, nafcillin, oxacillin, cloxacillin, and dicloxacillin.

Streptogramins are antibiotics developed in response to bacterial resistance that diminished effectiveness of existing antibiotics. Streptogramins are a very small class of drugs and are currently very expensive. Examples of streptogramins include quinupristin/dafopristin and pristinamycin.

Sulphonamides are broad spectrum antibiotics that have had reduced usage due to increase in bacterial resistance to them. Suphonamides are commonly used to treat recurrent attacks of rheumatic fever, urinary tract infections, prevention of infections of the throat and chest, traveler's diarrhea, whooping cough, meningococcal disease, sexually transmitted diseases, toxoplasmosis, and rhinitis. Examples of sulfonamides include co-trimoxazole, sulfamethoxazole trimethoprim, sulfadiazine, sulfadoxine, and trimethoprim.

Tetracyclines are broad spectrum antibiotics that are often used to treat gram-positive, gram-negative, and/or spirochaetal infections. Tetracyclines are often used to treat mixed infections, such as chronic bronchitis and peritonitis, urinary tract infections, rickets, chlamydia, gonorrhea, lyme disease, and periodontal disease. Tetracyclines are an alternative therapy to penicillin in syphilis treatment and are also used to treat acne and anthrax. Examples of tetracyclines include tetracycline, demeclocycline, minocycline, and doxycycline.

Other antibiotics contemplated herein (some of which may be redundant with the list above) include abrifam; acrofloxacin; aptecin, amoxicillin plus clavulonic acid; amikacin; apalcillin; apramycin; astromicin; arbekacin; aspoxicillin; azidozillin; azithromycin; azlocillin; aztreonam; bacitracin; benzathine penicillin; benzylpenicillin; clarithromycin, carbencillin; cefaclor; cefadroxil; cefalexin; cefamandole; cefaparin; cefatrizine; cefazolin; cefbuperazone; cefcapene; cefdinir; cefditoren; cefepime; cefetamet; cefixime; cefmetazole; cefminox; cefoperazone; ceforanide; cefotaxime; cefotetan; cefotiam; cefoxitin; cefpimizole; cefpiramide; cefpodoxime; cefprozil; cefradine; cefroxadine; cefsulodin; ceftazidime; ceftriaxone; cefuroxime; cephalexin; chloramphenicol; chlortetracycline; ciclacillin; cinoxacin; ciprofloxacinfloxacin; clarithromycin; clemizole penicillin; cleocin, cleocin-T, clindamycin; cloxacillin; corifam; daptomycin; daptomycin; demeclocycline; desquinolone; dibekacin; dicloxacillin; dirithromycin; doxycycline; enoxacin; epicillin; erthromycin; ethambutol; gemifloxacin; fenampicin; finamicina; fleroxacin; flomoxef; flucloxacillin; flumequine; flurithromycin; fosfomycin; fosmidomycin; fusidic acid; gatifloxacin; gemifloxaxin; gentamicin; imipenem; imipenem plus cilistatin combination; isepamicin; isoniazid; josamycin; kanamycin; kasugamycin; kitasamycin; kalrifam, latamoxef; levofloxacin, levofloxacin; lincomycin; linezolid; lomefloxacin; loracarbaf; lymecycline; mecillinam; meropenem; methacycline; methicillin; metronidazole; mezlocillin; midecamycin; minocycline; miokamycin; moxifloxacin; nafcillin; nafcillin; nalidixic acid; neomycin; netilmicin; norfloxacin; novobiocin; oflaxacin; oleandomycin; oxacillin; oxolinic acid; oxytetracycline; paromycin; pazufloxacin; pefloxacin; penicillin g; penicillin v; phenethicillin; phenoxymethyl penicillin; pipemidic acid; piperacillin; piperacillin and tazobactam combination; piromidic acid; procaine penicillin; propicillin; pyrimethamine; rifadin; rifabutin; rifamide; rifampin; rifamycin sv; rifapentene; rifomycin; rimactane, rofact; rokitamycin; rolitetracycline; roxithromycin; rufloxacin; sitafloxacin; sparfloxacin; spectinomycin; spiramycin; sulfadiazine; sulfadoxine; sulfamethoxazole; sisomicin; streptomycin; sulfamethoxazole; sulfisoxazole; quinupristan-dalfopristan; teicoplanin; telithromycin; temocillin; gatifloxacin; tetracycline; tetroxoprim; telithromycin; thiamphenicol; ticarcillin; tigecycline; tobramycin; tosufloxacin; trimethoprim; trimetrexate; trovafloxacin; vancomycin; verdamicin; azithromycin; and linezolid.

Examples of antineoplastic agents that may be coformulated with an achaogen include: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine; hydrochloride; elsamitrucin; enloplatin; enpromate; epipropidine; epirubicin hydrochloride; erbulozole; esorubicin hydrochloride; estramustine; estramustine phosphate sodium; etanidazole; ethiodized oil; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; imofosine; interferon alpha-2a; interferon alpha-2b; interferon alpha-n1; interferon alpha-n3; interferon beta-Ia; interferon gamma-Ib; iproplatin; irinotecan hydrochloride; lanreotide acetate; letrozole; leuprolide acetate liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycinl; spirogermanium hydrochloride; spiromustine; spiroplatin; streptonigrin; streptozocin; strontium chloride sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; tiazofurin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride. Additional antineoplastic agents that are disclosed herein or known in the art are also contemplated by the present invention.

A "pharmaceutical acceptable carrier" is a pharmaceutically acceptable solvent, suspending agent or vehicle for delivering an achaogen of the present invention to an animal or human. The carrier may be, for example, gaseous, liquid or solid and is selected with the planned manner of administration in mind.

Examples of pharmaceutically acceptable carriers for oral pharmaceutical formulations include: lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also preferred carriers.

Examples of pharmaceutically acceptable carriers for topical formulations include: ointments, cream, suspensions, lotions, powder, solutions, pastes, gels, spray, aerosol or oil. Alternately, a formulation may comprise a transdermal patch or dressing such as a bandage impregnated with an active ingredient (e.g., achaogen and/or second therapeutic agent) and optionally one or more carriers or diluents. The topical formulations may include a compound that enhances absorption or penetration of the active ingredient through the skin or other affected areas. Examples of such dermal penetration enhancers include dimethylsulfoxide and related analogues.

To be administered in the form of a transdermal delivery system, the dosage administration will be continuous rather than intermittent throughout the dosage regimen.

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. Extemporaneous injection solutions and suspensions may be prepared from sterile powders, granules and tablets of the kind previously described. Parenteral and intravenous formulation may include minerals and other materials to make them compatible with the type of injection or delivery system chosen.

Commonly used pharmaceutically acceptable carriers for parenteral administration includes, water, a suitable oil, saline, aqueous dextrose (glucose), or related sugar solutions and glycols such as propylene glycol or polyethylene glycols. Solutions for parenteral administration preferably contain a water soluble salt of the active ingredient, suitable stabilizing agents and, if necessary, buffer substances. antioxidizing agents, such as sodium bisulfite, sodium sulfite, or ascorbic acid, either alone or combined, are suitable stabilizing agents. Citric acid salts and sodium EDTA may also be used as carriers. In addition, parenteral solutions may contain preservatives, such as benzalkonium chloride, methyl- or propylparaben, or chlorobutanol. Suitable pharmaceutical carriers are described in Remington, cited above.

The present invention additionally contemplates achaogens formulated for veterinary administration by methods conventional in the art.

The achaogens described herein can also be formulated for industrial applications with, for example, a cleaning product, such as soap, laundry detergent, shampoo, dishwashing soap, toothpaste, and other house cleaning detergents.

VIII. Administration

The compositions and pharmaceutical formulation herein can be administered to an organism by any means known in the art. Routes for administering the compositions and pharmaceutical formulations herein to an animal, such as a human, include parenterally, intravenously, intramuscularly, orally, by inhalation, topically, vaginally, rectally, nasally, buccally, transdermally, or by an implated reservoir external pump or catheter. When administered to a plan, such means can be by spray or via irrigation.

Although any route of administration may be used, parenteral administration, i.e., administration by injection, is preferred. Injectable formulations can be prepared in conventional forms, either as liquid solutions or suspensions; as solid forms suitable for solubilization or suspension in liquid prior to injection; or as emulsions. Preferably, sterile injectable suspensions are formulated according to techniques known in the art using suitable pharmaceutically acceptable carriers and other optional components as discussed above.

Parenteral administration may be carried out in any number of ways, but it is preferred that the use of a syringe, catheter, or similar device, be used to effect parenteral administration of the formulations described herein. The formulation may be injected systemically such that the active agent travels substantially throughout the entire bloodstream.

Also, the formulation may also be injected locally to a target site, e.g., injected to a specific portion of the body for which inhibition of mutagenesis is desired. An advantage of local administration via injection is that it limits or avoids exposure of the entire body to the active agent(s) (e.g., achaogens and/or other therapeutic agents). It must be noted that in the present context, the term local administration includes regional administration, e.g., administration of a formulation directed to a portion of the body through delivery to a blood vessel serving that body zone. Local delivery may be direct, e.g., intratumoral. Local delivery may also be nearly direct, i.e., intralesional or intraperitoneal, that is, to an area that is sufficiently close to a tumor or site of infection so that the active agent(s) exhibit the desired pharmacological activity. Thus, when local delivery is desired, the pharmaceutical formulations are preferably delivered intralesionally, intratumorally, or intraperitoneally.

It is intended that, by local delivery of the presently described pharmaceutical formulations, a higher concentration of the active agent may be directed to the target site. There are several advantages to having high concentrations delivered directly at the target site. First, since the active agent is more localized, there is less potential for toxicity to the patient since minimal systemic exposure occurs. Second, drug efficacy is improved since the target site is exposed to higher concentrations of the drug. Third, relatively fast delivery minimizes solubility and stability liabilities of the active agent before reaching its target site.

Preferably the pharmaceutical compositions are in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet, or it can be the appropriate number of any of these packaged forms.

Useful pharmaceutical dosage formulations for administration of the compounds of the present invention are illustrated as follows:

Capsules: A large number of unit capsules are prepared by filling standard two-piece hard gelatin capsules each with 1-100 milligrams of powdered active ingredient, 150 milligrams of lactose, 50 milligrams of cellulose, and 6 milligrams magnesium stearate.

Soft Gelatin Capsules: A mixture of active ingredient in a digestible oil such as soybean oil, cottonseed oil or olive oil is prepared and injected by means of a positive displacement pump into gelatin to form soft gelatin capsules containing 1-100 milligrams of the active ingredient. The capsules are washed and dried.

Tablets: A large number of tablets are prepared by conventional procedures so that the dosage unit was 1-100 milligrams of active ingredient, 0.2 milligrams of colloidal silicon dioxide, 5-6 milligrams of magnesium stearate, 275 milligrams of microcrystalline cellulose, 11 milligrams of starch and 98.8 milligrams of lactose. Appropriate coatings can be applied to increase palatability or delay absorption.

Injectable: A parenteral composition suitable for administration by injection is prepared by stirring 0.5-1.5% by weight of active ingredient in 10% by volume propylene glycol and water. The solution is made isotonic with sodium chloride and sterilized.

Suspension: An aqueous suspension is prepared for oral administration so that each 5 ml contains 1-100 mg of finely divided active ingredient, 200 mg of sodium carboxymethyl cellulose, 5 mg of sodium benzoate, 1 g of sorbitol solution, U.S.P., and 0.02 ml of vanillin.

Achaogens of the present invention may be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Achaogens of the present invention may be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of the drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Achaogens can be administered to any organism (eukaryotic or prokaryotic) to prevent or treat drug resistance. Achaogens can also be administered to a first organism in order to target a second organism associated with the first organism. For example, an achaogen can be administered to a mammal infected by bacteria or to a plant infected by a fungus.

Achaogens can be administered as a monotherapy or in combination with a second therapeutic agent (e.g., antibiotic, antiviral, antifungal, antiprotozoan, antineoplastic agent). When administered as part of a combination therapy, the achaogens herein can be administered serially or simultaneously with the second agent. In some embodiments, an achaogen is administered prior to the administration of a second therapeutic agent. In other embodiments, an achaogen is administered after the administration of a second therapeutic agent.

For example, for prophylactic benefit, an achaogen and antibiotic may be co-administered to a patient at risk of developing a bacterial infection that could become antibiotic resistant. In some embodiments, the achaogen is administered prior to the administration of the antibiotic.

IX. Screening to Identify Gene Products Associated with Mutation

If a gene product is involved in induced mutation, its function increases a cell's ability to mutate. Inactivation of that gene product decreases a cell's ability to mutate. These principles can be used to determine if a given gene product is indeed mutation-causing and thus a potential drug target, the inhibition of which suppresses induced mutation and the development of drug (e.g., antibiotic) resistance.

In one embodiment, a test gene is genetically inactivated using known gene disruption techniques. After such a disruption event, the locus that encoded the putatively mutation-causing target would now be unable to produce the gene product and the cell would lack the function of that gene product. Various known 'mutability' assays are used to assess the effect of the gene disruption event on a cell's mutability. See Friedberg, E C, Walker, G C, Siede, W. *DNA Repair and Mutagenesis* (ed. Friedberg, E. C.) American Society of Microbiology, Washington D.C., 1995. For example, an adaptation of the so-called 'Stressful Lifestyle Associated Mutation' (or SLAM) assay (as described in example #2 and FIG. 2) wherein the evolution of resistance to an antibiotic of choice is measured) or a forward mutation or reversion assay can be used. See Bull, H J, Lombardo, M J, Rosenberg, S M: Stationary-phase mutation in the bacterial chromosome: recombination protein and DNA polymerase IV dependence. Bull H J., *Proc. Natl. Acad. Sci. USA* (2001) 98:8334-8341; Friedberg, E C. et al. DNA Repair and Mutagenesis (ed. Friedberg, E. C.) American Society of Microbiology, Washington D.C., 1995; Crouse, G F: *Methods* (2000) 22:116-119; Rosenberg, S M *Nature. Rev. Genet.* (2001) 2:504-515; Rosche, W A., *Methods* (2000) 20:4-17; and Foster, P L, *BioEssays* (2000) 22:1067-1074.

In another embodiment, a bacterial strain with an inactivated test gene and a non-functional reporter gene is used. Examples of reporter genes that can be used include the lacZ gene, green fluorescent protein gene, red fluorescent protein gene, and yellow fluorescent protein gene. The frequency at which the reporter gene is made functional (via a compensation mutation) in the presence of a wild-type test gene or an inactivated test gene is determined. A decrease in the frequency of restoration of function of the reporter gene in a cell containing an inactivated test gene indicates that the test gene has mutation-causing activity.

In yet another embodiment, bacterial cells with an inactivated test gene or a wild-type test gene are exposed to an antibiotic. The number of cells that develop resistance to the antibiotic is quantified in both cells with the inactive test gene and cells with the wild-type test gene. A decrease in the number of cells that develop antibiotic resistance in the case of the inactive test gene suggests that the test gene has potential mutation-causing activity.

Numerous techniques are known in the art to inactivate genes, many of which could be used to inactivate a test gene of interest. These techniques include the direct inactivation of the test gene, for example via mutation of the test gene via homologous recombination. Another useful technique is the indirect activation of the test gene, for example via mutation of a gene whose gene product modulates the activity of the test gene.

Typically, the test gene is inactivated via one or more mutations such that the resulting protein encoded by the test gene is inactive. Alternatively, the entire gene (or a large portion of the gene's open reading frame) is deleted from the genome. Mutation of the test gene may be carried out using numerous mutagenesis techniques known in the art. At the genetic level, the mutants ordinarily are prepared by site-directed mutagenesis of the DNA encoding the gene. The mutants can be substitution mutants, deletion mutants, or insertion mutants.

In some embodiments, an achaogen is an inhibitor or binding agent of a gene product that increases the rate of mutation in a cell or an organism (e.g., RecA, RecN, LexA, DinB, PolII, Pol IV, UmuC, UmuD, UvrA, UvrB, and UvrD). In particular, the present invention contemplates an achaogen that is an inhibitor and/or binding agent of LexA, RecA, or both. Methods for identifying binding agents are known in the art and include yeast two hybrid systems, etc.

X. Screening for Small Molecules that Inhibit Mutation

Achaogens can be identified by a number of methods including screening libraries of chemical compounds. Combinatorial libraries and methods for searching such libraries are known in the art and include: biological libraries, natural products libraries, spatially addressable parallel solid phase or solution phase libraries, synthetic library methods requiring deconvolution, the 'one-bead one-compound' library method, and synthetic library methods using affinity chromatography selection. The biological library approach is largely limited to polypeptide libraries, while the other four approaches are applicable to polypeptide, non-peptide oligomer or small molecule libraries of compounds. See Lam, K. S. (1997) *Anticancer Drug Des.* 12:145.

In one embodiment, achaogens are screened using Automated Ligand Identification System (referred to herein as "ALIS"). See, e.g., U.S. Pat. Nos. 6,721,665, 6,714,875, 6,694,267, 6,691,046, 6,581,013, 6,207,861, and 6,147,344, which are incorporated herein by reference for all intended purposes. ALIS is a high-throughput technique for the identification of small molecules that bind to proteins of interest (e.g., RecA or LexA). Small molecules found to bind tightly to a protein can then be tested for their ability to inhibit the biochemical activity of that protein.

Thus, in some embodiments, a target protein (e.g., RecA, LexA, or Pol V) is mixed with pools of small molecules. Preferably, more than 1,000 pools are used, more preferably more than 2,000 pools are used, more preferably more than 3,000 pools are used, or more preferably, more than 10,000 pools are used. Each pool contains approximately, 1,000 compounds, more preferably approximately 2,500 compounds, or more preferably approximately 5,000 compounds that are 'mass encoded,' meaning that their precise molecular structure can be determined using only their mass and knowledge of the chemical library.

The small molecules and proteins are mixed together and allowed to come to equilibrium (they are incubated together for 30 minutes at room temperature). The mixture is rapidly cooled to trap bound complexes and subject to rapid size exclusion chromatography (SEC). Small molecules that bind tightly to the protein of interest will be co-excluded with the protein during SEC. Mass spectroscopic analysis is performed to determine the masses of all small molecules found to bind the protein. Measurement of these masses allows for the rapid determination of the molecular structures of the small molecules.

Compounds that bind to a target protein (e.g., LexA and/or filamented RecA) in ALIS can then be tested for their ability to inhibit RecA-induced LexA proteolysis in vitro. Molecules with potent in vitro inhibitory properties can be tested using a modified Stressful Lifestyle Adaptation and Mutation (referred to herein as "SLAM") assays, described in Example #2 below, for achaogen activity (i.e., the ability to inhibit the emergence of ciprofloxacin resistant *E. coli* grown on ciprofloxacin-containing (35 ng/ml) LB agar growth media). Molecules with detectable achaogen activity in SLAM assays can be tested for achaogen activity in mouse thigh infection models.

In one embodiment, a chemical collection of compounds is screened in a format similar to the SLAM assay (from example #2 below) to identify molecules that decrease mutability. Bacterial cells are exposed to either one test compound or a library of compounds and the number of mutant cells generated over a period of time is determined in the presence and absence of the test compound. A decrease in the ratio of resistant cells to total cells indicates the achaogen activity of the test compound. The number of resistant cells generated is determined both before and after bacteria are exposed to the drug. The number of mutant cells is quantified using known assays, for example forward mutation, gene reversion, or SLAM assays. See Friedberg, E C, Walker, G C, Siede, W. DNA Repair and Mutagenesis (ed. Friedberg, E. C.) (American Society of Microbiology, Washington D.C., 1995); Crouse, G F., *Methods* (2000) 22:116-119. In yet another embodiment, the bacterial cells are exposed to a mutation-causing environment and the number of mutant cells generated is quantified in the presence and absence of the test compound. For example, a variation of the SLAM assay is used to proactively stress the bacteria (for example via exposure to UV radiation or chemical mutagens) so as to elevate mutation rates in bacteria. Such stress aids in the detection of achaogens that inhibit mutation due to the increased frequency of bacterial mutations.

In another example of a method to screen for achaogens, purified LexA protein, purified RecA protein, and ssDNA are exposed to test compounds. In the presence of ssDNA and nucleoside triphosphate, RecA is activated and binds to LexA and facilitates LexA's self-cleavage reaction. In the presence of an achaogen, the activation of RecA, its binding to LexA, or LexA's cleavage reaction will be inhibited. The decreased activation of RecA, the decreased binding of RecA to LexA, or the chemical inhibition of LexA's self-cleavage reaction can be evaluated by measuring the cleavage of LexA (e.g., by gel mobility assay, chromogenic assay, mass spectrometry, or cell-based GFP reporter assay). The inhibition of LexA cleavage indicates that the test compound is a potential achaogen.

A similar assay can also be designed with the purified UmuD gene product in order to find inhibitors of its cleavage that thus prevent production of functional Pol V. Similar assay can also be designed with purified RecB, RecC, RecD, RecF, RecG, RecN, UmuC, PolB, PolIV, Poly, PriA, RuvA, RuvB, RuvC, UmuC, UmuD, UvrA, UvrB, UvrD, and any homologs or fragments thereof.

The inhibition of different mutation-causing polymerases by potential achaogens can be quantified using standard methods. See Ogawa, A K,. *J Am Chem Soc* (2000) 122:3274-3287. For example, the rate of DNA synthesis with a given polymerase may be measured in the presence and absence of the potential achaogen using 5'-radiolabeled oligonucleotide primers resolved after the reaction by polyacrylamide gel electrophoresis and quantification by standard methods. Alternatively, high-throughput assays can be used to screen through large compound libraries to identify potential achaogens. Such assays rely on arraying the reaction mixtures in 96-well plates, where each well also contains a different achaogen. Fluorophore labeled nucleoside triphosphates or oligonucleotide primers or templates can be used in conjunction with standard plate handling and visualization procedures to determine which molecules effectively inhibited the activity of a given polymerase. In one embodiment, libraries can be screened in the presence of one or more of the inducible polymerases in order to identify achaogens that would most efficiently prevent mutation by inhibiting one or more polymerases simultaneously (for example, Pol IV and/or Pol V in *E. coli*).

Other methods of screening libraries of compounds for achaogens include screening for helicase inhibitors (e.g., RuvA, RuvB, RuvC, RecB, RecC, RecD inhibitors or combinations thereof, such as RuvABC and RecBC), inhibitors of reporter genes such as GFP or luciferase under the control of LexA regulated propomoters, or inhibitors that reduce the rate of evolution of drug resistance (or more preferably antibiotic resistance) in a SLAM assay as described herein.

XI. Structure-Based Design Methods to Create Small Molecule Achaogens

In some embodiments, one can use molecular modeling software tools to create realistic 3-D models of how molecules are shaped. Such methods include the use of, for example, molecular graphics (i.e., 3D representations) and computational chemistry (e.g., calculations of the physical and chemical properties).

Using molecular modeling, rational drug design programs can predict which of a collection of different drug like compounds may fit into the active site of an enzyme, and by computationally adjusting their bound conformation, decide which compounds actually might fit the active site well. See William Bains, Biotechnology from A to Z, 2nd edition, Oxford University Press, 1998, at 259.

For basic information on molecular modeling, see, e.g., M. Schlecht, Molecular Modeling on the PC, 1998, John Wiley & Sons; Gans et al., Fundamental Principals of Molecular Modeling, 1996, Plenum Pub. Corp.; N. C. Cohen (editor), Guidebook on Molecular Modeling in Drug Design, 1996, Academic Press; and W. B. Smith, Introduction to Theoretical Organic Chemistry and Molecular Modeling, 1996. U.S. patents which provide detailed information on molecular modeling include U.S. Pat. Nos. 6,093,573; 6,080,576; 5,612,894; 5,583,973; 5,030,103; 4,906,122; and 4,812,12.

The present invention permits the use of molecular and computer modeling techniques to design, and select compounds (e.g., achaogens) that bind to LexA (in its cleavable or non-cleavable form), RecA, Pol IV, Pol V or other gene products that increase the rate of induced mutagenesis. Thus, the invention enables the use of atomic coordinates deposited at the RCSB Protein Data Bank with the accession number PDB ID: 1AA, 1LEA, 1LEB to design compounds that interact with such gene products (e.g., LexA and/or RecA). For example, this invention enables the design of compounds that act as competitive inhibitors of LexA by binding to, all or a portion of, the active site involved in LexA self-cleavage or the RecA-LexA binding interface.

This invention also enables the design of compounds that act as uncompetitive inhibitors of RecA-induced LexA proteolysis. These inhibitors may bind to, all or a portion of, the active site of RecA and/or LexA. Similarly, non-competitive inhibitors that bind to either RecA and/or LexA and inhibit RecA and/or LexA (whether or not bound to another chemical entity) may be designed using the atomic coordinates of RecA and/or LexA of this invention.

Alternatively, the atomic coordinates provided by the present invention are useful in designing improved analogues of known gene products that inhibit induced mutation (e.g., DinI, PsiB, homologs thereof, and fragments thereof) or to design novel classes of inhibitors based on the LexA-RecA-binding complex. This provides a novel route for designing potent and selective inhibitors.

The availability of both protein crystals and of atomic coordinates determined by X-ray diffraction studies enables 'soaking' experiments with RecA and/or LexA crystals with molecules composed of a variety of different chemical entities to identify potential sites for interaction between candidate inhibitors and RecA and/or LexA. For example, high resolution X-ray diffraction data collected from crystals saturated with solvent allows the determination of where each type of solvent molecule binds the protein. Small molecules that bind tightly to those sites can then be tested for their ability to inhibit induced mutation (Travis, J., *Science* (1993) 262: 1374).

Moreover, the present invention enables computational screening of small molecule databases for chemical entities, agents, or compounds that can bind in whole, or in part, to RecA and/or LexA and, thereby prevent RecA-induced LexA proteolysis. In this screening technique, the quality of fit of such entities or compounds to the binding site may be judged either by shape complementarity or by estimated interaction energy. See Meng, E. C. et al., *J. Coma. Chem.*, 13: 505-524 (1992).

The design of compounds that bind to or inhibit RecA and/or LexA according to this invention generally involves consideration of two factors. First, the compound must be capable of physically associating with RecA, LexA, Pol IV, Pol V, or other protein required for induced mutation. Non-covalent molecular interactions important in the association of compounds with RecA, LexA, Pol IV, Pol V, or other protein required for induced mutation, include hydrogen bonding, van der Waals and hydrophobic interactions. Second, the compound must be able to assume a conformation that allows it to associate with RecA, LexA, Pol IV, Pol V, or other protein required for induced mutation. Although certain portions of the compound will not directly participate in this association with RecA, LexA, Pol IV, Pol V, or other protein required for induced mutation, those portions may still influence the overall conformation of the molecule. This, in turn, may have a significant impact on potency. Such conformational requirements include the overall three-dimensional structure and orientation of the chemical entity or compound in relation to all or a portion of the active site of RecA, LexA, Pol IV, Pol V, or other protein required for induced mutation or the spacing between functional groups of a compound comprising several chemical entities that directly interact with RecA, LexA, Pol IV, Pol V, or other protein required for induced mutation.

The potential inhibitory or binding effect of a chemical compound on induced mutation may be analyzed prior to its actual synthesis and by the use of computer modeling techniques. If the theoretical structure of the given compound precludes any potential association between it and RecA, LexA, Pol IV, Poly, or other protein required for induced mutation, synthesis and testing of the compound is obviated. However, if computer modeling suggests a strong interaction is possible, the molecule may then be synthesized and tested for its ability to interact with RecA, LexA, Pol IV, Poly, or other protein required for induced mutation and to thereby inhibit induced mutation. In this manner, synthesis of inactive compounds may be avoided.

One skilled in the art may use one of several methods to screen chemical entities fragments, compounds, or agents for their ability to associate with RecA, LexA, Pol IV, PolV, or other protein required for induced mutation and more particularly with the individual binding pockets of RecA, LexA, Pol IV, Pol V, or other protein required for induced mutation. This process may begin by visual inspection of, for example, the active site on the computer screen based on the RecA, LexA, Pol IV, Pol V, or other protein required for induced mutation coordinates deposited in the RCSB Protein Data Bank with the accession number PDB ID: 1AA3, ILEA, and ILEB. Selected chemical entities, compounds, or agents may then be positioned in a variety of orientations, or docked, within an individual binding pocket of RecA, LexA, Pol IV, Pol V, or other protein required for induced mutation as defined above. Docking may be accomplished using software such as Quanta and Sybyl, followed by energy minimization and molecular dynamics with standard molecular mechanics force fields, such as CHARMM or AMBER.

Specialized computer programs also assist in the process of selecting chemical entities. These include but are not limited to GRID (Goodford, P. J., *J. Med. Chem.*, (1985) 28, 849-857). GRID is available from Oxford University, Oxford, UK; MCSS (Miranker, A. et al., *Structure, Function and Genetics*, (1991) Vol. 11, 29-34), MCSS is available from Molecular Simulations, Burlington, Mass., AUTODOCK (Goodsell, D. S. and A. J. Olsen, "Automated Docking of Substrates to Proteins by Simulated Annealing" *Proteins: Structure. Function, and Genetics*, 8, 195-202 (1990)). AUTODOCK is available from Scripps Research Institute, La Jolla, Calif.; DOCK (Kuntz, I. D. et al., "A Geometric Approach to Macromolecule-Ligand Interactions" *J. Mol. Biol.*, (1982) 161, 269-288). DOCK is available from University of California, San Francisco, Calif.

Once suitable chemical entities, compounds, or agents have been selected, they can be assembled into a single compound or inhibitor. Assembly may proceed by visual inspection of the relationship of the fragments to each other on the three-dimensional image displayed on a computer screen in relation to the atomic coordinates of RecA, LexA, Pol IV, Pol V, or other protein required for induced mutation. This would be followed by manual model building using software such as Quanta or Sybyl.

Useful programs to aid one of skill in the art in connecting the individual chemical entities, compounds, or agents include but are not limited to CAVEAT (Bartlett, P. A. et al, "CAVEAT: A Program to Facilitate the Structure-Derived Design of Biologically Active Molecules". In Molecular Recognition in Chemical and Biological Problems", Special Pub., Royal Chem. Soc., 78, pp. 82-196 (1989)). CAVEAT is available from the University of California, Berkeley, Calif.; 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992); also HOOK (available from Molecular Simulations, Burlington, Mass.).

Instead of designing an inhibitor of a RecA, LexA, Pol IV, Pol V, or other protein required for induced mutation in a step-wise fashion one chemical moiety at a time as described above, inhibitors of RecA, LexA, Pol IV, Pol V may be designed as a whole or "de novo" using either an empty binding site or optionally including some portion(s) of known inhibitor(s). These methods include LUDI (Bohm, H.-J., "The Computer Program LUDI: A New Method for the De Novo Design of Enzyme Inhibitors", *J. ComR. Aid. Molec. Design*, (1992) 6, 61-78). LUDI is available from Biosym Technologies, San Diego, Calif. and LEGEND (Nishibata, Y. and A. Itai, *Tetrahedron*, (1991) 47, p. 8985). LEGEND is available from Molecular Simulations, Burlington, Mass.; and LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry," *J. Med. Chem.*, (1990) 33, 883-894. See also, Navia, M. A. and M. A. Murcko, "The Use of Structural Information in Drug Design", *Current Opinions in Structural Biology*, (1992) 2, 202-210.

Once a compound has been designed or selected by the above methods, the efficiency with which that compound may bind to RecA, LexA, Pol IV, Pol V, or other protein required for induced mutation may be tested and optimized by computational evaluation. An effective inhibitor of mutation must preferably demonstrate a relatively small difference in energy between its bound and free states (i.e., a small deformation energy of binding). Thus, the most efficient RecA, LexA, Pol IV, Pol V, or other protein inhibitors should preferably be designed with deformation energy of binding of not greater than about 10 kcal/mole, or more preferably, not greater than 7 kcal/mole.

Inhibitors of RecA, LexA, Pol IV, Pol V, or other protein required for induced mutation may interact with their target in more than one conformation that is similar in overall binding energy. In those cases, the deformation energy of binding is taken to be the difference between the energy of the free compound and the average energy of the conformations observed when the inhibitor binds to the LexA and/or RecA.

A compound designed or selected, as binding to LexA and/or RecA can be further computationally optimized so that in its bound state it would preferably lack repulsive electrostatic interaction with the target. Such non-complementary (e.g., electrostatic) interactions include repulsive charge-charge, dipole-dipole and charged dipole interactions. Specifically, the sum of all electrostatic interactions between the inhibitor and the enzyme when the inhibitor is bound to its target (e.g., RecA, LexA, Pol IV, Pol V, or other protein required for induced mutation), preferably make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., 1992); AMBER, version 4.0 (P. A. Kollman, University of California at San Francisco, 1994); QUANTA/CHARMM (Molecular Simulations, Inc., Burlington, Mass. 1994); and Insight II/Discover (Biosym Technologies Inc., San Diego, Calif., 1994). These programs may be implemented, for instance, using a Silicon Graphics workstation, IRIS 4D/35 or IBM RISC/6000 workstation model 550. Other hardware systems and software packages will be known to those skilled in the art.

Once an inhibitor of RecA, LexA, Pol IV, Pol V, or other protein required for induced mutation has been optimally selected or designed, as described above, substitutions may then be made in some of its atoms or side groups to improve or modify its binding properties. Generally, initial substitutions are conservative, e.g., the replacement group will have approximately the same size, shape, hydrophobicity and charge as the original group. It should, of course, be understood that components known in the art to alter conformation should be avoided. Such substituted chemical compounds may then be analyzed for efficiency of fit into the 3-D structures of RecA, LexA, Pol IV, Pol V, or other protein required for induced mutation by the same computer methods described in detail, above.

The compounds designed by any of the above methods are useful for inhibiting induced mutagenesis and thus are useful as therapeutic agents to reduce drug resistance.

XII. Uses of Achaogens

The achaogens described herein can be used to modulate the rate of induced mutations or more preferably to inhibit the rate of induced mutations in a cell, group of cells, or a multicellular organism. Such induced mutations can result from a drug treatment, UV radiation, inadequate nutrients, etc. Examples of drug treatments that may result in induced mutations include treatments with an antineoplastic agent, an antibacterial agent, an antiviral agent, an antiprotozoan agent, and/or an antifungal agent. Such induced mutations can lead to drug resistance or other undesireable mutations. Thus, in some embodiments, an achaogen is used to inhibit drug resistance to a drug selected from the group consisting of: an antineoplastic agent, an antibacterial agent, an antiviral agent, an antiprotozoan agent, and/or an antifungal agent.

For example, an achaogen of the present invention can be used to inhibit resistance to any antibiotic disclosed herein or otherwise known in the art. In preferred embodiments, an achaogen is used to inhibit resistance to rifampin, oxazolidinones (e.g., linezolid), fluoroquinolones (e.g., ciprofloxacin, levofloxacin, moxifloxacin, gatifloxacin, gemifloxacin), macrolides (e.g., azithromycin and clarithromycin), and later generation cephalosporins (e.g., cefaclor, cefadroxil, cefazolin, cefixime, cefoxitin, cefprozil, ceftazidime, cefuroxime, and cephalexin).

In some embodiments, the achaogens herein can be used to reduce the rate of mutation in bacteria. Mutation rate may be reduced in either or both gram-positive or gram-negative bacteria, whether such bacteria are cocci (spherical), rods, vibrio (comma shaped), or spiral.

Of the cocci bacteria, *micrococcus* and *staphylococcus* species are commonly associated with the skin, and *Streptococcus* species are commonly associated with tooth enamel and contribute to tooth decay. Of the rods family, bacteria *Bacillus* species produce endospores seen in various stages of development in the photograph and *B. cereus* cause a relatively mild food poisoning, especially due to reheated fried food. Of the *vibrio* species, *V. cholerae* is the most common bacteria and causes cholera, a severe diarrhoeal disease resulting from a toxin produced by bacterial growth in the gut. Of the spiral bacteria, *rhodospirillum* and *Treponema pallidum* are the common species to cause infection (e.g., *Treponema pallidum* causes syphilis). Spiral bacteria typically grow in shallow anaerobic conditions and can photosyntheize to obtain energy from sunlight.

Moreover, the present invention relates to achaogens that can be used to reduce the rate of mutation in either gram positive, gram negative, or mixed flora bacteria. Such bacteria include, but are not limited to, Baciccis Antracis; *Enterococcus faecalis*; *Corynebacterium; diphtheriae; Escherichia coli; Streptococcus coelicolor; Streptococcus pyogenes; Streptobacillus moniliformis; Streptococcus agalactiae; Streptococcus pneumoniae; Salmonella typhi; Salmonella paratyphi; Salmonella schottmulleri; Salmonella hirshfeldii; Staphylococcus epidermidis; Staphylococcus aureus; Klebsiella pneumoniae; Legionella pneumophila; Helicobacter pylori; Mycoplasma pneumonia; Mycobacterium tuberculosis; Mycobacterium leprae; Yersinia enterocolitica; Yersinia pestis; Vibrio cholerae; Vibrio parahaemolyticus; Rickettsia prowazekii; Rickettsia rickettsii; Rickettsia akari; Clostridium difficile; Clostridium tetani; Clostridium perfringens; Clostridium novyii; Clostridium septicum; Clostridium botulinum; Legionella pneumophila; Hemophilus influenzae; Hemophilus parainfluenzae; Hemophilus aegyptus; Chlamydia psittaci; Chlamydia trachomatis; Bordetella pertusis; Shigella* spp.; *Campylobacter jejuni; Proteus* spp.; *Citrobacter* spp.; *Enterobacter* spp.; *Pseudomonas aeruginosa; Propionibacterium* spp.; *Bacillus anthracis; Pseudomonas syringae; Spirrilum minus; Neisseria meningitidis; Listeria monocytogenes; Neisseria gonorrheae; Treponema pallidum; Francisella tularensis; Brucella* spp.; *Borrelia recurrentis; Borrelia hermsii; Borrelia turicatae; Borrelia burgdorferi; Mycobacterium avium; Mycobacterium smegmatis*; Methicillin-resistant *Staphyloccus aureus*; Vanomycin-resistant *enterococcus*; and multi-drug resistant bacteria (e.g., bacteria that are resistant to more than 1, more than 2, more than 3, or more than 4 different drugs).

In some embodiments, an achaogen herein is used to treat an already drug resistant bacterial strain such as Methicillin-resistant *Staphylococcus aureus* (MRSA) or Vancomycin-resistant *enterococcus* (VRE) by exploiting unusual aspects of rifampicin resistance. Rifampicin has fallen out of common clinical use, because rifampicin resistance emerges within 24 hours from initiation of treatment. Because the mutations that confer rifampicin resistance impose a significant growth disadvantage on bacteria, resistant bacterial populations promptly revert to rifampicin sensitivity within a few weeks of cessation of treatment. As such, nearly all MRSA and VRE strains encountered are initially rifampicin sensitive. Therefore, the present invention contemplates the use of rifampicin in combination with an achaogen to treat against MRSA and VRE. The present invention also contemplates the use of achaogens in combinations with other antibiotics to fight Gram-positive bacteria that cannot maintain resistance to certain drugs.

As such, the achaogens herein may be used to treat a bacterial infection condition such as urinary tract infections, ear infections, sinus infections, bacterial infections of the skin, bacterial infections of the lungs, sexually transmitted diseases, tuberculosis, pneumonia, lyme disease, and Legionnaire's disease. Thus any of the above conditions and other conditions resulting from bacterial infections may be prevented or treated by the compositions herein.

In another example, an achaogen is used to inhibit resistance to an antiviral agent selected from the group consisting of: AZT; Ganciclovir; valacyclovir hydrochloride (Valtrex™); Beta Interferon; Cidofovir; Ampligen™; penciclovir (Denavir™), foscarnet (Foscavir™), famciclovir (Famvir™), and acyclovir (Zovirax™).

Examples of viruses whose mutations rate may be inhibited by an achaogen include but are not limited to, human immunodeficiency virus (HIV); influenza; avian influenza; ebola; chickenpox; polio; smallpox; rabies; respiratory syncytial virus (RSV); herpes simplex virus (HSV); common cold virus; severe acute respiratory syndrome (SARS); Lassa fever (Arenaviridae family), Ebola hemorrhagic fever (Filoviridae family), hantavirus pulmonary syndrome (Bunyaviridae family), and pandemic influenza (Orthomyxoviridae family).

In another example, an achaogen is used to inhibit resistance to an antiprotozoan agent selected from the group consisting of: Chloroquine; Pyrimethamine; Mefloquine Hydroxychloroquine; Metronidazole; Atovaquone; Imidocarb; Malarone™; Febendazole; Metronidazole; Ivomec™; Iodoquinol; Diloxanide Furoate; and Ronidazole.

Examples of protozoan organisms whose mutation rate may be inhibited by an achaogen include but are not limited to, *Acanthameba; Actinophrys*; Amoeba; *Anisonema; Anthophysa; Ascaris lumbricoides; Bicosoeca; Blastocystis hominis; Codonella; Coleps; Cothurina; Cryptosporidia Difflugia; Entamoeba histolytica* (a cause of amebiasis and amebic dysentery); *Entosiphon; Epalxis; Epistylis; Euglypha; Flukes; Giardia lambia*; Hookworm *Leishmania* spp.; *Mayorella; Monosiga; Naegleria Hartmannella; Paragonimus westennani*; Paruroleptus; *Plasmodium* spp. (a cause of Malaria) (e.g., *Plasmodium falciparum; Plasmodium malariae; Plasmodium vivax* and *Plasmodium ovale*); *Pneumocystis carinii* (a common cause of pneumonia in immunodeficient persons); microfilariae; *Podophrya; Raphidiophrys*; Rhynchomonas; *Salpingoeca; Schistosoma japonicum; Schistosoma haematobium; Schistosoma mansoni*; Stentor; *Strongyloides; Stylonychia*; Tapeworms; *Trichomonas* spp. (e.g., *Trichuris trichiuris* and *Trichomonas vaginalis* (a cause of vaginal infection)); *Typanosoma* spp.; and Vorticella.

In another example, an achaogen is used to inhibit resistance to an antifungal agent selected from the group consisting of: imidazoles (e.g., clotrimazole, miconazole, econazole, ketonazole, oxiconazole, sulconazole), ciclopiroz, butenafine, and allylamines.

Examples of fungus infections whose mutation rate may be inhibited by an achaogen include but are not limited to, tinea; athlete's foot; jock itch; and *candida*.

In particular, the present invention contemplates the prevention and treatment of infectious diseases identified in Table 3 which have re-emerged with increased resistance to medications:

TABLE 3

Examples of Infectious Diseases With Increased Resistance to Medications.

| | |
|---|---|
| Cryptosporidiosis | *Cryptosporidium parvum* (protozoan) |
| Diphtheria | *Corynebacterium diptheriae* (bacterium) |
| Malaria | *Plasmodium* species (protozoan) |
| meningitis, necrotizing fasciitis (flesh-eating disease), toxic-shock syndrome, and other diseases | Group A *Streptococcus* (bacterium) |
| pertussis (whooping cough) | *Bordetella pertussis* (bacterium) |
| Rabies | Rhabdovirus group (virus) |
| rubeola (measles) | *Morbillivirus* genus (virus) |
| Schistosomiasis | *Schistosoma* species (helminth) |
| Tuberculosis | *Mycobacterium tuberculosis* (bacterium) |
| yellow fever | *Flavivirus* group (virus) |
| HIV | *staphylococcus* |

The inducible mutation pathways discussed herein are also known to exist in eukaryotic cells, though they are expected to be quite different in mechanistic detail. See Diaz, M., et. al. *Mol Cancer Res.*, (2003) 1:836-847; Zhang, Y., et al., *Nucleic Acids Res.*, (2000) 28:4147-4156. Thus, achaogens can be used to inhibit mutation in eukaryotic cells. In one embodiment, achaogens are used as an adjuvant or supplement to therapies in which therapeutic outcomes are compromised by mutations. These therapies include, but are not limited to cancer chemotherapy. In another embodiment, an achaogen is used as a prophylactic to prevent mutations, for example to prevent tumorgenesis and carcinogenesis. The achaogens are suitable to prevent both benign and malignant tumors.

Examples of cancers that may be treatable or preventable by the present invention include, but are not limited to, breast cancer; skin cancer; bone cancer; prostate cancer; liver cancer; lung cancer; brain cancer; cancer of the larynx; gallbladder; pancreas; rectum; parathyroid; thyroid; adrenal; neural tissue; head and neck; colon; stomach; bronchi; kidneys; basal cell carcinoma; squamous cell carcinoma of both ulcerating and papillary type; metastatic skin carcinoma; osteo sarcoma; Ewing's sarcoma; veticulum cell sarcoma; myeloma; giant cell tumor; small-cell lung tumor; gallstones; islet cell tumor; primary brain tumor; acute and chronic lymphocytic and granulocytic tumors; hairy-cell leukemia; adenoma; hyperplasia; medullary carcinoma; pheochromocytoma; mucosal neuronms; intestinal ganglioneuromas; hyperplastic corneal nerve tumor; marfanoid habitus tumor; Wilm's tumor; seminoma; ovarian tumor; leiomyomater tumor; cervical dysplasia and in situ carcinoma; neuroblastoma; retinoblastoma; soft tissue sarcoma; malignant carcinoid; topical skin lesion; mycosis fungoide; rhabdomyosarcoma; Kaposi's sarcoma; osteogenic and other sarcoma; malignant hypercalcemia; renal cell tumor; polycythermia vera; adenocarcinoma; glioblastoma multiforme; leukemias (including acute myelogenous leukemia); lymphomas; malignant melanomas; epidermoid carcinomas; chronic myleoid lymphoma; gastrointestinal stromal tumors; and melanoma.

In particular, the methods and compositions herein are useful for inhibiting the development of resistance to anti-cancer (antineoplastic) medications including, but are not limited to, Gleevec; antineoplastic drugs; including alkylating agents such as alkyl sulfonates (busulfan; improsulfan; piposulfan); aziridines (benzodepa; carboquone; meturedepa; uredepa); ethylenimines and methylmelamines (altretamine; triethylenemelamine; triethylenephosphoramide; triethylenethiophosphoramide; trimethylolmelamine); nitrogen mustards (chlorambucil; chlornaphazine; cyclophosphamide; estramustine; ifosfamide; mechlorethamine; mechlorethamine oxide hydrochloride; melphalan; novembichin; phenesterine; prednimustine; trofosfamide; uracil mustard); nitrosoureas (carmustine; chlorozotocin; fotenmustine; lomustine; nimustine; ranimustine); dacarbazine; mannomustine; mitobranitol; mitolactol; pipobroman; doxorubicin; and cisplatin (including derivatives).

Additional anticancer medications that may benefit from co-administration with an achaogen include, but are not limited to, Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate;

Duazomycin; Edatrexate; Eflornithine; Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Imofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

In particular, the present invention contemplates the use of an achaogen to prevent the development of drug resistance, wherein drug resistance results from at least one, 2, 3, 4, 5, 6, 7, 8, 9, 10, 20, 30, 40 or 50 mutations. The achaogen can also be used to prevent the development of drug resistance, wherein the drug resistance results from at least one, 2, 3, 4, 5, 6, 7, 8, 9, 10, 20, 30, 40 or 50 deletion/insertion mutations.

Such an achaogen can be administered independently or in combination with another therapeutic agent (e.g., any of the antibodies, antifungal agents, antiviral agents, antiprotozoan agents, and antineoplastic agents herein).

In addition to the therapeutic uses described above, the achaogens described herein are also useful in numerous industrial applications. In particular, achaogens are useful in industrial processes that are hindered due to the development of mutations in the organisms used in the processes. Suitable applications include the prevention of mutations in yeast used in breweries and other biotechnology applications. Another suitable use is to prevent mutations in bacteria (or eukaryotic cells) that are used for the synthesis of proteins, like antibodies, etc. Industrial applications include the improved utility of cleaning products, such as soap, toothpaste, and house-cleaning products. Others suitable uses will be apparent to one of skill in the art based on the disclosure herein.

XIII. Screening for Resistance

In any of the embodiments herein, an organism or patient can be first tested for drug resistance prior to the administration of an achaogen. A test to detect drug resistance or susceptibility to drug resistance may involve taking a biopsy or sample from the patient. Samples can be obtained from microorganisms (e.g., viruses, bacteria, fungi, protozoans) or larger organisms (e.g., human, monkey, cows, pigs, horses, sheep, dogs and cats). The samples can come from tissues or tissue homogenates or fluids of an organism and cells or cell cultures. For example, samples can be obtained from whole blood, serum, semen, vaginal fluid, ear wax, nasal drips, saliva, tears, urine, fecal material, sweat, buccal, skin, spinal fluid, tissue biopsy or necropsy, and hair. Samples can also be derived from ex vivo cell cultures, including the growth medium, recombinant cells and cell components. In some embodiments, samples can be obtained from diseased cells and from non-diseased cells.

Several techniques are known in the art for determining whether a particular strain of bacteria has developed resistance to an antibiotic. For example, if the administration of an antibiotic at a dose equivalent to its ED50 (the dose at which 50% of patients being treated respond) to a patient suffering from a bacterial infection does not result in a therapeutic benefit, the bacteria is considered to be resistant to the antibiotic.

In some embodiments, a sample obtained from an organism is assayed to detect one or more mutations in a gene that modulates induced mutation. Examples of such genes include but are not limited to 16S rRNA, 23S rRNA, clpXP, dinB, din, dnaE2, gyrA, gyrB, katG, inhA, lon protease, L4 ribosomal methylases, lexa, norA, recA. psiB, parC, parE, polB, rpoS, rpoB, sxt, umuC, and umuD. Generally, mutations in psiB, dinI clpXP, and/or lon are associated with an increased rate of mutagenesis or susceptibility to induced mutations. On the other hand, mutations in 16S rRNA, 23S rRNA, dinB, dnaE2, gyrA, gyrB, katG, inhA umuC, umuD, lexA, norA, recA, L4 ribosomal methylases, parC, parE, rpoS, rpoB, sxt, and polB are associated with resistance to induced mutations or lack of induced mutagenesis.

Examples of mutations that may be used as a diagnosis for drug resistance or susceptibility thereto include: mutations in lexa that affects its ability to auto-cleave (e.g., S119A and S141A); mutations in recA and its ability to bind ssDNA and/or interact with LexA; mutations in gyrA and gyrB genes, which encode gyrase; mutations in parC and parE genes, which encode subunits of topoisomerase IV; mutations in genes that affect outer membrane permeability or export through an active efflux system (see e.g. Poole, K., 44(10): 2595-2599 (2000)); mutations in dnaE2; mutations in the rpoS and rpoB associated with resistance to Rifampin (see, e.g., Boshoff, H., *Cell*, (2002) 113, 183-193); mutations in the 23S rRNA genes or L4 ribosomal methylases associated with resistance to linezolid, erythromycin, and other macrolides; mutations in the katG or inhA genes associated with resistance to isoniazid; mutations in the 16S rRNA genes associated with resistance to streptomycin; and mutations in gene and gene products that modulate induced mutagenesis in non-bacterial organisms. Other examples of genes whose mutations may be associated with drug resistance are disclosed in herein.

Assays that test the level of expression of gene products that enhance or suppress induced mutagenesis may be used as a diagnostic for drug resistance or susceptibility to drug resistance. Such expression can be detected by measuring the level of gene transcripts or gene products of such genes. Examples of genes whose overexpression may be used as a diagnosis for lack of drug resistance or susceptibility thereto include, but are not limited to, psiB, dinI, clpXP, and lon. Examples of genes whose overexpression may be used as a diagnosis of drug resistance or susceptibility thereto include, but are not limited to, 16S rRNA, 23S rRNA, dinB, dnaE2, gyrA, gyrB, katG, inhA umuC, umuD, lexA, norA, recA, L4 ribosomal methylases, parC, parE, rpoS, rpoB, sxt, and polB.

Detection of level of expression can be made using any method known in the art. In preferred embodiments, expression levels are detected using a microarray. For example, a sample can be obtained from an organism being tested. The sample can be assayed to detect a level of expression of, for example, a cancerous cell, bacterial infection, viral infection. This level of expression can then be compared with a level of expression in a control. If the level of expression of the above genes is greater in the sample than in a control—drug resistance or susceptibility to drug resistance is likely to have occurred or to occur. If the level of expression in an organism is less than a level of expression in a control—drug resistance or susceptibility to drug resistance is not predicted to have occurred or to occur.

After screening for drug resistance, a patient having detectable levels of drug resistance can be administered an achaogen and one or more therapeutic agents disclosed herein.

XIV. Kits

The present invention also contemplates kits comprising one or more vials, wherein at least one vial comprises an achaogen of the present invention. The kits also contain a set of written instructions for use of the compositions therein. For example, instructions can direct an individual as to the specific achaogen to be used, dosages to be applied, frequency and duration of use, and methods of adminsteration. The kits can also include additional agents to be co-adminstered, e.g., any drug (e.g., antibiotic, antiviral, anticancer, etc.) as well a instructions for the coadministration of the achaogen and the additional agent(s).

Preferably, a vial comprises an achaogen in a pharmaceutical formulation. In some embodiments, a kit comprises one or more vials of an achaogen forumated for local or system adminsterations. In some embodiments, an achaogen in a vial may coformulated with a second therapeutic agent (e.g., anti-protozoan, antiviral, antibiotic, antifungal, or an antineoplastic agent).

The kit can also include one or more containers with additional achaogens and/or therapeutic agents.

The kit can also include a diagnostic tool to detect the presence, absence, and/or susceptibility to drug resistance. A diagnostic tool of the present invention can include nucleic acid primers, probes, antibodies, microarrays, microfluidic devices, etc. A diagnostic tool of the present invention can detect level of gene expression, SNPs, or rate of induced mutation. In preferred embodiments, the diagnostic tool is a microarray.

In some embodiments, a diagnostic tool detects one or more mutations in a gene(s) associated with induced mutations, such as 16S rRNA, 23S rRNA, clpXP, dinB, din, dnaE2, gyrA, gyrB, katG, inhA, lon protease, L4 ribosomal methylases, lexA, lon protease, norA, recA. recN, psiB, parC, parE, polB, psiB, rpoS, rpoB, sxt, umuC, umuD, uvrA, uvrB, and uvrD.

In some embodiments, a diagnostic tool detects level of expression of a gene(s) associated with induced mutagenesis. Examples of such genes include, but are not limited to, 16S rRNA, 23S rRNA, clpXP, dinB; din, dnaE2, gyrA, gyrB, katG, inhA, ion protease, L4 ribosomal methylases, lexA, ion protease, norA, recA, recN, psiB, parC, parE, polB, psiB, rpoS, rpoB, sxt, umuC, umuD, uvrA, uvrB, and uvrD.

EXAMPLES

Example 1

To demonstrate that the administration of ciprofloxacin induces mutation, we examined the evolution of resistance of wild type MG1655 *E. coli* on solid media plates containing 35 ng/mL ciprofloxacin. First we differentiated colonies that arose during the exponential growth phase, prior to plating, and those that arose after plating. This was done by isolating colonies, noting the day on which they appeared, and then regrowing the colonies and determining the time it took for a colony to appear. For example, if a colony appeared on day three, but then required three days to re-grow, the founding cell was assumed to have obtained a resistance mutation during the exponential growth phase, prior to exposure to antibiotic. If a colony is isolated on day five and then found to require only one day to re-grow, the founding cell was assumed to have mutated on day four after exposure to the antibiotic.

Figure 11:
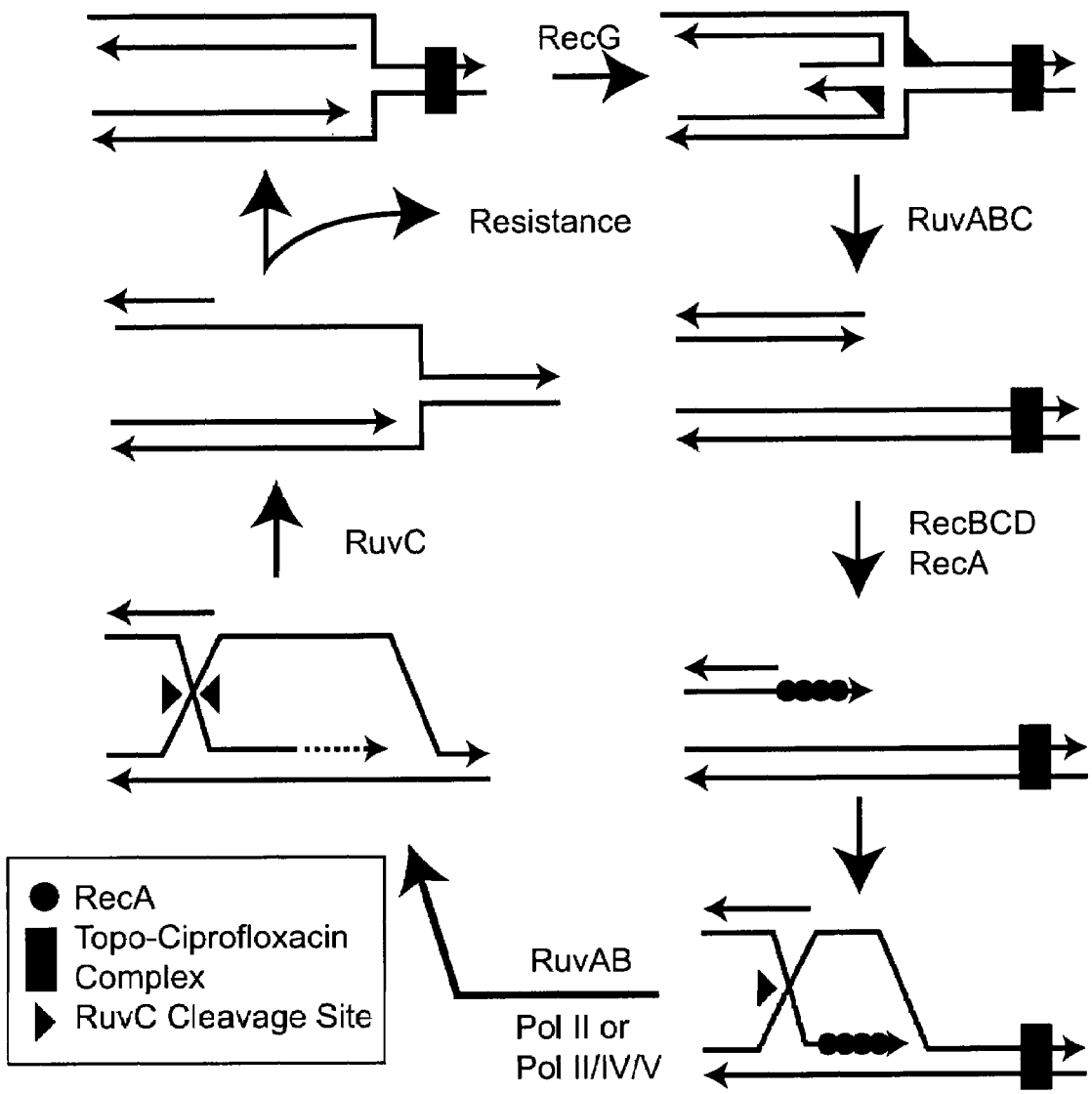
FIG. 11 illustrates a proposed mechanism for recombination dependent replication restart in the presence of ciprofloxacin. In this model, RuvAB acts to displace the trapped topoisomerase complex from DNA, allowing for the establishment of a new replication fork on which PriA may reassemble a processive replisome.

At least four observations were immediately apparent from inspection of the data. First, the number of mutations per viable cell per day increased by at least four-orders of magnitude, and possibly at least five orders of magnitude (from $3.4 (+/-2.0) \times 10^{-10}$ to $2.9(+/-0.41) \times 10^{-5}$) after exposure to the antibiotic (similar to results reported earlier in Riesenfeld, C, *Antimicrob. Agents Chemother*. (1997) 41:2059-2060). Second, the rates of mutation prior to drug exposure were virtually independent of the gene deletions described below in Example 2, whereas the mutation rate after drug exposure was strongly dependent (being both increased or reduced upon deletion of certain genes, see below). Fourth, the spectrum of mutations occurring in the presence of the antibiotic differed significantly from those occurring during exponential growth. The isolated growth-dependent mutations were strictly substitutions, while the induced mutations were both substitutions and small, in frame deletions (FIG. 11). The type of mutation (base substitution versus deletion) that arose before drug exposure was independent of gene deletion, whereas those that arose after exposure to ciprofloxacin depended strongly on gene deletion. This data implies that a mutational system is induced upon exposure to ciprofloxacin and that this system is both mechanistically distinct from any system conferring mutations during exponential growth and responsible for the majority of the mutations that give rise to ciprofloxacin resistance.

To further understand the effects of induced mutation resulting from exposure to antibiotics, we determined whether or not pre-exposure to rifampicin, an unrelated antibiotic, could induce mutations that bestowed the bacteria with ciprofloxacin resistance, *E. coli* MG1655 were incubated in PBS containing 0, 4, 12, and 36 mg/mL rifampicin for four days at 37° C., and then plated on agar containing Luria Broth (LB) with 35 ng/mL ciprofloxacin. Incubation in the presence of 0 or 4 mg/mL had no effect on the number of ciprofloxacin resistant colonies present in the culture. However, incubation in the presence of more rifampicin (12 or 36 mg/mL) resulted in a dramatic increase in the number of ciprofloxacin resistant cells. This effect was essentially completely lost in the umuDC deletion stain, demonstrating that the resistance in the wild type strain results from induced mutation mediated at least in part by Pol V. Apparently, pre-incubation with a suitable concentration of rifampicin induces the mutation system (for example, during repair synthesis).

Example 2

To determine whether the evolution of resistance to ciprofloxacin is under genetic control, and if so, to determine which genes are involved, we constructed a series of isogenic loss of function strains of *E. coli* K-12 (MG1655) (Table 5). We have selected the *E. coli* strain MG1655 as the genetic background, as this K-12 strain was used in the *E. coli* genome sequencing project. Strains listed in the accompanying Table 4 were constructed using PCR-mediated gene replacement. See Daiguan Yu, et al., Proc. Natl. Acad. Sci., May 2000; 97: 5978-5983. PCR reactions were performed using Platinum pfx DNA polymerase from Invitrogen, with standard cycling parameters. Genomic template DNA was prepared from a fresh bacterial overnight culture using the DNeasy kit (Qiagen).

Mutation cassettes were constructed using 3-way PCR, as described by Murphy et al. Gene (2000) 246:321-330. Gene specific components were annealed to an antibiotic resistance marker by combining the three fragments in a PCR reaction, in equal volume. Conditions for this PCR reaction were standard, with the exception that the proximal primers were used in limiting amounts.

Deletion cassettes consisted of approximately 500 base pair regions upstream and downstream to the gene deleted, including the first and last 2-10 codons of the gene, on either side of an antibiotic resistance cassette in reverse orientation to the gene being deleted. To construct the lexA point mutant, the lexA gene was amplified from genomic MG1655 DNA by PCR using primers lexA NF-SphI and lexA_OrfR-NdeI, digested with SphI, NdeI and ligated into SphI, NdeI digested pUC18 vector (5). The S119A mutation (TCG->GCG) was introduced in the resulting plasmid using the Quikchange Site-directed Mutagenesis kit (Stratagene, La Jolla, Calif.) and primers LexA_S119A_QCF and LexA_S119A_QCR. The resulting allele was confirmed by sequencing, digested with SphI, NdeI and ligated to a DNA fragment containing an antibiotic resistance cassette and 500 bp of sequence downstream to the lexA gene. Therefore, the final cassette contains 500 bp of upstream DNA, the mutated ORF, an NdeI site attaching an antibiotic resistance marker in reverse orientation, and approximately 500 bp of downstream DNA.

The antibiotic resistance markers were amplified as follows. The kanamycin (Km) resistance cassette was amplified from pUC4K using primers 5'-GGA AAG CCA CGT TGT GTC TC (SEQ ID NO: 18) and 5'-CGA TTT ATT CAA CAA AGC CGC. (SEQ ID NO: 19). Similarly, the spectinomycin (Spec) resistance cassette was amplified from pomega, and the chloramphenicol (Cm) resistance cassette from pSU18. All oligonucleotide primers used in the construction of the disruption cassettes are listed in FIG. 19.

Generation of the genomic deletions in MG1655 proceeded in two steps: (i) genomic insertion into strain PS6275 and (ii) P1-mediated transfer of the deletion cassette to MG1655. In the first step, the linear DNA fragments (PCR products) were electroporated into the hyper-recombinational *E. coli* strain PS6275 [Yu, D, et al. Proc Natl Acad Sci USA (2000) 97:5978-5983], a derivative of MG1655 which carries the lambda phage red genes. This strain accepted the linear PCR product and recombined it into the genome with high efficiency. Recombination genes were activated by growing DY329 at 42° C. and the competent cells stored at −80° C. The competent cells were transformed with the desired cassettes and transformants selected at 30° C. on LB supplemented with the appropriate antibiotic (kanamycin 30 _g/mL, chloramphenicol 25 _g/mL, or spectinomycin 100 _g/mL), and grown at 30° C. Although MG-DY329 was engineered such that the lambda _phage red genes could be easily removed to return the cell to a non-hyper-recombinational background, we used P1 transduction to move the gene-specific disruption from PS6275 into MG1655. MG1655 provides a more 'wild-type' background than MG-DY329, and thus simplifies the interpretation of the results. Gene deletions were verified by PCR; the lexA(S119A) strain was confirmed by PCR followed by sequencing.

TABLE 4

Table of strains used.

| Parent | Mutation |
|---|---|
| MG1655 | — |
| ATCC25922 | — |
| MG1655 | DY329 (nadA::RED) |
| MG1655 | lacZΔ::kan |
| MG1655 | polBΔ::kan |
| MG1655 | polBΔ::spc |
| MG1655 | dinBΔ::kan |
| MG1655 | umuDCΔ::kan |
| MG1655 | umuDCΔ::cat |
| MG1655 | polBΔ::Spc, dinBΔ::kan |
| MG1655 | polBΔ::Spc, umuDCΔ::kan |
| MG1655 | dinBΔ::kan umuDCΔ::cat |
| MG1655 | polBΔ::spc dinBΔ::kan, UmuDC::Cat |
| MG1655 | LexA(S119A)::kan |
| MG1655 | recAΔ::kan |
| MG1655 | recBΔ::kan |
| MG1655 | recDΔ::kan |
| MG1655 | recFΔ::kan |
| MG1655 | recGΔ::kan |
| MG1655 | ruvBΔ::kan |
| MG1655 | ruvCΔ::kan |
| MG1655 | sulAΔ::kan |
| MG1655 | priAΔ::kan |
| ATCC25922 | lacZΔ::kan |
| ATCC25922 | LexA(S119A)::kan |
| ATCC25922 | recFΔ::kan |

With the isogenic loss of function strains in hand, mutation in response to ciprofloxacin (obtained from U.S. Biologicals) was determined using a protocol based on the Stressful Lifestyle Adaptive Mutation (SLAM) assay as illustrated in FIG. 6. Five colonies of each strain, selected from 30 ug/mL kan plates, were grown for 24 hours in LB at 37° C. Dilutions of each culture were made in duplicate and plated on LB plates to determine the number of viable cells.

To assay for mutation, 150 μL of each culture was plated twice on LB plates containing 35 ng/mL ciprofloxacin. Also, two 150 μL cultures from each strain were plated on five additional plates for use in 'survival' experiments (see below). The concentration of ciprofloxacin used was chosen based on trial experiments with the MG1655 parent strain which indicated that 35 ng/mL ciprofloxacin maximized mutation-dependent growth. Every twenty-four hours for thirteen days post-plating, colonies were counted and marked and up to 10 representative colonies per strain were stocked in 15% glycerol and stored at −80° C., for use in the reconstruction experiments (see below). Also, to determine the number of ciprofloxacin susceptible cells remaining on the plates, parallel 'survival' experiments were performed. The 'survival' experiment plates were treated exactly as the SLAM plates, except at specified time points, representative plates were sacrificed by excising all visible colonies, recovering the remaining agar in 9 mg/mL saline, and plating dilutions of the resulting solution on LB to determine the number of viable cells.

After thirteen days, a reconstruction experiment was performed to determine which of the resistant colonies isolated had evolved resistance via induced mutation after exposure to the antibiotic. The stocked colony suspensions isolated during the original experiment were used to inoculate 1 mL of LB and grown overnight at 37° C. The resulting cultures were then diluted and duplicate plated on LB and LB containing 35 ng/mL ciprofloxacin and the time elapsed to colony formation was recorded and compared to the original experiment. Only those colonies that grew in a shorter time during the reconstruction experiment than in the original experiment were considered to have acquired an induced mutation, i.e. occurred after exposure to the antibiotic. Using the colony in these experiments requires a single mutation (in the gyrA gene, confirmed by sequencing).

Sequencing the gyrA gene revealed an interesting pattern. In the wild type stain, induced mutants (arose after day 4) showed an approximately ~2:1 ratio of point mutation to codon deletion. Deletion of any of the three polymerases resulted in 100% codon deletion, implying a major mutational sub-branch that depends on the activity of all three polymerases is required for base substitution mutation. The codon deletion pathway, however, can function with any one of the induced mutation-causing polymerase genes deleted.

TABLE 5

Strain growth, ciprofloxacin sensitivity, and mutation spectra

| Strain | Relative Doubling Time | ciprofloxacin MIC (ng/ml) | | | Exponential Growth Mutation Spectra | | | Post-ciprofloxacin Exposure Day 5-13 Mutation Spectra | | |
|---|---|---|---|---|---|---|---|---|---|---|
| | | WT gyrA | gyrA S83Δ | gyrA S83L | % WT | % Base Substitution | % Codon Δ | % WT | % Base Substitution | % Codon Δ |
| ΔlacZ | 1.0 (±0.01) | 35.0 | 250.0 | 450 | 16.7 | 83.3 | 0.0 | 22.2 | 61.2 | 16.7 |
| ΔpolB | 1.1 (±0.10) | 30.0 | 250.0 | 450 | 28.6 | 71.4 | 0.0 | 0.0 | 0.0 | 100.0 |
| ΔdinB | 1.0 (±0.03) | 35.0 | 250.0 | 450 | 16.7 | 83.3 | 0.0 | 0.0 | 0.0 | 100.0 |
| ΔumuDC | 1.0 (±0.01) | 35.0 | 250.0 | 450 | 25.0 | 75.0 | 0.0 | 33.3 | 0.0 | 66.7 |
| ΔpolB, ΔdinB | 1.0 (±0.12) | 25.0 | 250.0 | 450 | 50.0 | 50.0 | 0.0 | 83.3 | 0.0 | 16.7 |
| ΔpolB, ΔumuDC | 1.1 (±0.19) | 25.0 | 250.0 | 450 | 66.7 | 33.3 | 0.0 | 0.0 | 0.0 | 100.0 |
| ΔdinB, ΔumuDC | 1.1 (±0.08) | 35.0 | 250.0 | 450 | 16.7 | 83.3 | 0.0 | 33.3 | 0.0 | 66.7 |
| ΔpolB, ΔdinB, ΔumuDC | 1.2 (±0.17) | 25.0 | 250.0 | 450 | 42.9 | 57.1 | 0.0 | 0.0 | 0.0 | 100.0 |
| lexA (S119A) | 1.0 (±0.03) | 30.0 | 250.0 | 350 | 16.7 | 83.3 | 0.0 | 0.0 | 0.0 | 100.0 |
| ΔrecD | 1.0 (±0.10) | 35.0 | 250.0 | 350 | 0.0 | 100.0 | 0.0 | 0.0 | 80.0 | 20.0 | counts of induced mutants on the ciprofloxacin containing SLAM plates and the viable cell counts from the 'survival' experiments, an induced mutation rate was calculated per viable cell.

Figure 3:
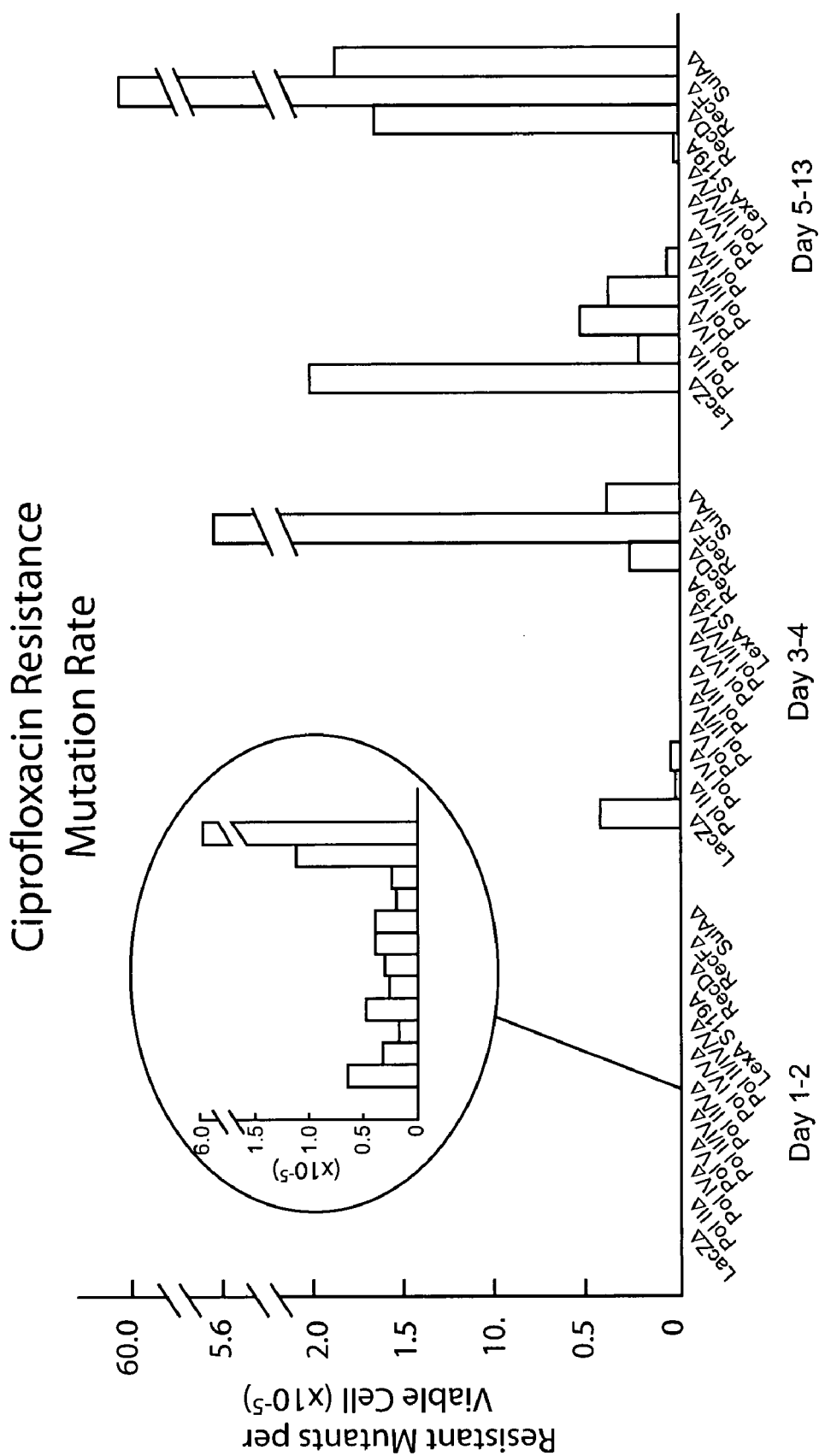
FIG. 3 illustrates mutation rates for different bacterial strains in the presence of ciprofloxacin.
Figure 10:
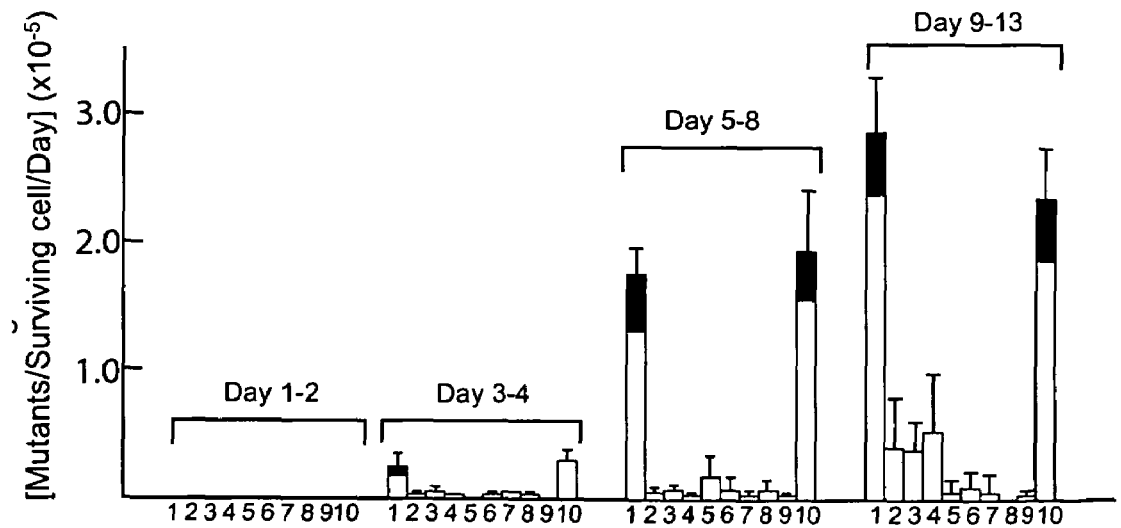
FIG. 10 illustrates mutation rate to ciprofloxacin resistance of the following ten strains: ΔlacZ [strain 1], ΔpolB [strain 2], ΔdinB [strain 3], ΔumuDC [strain 4], ΔpolB/ΔdinB [strain 5], ΔpolB/ΔumuDC [strain 6], ΔdinB/ΔumuDC [strain 7], ΔpolB/ΔdinB/ΔumuDC [strain 8], lexA(S119A) [strain 9], and ΔrecD [strain 10]; solid bars represent base substitution mutations and shaded bars represent codon deletion. Values represent number of resistant mutants per surviving cell per day. Error bars represent standard deviation from three independent rate determinations.

The data on rates of mutation to Ciprofloxacin resistance are shown in FIGS. 3 and 10. As shown, resistance was found to be significantly reduced in several strains, including polB_ (Pol II deletion strain); dinB_(Pol IV deletion strain); umuD-C_(Pol V deletion stain), and lexA(Ind-) (which cannot under autocleavage and thus makes the strain uninducible). The largest effect from any single mutation was seen for the LexA (Ind-) strain which was more than two orders of magnitude less able to evolve resistance to ciprofloxacin (the precise amount depending on the antibiotic concentration). The observed effect is remarkably large when considered in the context of clinical resistance. Clinically relevant high resistance requires multiple independent mutations. See Drlica, K, et al. Microbiol Mol. Biol. Rev. (1997) 61:377-392; Gibreel, A, et al. Antimicrob. Agents Chemother. (1998) 42:3276-3278; Kaatz, G W, Antimicrob Agents Chemother. (1993) 37:1086-1094; Yoshida, H, et al. J. Bacteriol., (1990) 172: 6942-6949; Poole, K., Antimicrob. Agents Chemother. (2000) 44:2233-2241; Kern, W V, Antimicrob. Agents Chemother. (2000) 44:814-820; Fukuda, H, Antimicrob. Agents Chemother. (1998) 42:1917-1922, whereas resistance In addition to the genes listed in Table 5 and FIGS. 3 and 10, our model predicts that strains deficient in replication restart (FIG. 11) should also have reduced rates of mutatiom to quinolone resistance when under selection by quinolones. More specifically, our model predicts that inhibitors of the proteins encoded by recA, recB, recG, ruvA, ruvB, ruvC and priA may have achaogenic properties as they would inhibit access to the error prone repair of DNA by PolIV and Poly.

Example 3

Figure 8:
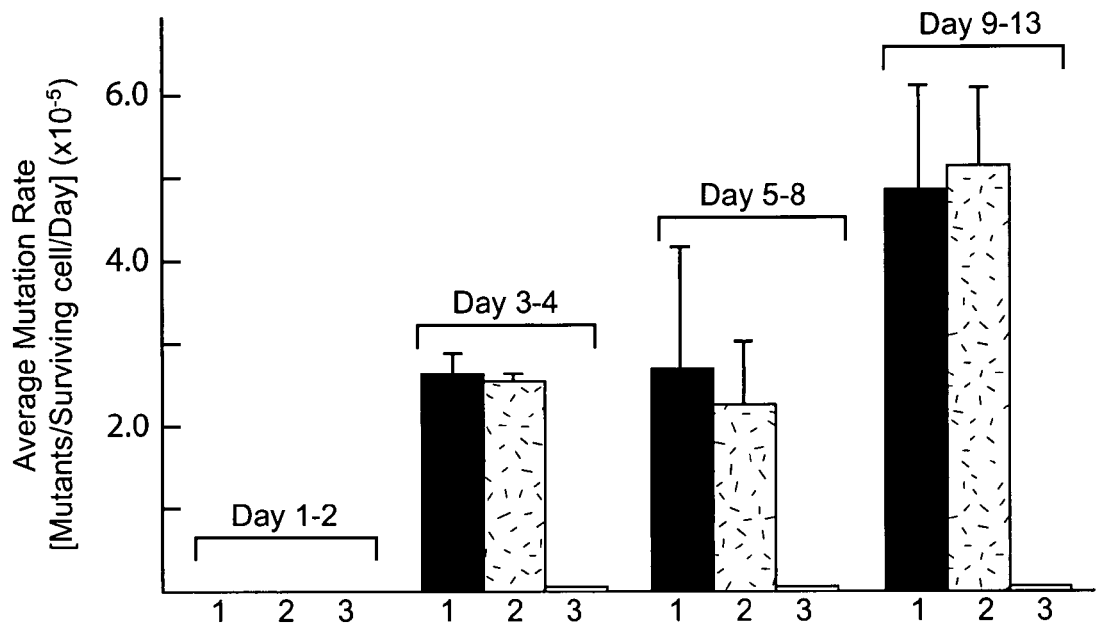
FIG. 8 illustrates a comparison of mutation rate of three different *E. coli* strains as measured by comparing their ability to evolve a 'first level' resistance to ciprofloxacin (i.e., resistance to 35 ng/ml ciprofloxacin, the level of resistance conferred by single point mutations in the gyrA gene). Strain 1 is ATCC 25922; strain 2 is ATCC 25922-ΔlacZ; and strain 3 is ATCC 25922-lexA(S119A). Bars represent total mutation rate (base substitution and codon deletion). Error bars represent standard deviation from three independent rate determinations.

It was determined if blocking the ability of LexA (the DNA binding protein that represses the expression of SOS gene products) to undergo its proteolytic self-cleavage reaction would cripple the ability of E. coli cells to become resistant to ciprofloxacin, as well-defined point mutations are required for ciprofloxacin resistance. FIG. 8 shows compares three E. coli strains for their ability to evolve 'first level' resistance to ciprofloxacin (i.e., the ability to grow in the presence of 35 ng/ml ciprofloxacin). Strain (1) is ATCC 25922; strain (2) is ATCC 25922-ΔlacZ; and strain (3) is ATCC 25922-lexA (S119A). The LexA protein in strain (3) cannot undergo self-cleavage, because its nucleophillic serine has been replaced with an alanine. Because it contains a non-cleavable LexA rather than a wild-type version of the LexA protein, Strain (3) is approximately 100-fold less able to acquire the single point mutation in gyrA conferring resistance to 35 ng/ml ciprofloxacin. While a single point mutation in the gyrA gene allows cells to grow at low ciprofloxacin concentrations (35 ng/ml), clinical resistance is far higher (approximately 100 fold higher, >15 ug/ml) and requires 3 to 5 independent point mutations.

To determine if ATCC 25922-lexA(S119A) is similarly crippled in its ability to evolve the next 'tier' of ciprofloxacin resistance (e.g., an additional mutation, this time in the ParC gene, which would allow E. coli cells to grow in the presence of 650 ng/ml ciprofloxacin) ATCC 25922-ΔlacZ and ATCC 25922-lexA(S119A) clones that had already acquired low level resistance to ciprofloxacin (35 ng/ml) via single point mutations in the gyrA gene and were used to measure their ability to evolve resistance to 650 ng/ml ciprofloxacin.

Figure 9:
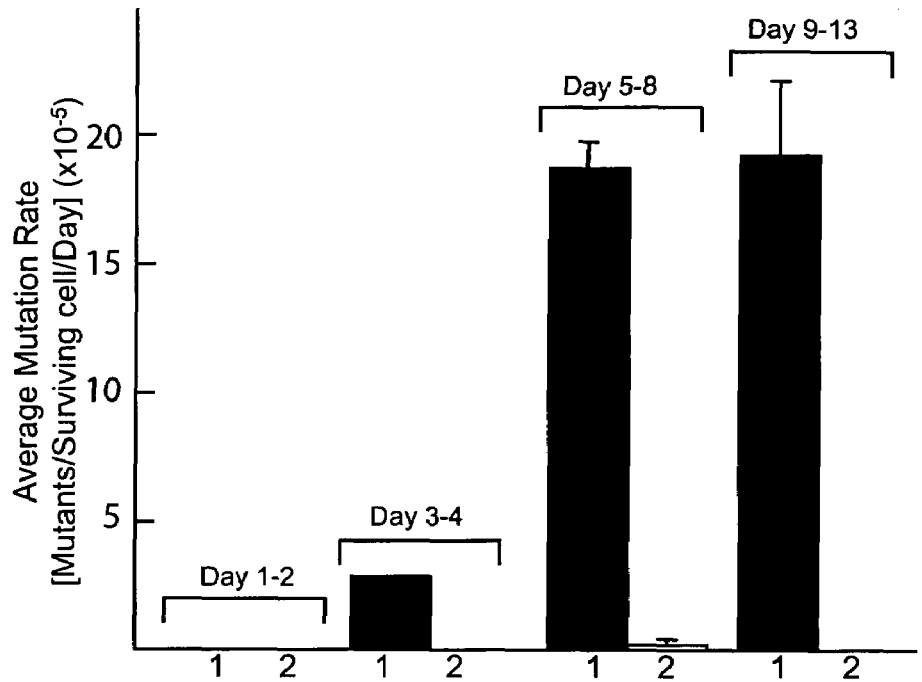
FIG. 9 illustrates a mutation rate of two different *E. coli* strains that are already resistant to 35 ng/ml ciprofloxacin and their ability to evolve resistance to higher concentrations of ciprofloxacin (i.e., to 650 ng/ml ciprofloxacin). Strain 1 is ATCC 25922-ΔlacZ(gyrA(S83L)), and strain 2 is ATCC 25922-lexA(S119A)(gyrA(S83L)). Error bars represent standard deviation from two independent rate determinations.

FIG. 9 compares the ability of two already resistant strains (to 35 ng/ml ciprofloxacin) to evolve resistance to 650 ng/ml ciprofloxacin. This 'second step' mutation rate was $1.9 (\pm 0.21) \times 10^{-4}$ mutants/(cell day) in the wild-type strain and $5.5 (\pm 4.9) \times 10^{-7}$ mutants/(cell day) in the lexA(S119A) strain. Thus, combining the relative rates for both steps, the lexA mutant evolves resistance to 650 ng/mL ciprofloxacin with a rate more than $10^4$ times reduced relative to wild-type.

Considering that clinical resistance requires three to five independent mutations, the data implies that the lexA (S119A) mutant should evolve clinical resistance at least $10^6$ times more slowly. These results demonstrate that LexA cleavage-mediated derepression of one or more genes, possibly the inducible polymerases, is not important for survival in the presence of the antibiotic at these concentrations, but is critical for mutation and the evolution of resistance.

Example 4

In vivo experiments were performed in mice to predict the effect on the emergence of drug resistance in an infection context with the cleavage of LexA effectively inhibited.

Infections were established in mice thigh muscle with one of the following two bacterial strains—an essentially wild type 25922 (a pathogenic strain of E. coli) where the lacZ gene was replaced with the kan marker (as described above) or a variant of 25922 modified as described above to possess the lexA gene product was LexA(S119A) gene instead of lexA wild type gene. These strains are referred to as 'LacZ' or as 'ATCC 25922-ΔlacZ' and 'LexA(S119A)' or 'ATCC 25922-lexA(S119A), respectively. Ciprofloxacin was administered to the mice at a drug dose that was approximately cytostatic. Mice were killed, their legs homogenized, total cell counts were taken from each thigh, and then the thighs were plated on ciprofloxacin containing plates to count ciprofloxacin resistance colonies. The data from this experiment are presented in Table 6 and in FIG. 12.

TABLE 6

| Colonies isolated on plates containing 20/80 ng/mL ciprofloxacin | | |
|---|---|---|
| ays post infection | DLacZ | LexA(S119A) |
| 1 | 93/65 | 3/1 |
| 2 | 28/23 | 2/0 |

As can be seen from Table 6, very few ciprofloxacin resistant bacteria were observed in the mutant LexA(S119A) mutant strain compared to the wild type bacteria.

Figure 12:
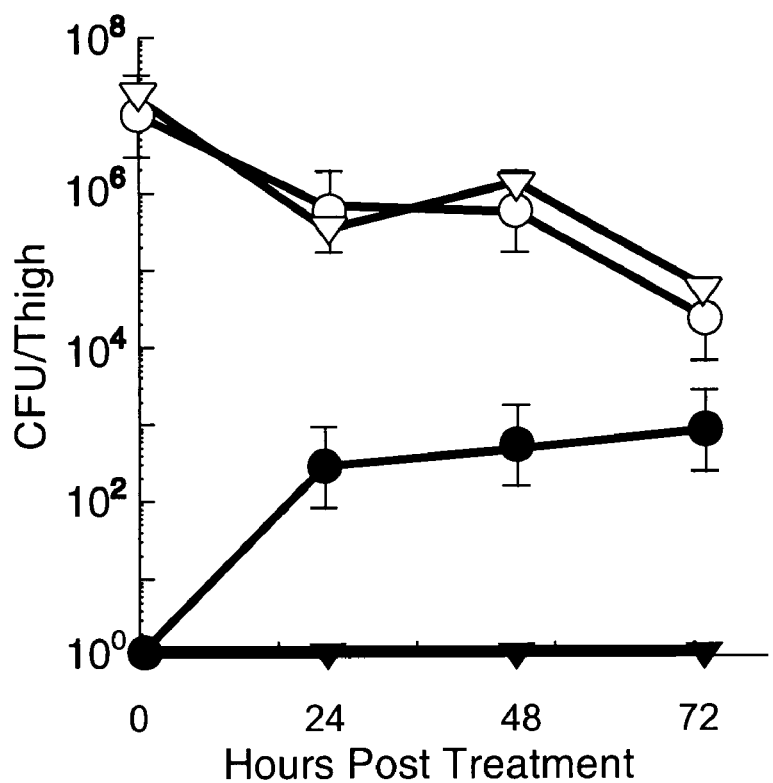
FIG. 12 illustrates mutation and survival of ΔlacZ and lexA(S119A) mutants of *E. coli* ATCC 25922 (injection of about $10^6$ cfu/thigh at 0 hours) in thighs of neutropenic mice at 24-hour intervals after starting therapy with ciprofloxacin injections of ~$10^6$ cfu/thigh at t=0. Open circles and triangles correspond to the total CFU/thigh of the ΔlacZ and lexA (S119A) strains, respectively. Solid circles and triangles represent the number of ciprofloxacin-resistant ΔlacZ and lexA (S119A) mutants/thigh, respectively. The lower limit of detection was 100 organisms per thigh.

In FIG. 12, open circles and triangles correspond to the total colony forming units (CFU)/thigh of the ATCC 25922-ΔlacZ and ATCC 25922 lexA(S119A) strains, respectively. Solid circles and triangles represent the number of ciprofloxacin-resistant ΔlacZ and lexA(S119A) mutants/thigh, respectively. Clearly, in the context of an actual infection, ATCC 25922-lexA(S119A) was unable to evolve resistance to ciprofloxacin, despite the permissive drug concentration in the animal (35 ng/ml ciprofloxacin). Materials and methods for the experiments in this section are detailed in Cirz, R. and Romesberg E. F., submitted.

While the feasibility experiments shown here examined the effect on the emergence of ciprofloxacin resistant E. coli, similar experiments were performed similar experiments looking at the emergence of erythromycin (a macrolide) resistance in E. coli and have observed similar results. Boshoff et al. Cell, (2003) 113, 183-193 have performed similar experiments in which they observe that crippling the ability of RecA to activate LexA self-cleavage prevents Myobacteria from evolving resistance to rifampicin in mouse lung infection models. Collectively, these results strongly suggest that crippling the SOS response severely restricts the ability of multiple bacterial species to induce mutation and thereby evolve resistance to multiple classes of widely-used antibiotics.

Example 5

To examine the role of each individual LexA-repressed polymerases in the induction of resistance-conferring mutations, the ΔpolB, ΔdinB, and ΔumuDC strains were constructed as described above (See Example 4, Table 5). Deletion of polB resulted in a very slight sensitivity to the antibiotic, but deletion of either dinB or umuDC had no detectable effect on antibiotic sensitivity. Consistent with this observation, ΔpolBΔdinB, ΔpolBΔumuDC, and the triple mutant, ΔpolBΔdinBΔumuDC, were slight but reproducibly more sensitive to the antibiotic, while the ΔdinBΔumuDC double mutant exhibited wild-type sensitivity. These data imply that Pol II may play a role in replication restart in response to ciprofloxacin, unlike Pol IV and Pol V, which are not required.

FIGS. 3 and 10 depicts mutation rate of the following ten strains: ΔlacZ [strain 1], ΔpolB [strain 2], ΔdinB [strain 3], ΔumuDC [strain 4], ΔpolB/ΔdinB [strain 5], ΔpolB/ΔumuDC [strain 6], ΔdinB/ΔumuDC [strain 7], ΔpolB/ΔdinB/ΔumuDC [strain 8], lexA(S119A) [strain 9], and ArecD [strain 10]; solid bars represent base substitution mutations and shaded bars represent codon deletion. Values represent number of resistant mutants per surviving cell per day. Error bars represent standard deviation from three independent rate determinations. The above data implies that induced mutation requiring point mutations (such as those involved in ciprofloxacin resistance) will be largely dependent upon Pol V, as opposed to those involving deletion/insertion mutation, which requires Pol IV.

Figure 15:
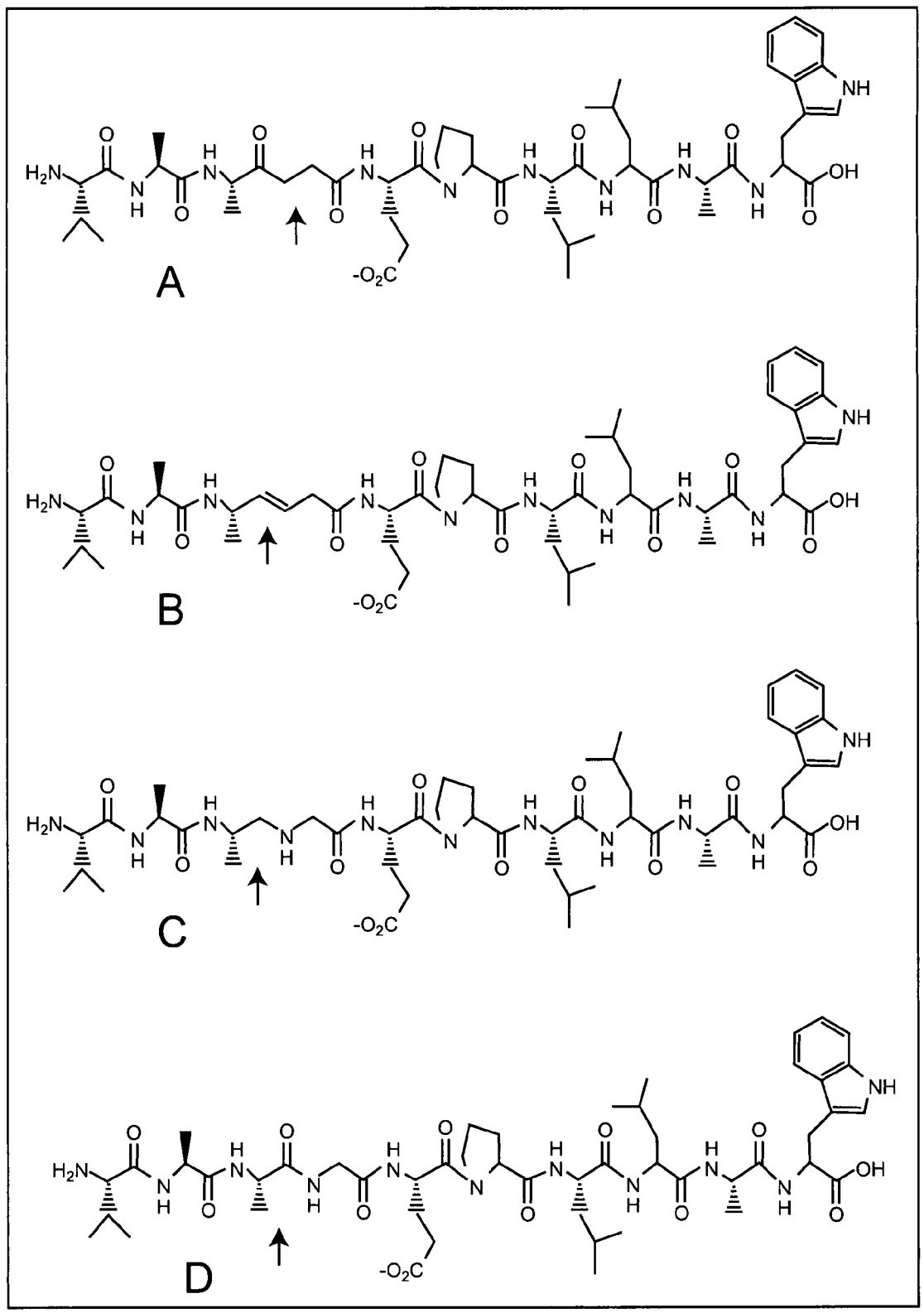
FIGS. 15A-15D illustrate exemplary non-covalent peptidomimetic inhibitors of LexA.

In contrast to the minor changes in sensitivity to ciprofloxacin, as shown in FIGS. 3 and 10, deletion of any one of the three inducible polymerases has a pronounced effect on mutation rate in the presence of the drug. Sequencing revealed that the reduced mutation rates in each deletion strain resulted from the complete absence of substitution mutations (solid portion of bars in FIG. 10). In contrast, the rate of codon deletion remained virtually unchanged (hatched portion of bars in FIG. 10). This implies that the three polymerases are all required for substitution mutation but not for deletion mutation To further examine the role of each polymerase in codon deletion, the double mutants and triple polymerase mutants were examined. As shown in FIG. 15, during days 5 to 8, all deletion strains show low levels of codon deletion. However, by days 9 to 13 each single mutant shows codon deletion rates indistinguishable from wild type cells, while the rates in the double and triple mutants remain low. This implies that codon deletion is mediated by a process involving multiple polymerases that become increasingly less efficient, although not absent, in the single, double, and triple polymerase mutants. As shown in FIG. 15, despite their persistence, these deletion mutants are unlikely to contribute to the evolution of clinically relevant drug resistance, as they remained significantly more sensitive to ciprofloxacin than the substitution derived mutants. This is consistent with the fact that clinically isolated resistant strains always contain substitution mutations. The evolution of clinically significant antibiotic resistance appears to require substitution mutation, and thus all three LexA repressed-polymerases.

Example 6

Two naturally occurring inhibitors of the SOS response (DinI and PsiB) were found which serve as models of such inhibitors.

Two bacterial strains were constructed. One strain harbored a plasmid over producine DinI and another strain harboring a plasmid over producing PsiB. Over production of either protein crippled the ability of these strains to evolve gyrA mutation-mediated resistance to ciprofloxacin (35 ng/ml) by approximately 40-fold. Because clinical ciprofloxacin resistance (15 ug/ml) requires 3-5 independent point mutations, we suspect that an in trans inhibitor of RecA-mediated LexA proteolysis would hinder the emergence of clinical ciprofloxacin resistance by at least 64,000-fold.

Example 7

Two groups of 10 neutropenic Swiss ICR mice were infected in their thigh with either E. coli ATCC 25922-ΔlacZ and ATCC 25922 lexA(S119A) strains. (The LacZ strain had a LacZ knock-out and was replaced with Kan marker as described above; the LexA strain had a LexA gene substituted with LexA S119A as described above)

Two hours after infection the mice received rifampin at 100 mg/kg (subcutaneous) every 12 hours. The mice continued the rifampin regimen until they were sacrificed. Two mice were sacrificed at 0, 24, 48, 72 and 96 hours. The thighs were removed, homogenized, 1:10 serial diluted, and plated for CFU determination. Homogenates were plated on MH agar (NHA) to quantify the entire population of organisms and on rifampin containing MHA plates (16 mg/L) to quantify the population of organisms with a rifampin resistance phenotype. Data from the experiment are presented in Table 7 below.

TABLE 7

| | CFU/Thigh | | | |
| --- | --- | --- | --- | --- |
| | lexA Strain | | lacZ Strain | |
| Time | Media | Media + Rif | Media | Media + Rif |
| 0 | 7.79 ± 0.10 | <2.0 | 7.75 ± 0.09 | <2.0 |
| 24 | 6.95 ± 0.88 | 5.43 ± 1.0 | 6.13 ± 0.47 | 5.88 ± 0.25 |
| 48 | 6.65 ± 0.89 | 5.53 ± 0.70 | 7.33 ± 2.0 | 5.59 ± 0.90 |
| 72 | 7.93 ± 0.96 | 5.79 ± 0.50 | 7.70 ± 1.2 | 7.16 ± 1.28 |
| 96 | 7.07 ± 1.15 | 5.39 ± 1.1 | mice dead. | |

In vitro susceptibility testing of strains was preformed using the NCCLS method. (See National Committee for Clinical Laboratory Standards. 1997. Reference method for broth dilution anti-fungal susceptibility testing of yeasts. Approved standard M27-A. National Committee for Clinical Laboratory Standards, Wayne, Pa.) Eight colonies from each group at the 72 hr time point from MHA plate with and without rifampin were obtained. Minimum inhibitory concentrations ("MICs") were performed in duplicate on three occasions on each colony. Minimum inhibitory concentrations concentration ranges tested were 0.03 to 16,384 mg/L as illustrated in Table 8 below. Minimum inhibitory concentrations of both the LexA and LacZ strains pre-treatment=8.0 mg/L.

TABLE 8

| Minimum Inhibitory Concentrations | | |
| --- | --- | --- |
| Strains | Pre | Post |
| LexA | 8.0 mg/L | 16-32 mg/L |
| LacZ | 8.0 mg/L | >16,384 mg/L |

Example 8

Figure 18:
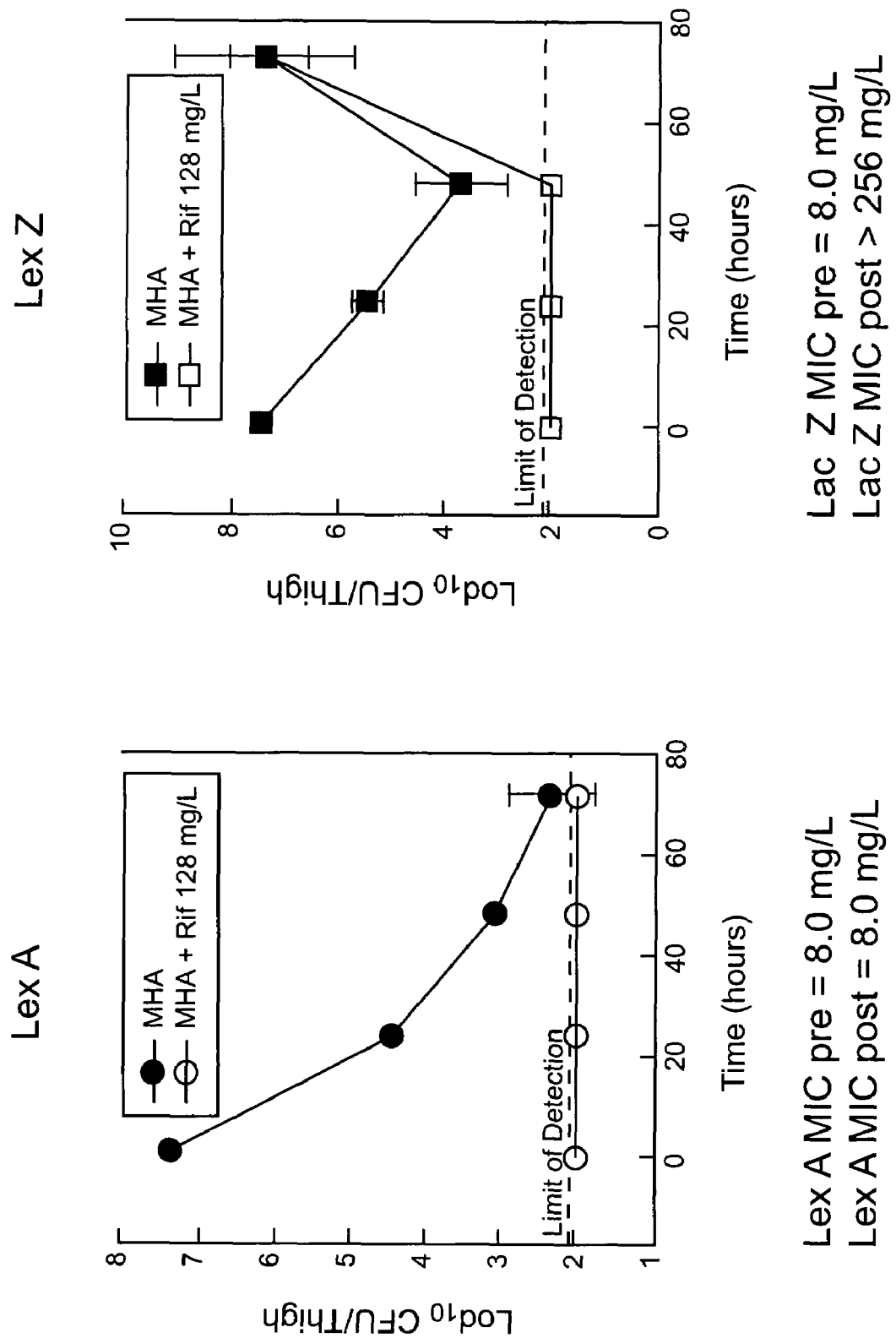
FIG. 18 illustrates results from a rifampin resistance experiment on mouse thighs infected with *E. coli* either ATCC 25922-ΔlacZ or ATCC 25922-lexA(S119A).

In another experiment similar to the one preformed above, thigh high infection was produced in neutropenic CD1 mice with either E. coli ATCC 25922-ΔlacZ and ATCC 25922 lexA(S119A) strains as described above. Two hours after infection mice were treated with rifampin 100 mg/kg twice daily via the subcutaneous route. Groups of two mice were sacrificed at the started of therapy (zero hour) and every 24 h for a period of 72 h. After euthanasia, thigh were removed, homogenized, diluted, and plated for CFU enumeration (lower limit of detection is 2 log cfu/thigh). Homogenate dilutions were plated on MHA with and without rifampin (128 mg/L). Results are illustrated in FIG. 18 and demonstrate that LexA controls the SOS response pathway and that this pathway can be activated by various drugs, not just ciprofloxacin. It also demonstrates that at certain rifampin concentrations (e.g., about 128 mg/L), growth of parent strains (e.g., S119A) would be inhibited.

In vitro susceptibility testing was performed with rifampin on the parent strains and on cells isolated from the agar plates after therapy.

In the animal experiment with ATCC 25922 lexA(S119A), no colonies grew on rifampin containing plates over the 72 h study period. A large number of E. coli ATCC 25922-ΔlacZ colonies grew on rifampin containing plates after 72 h of therapy.

MICs of both parent strains was 8.0 mg/L. MICs of ATCC 25922 lexA(S119A) colonies after therapy remained 8.0 mg/L. MICs of E. coli ATCC 25922-ΔlacZ colonies isolated from the rifampin containing plates were >256 mg/L.

Example 9

RecA protein (12.5 uM, Sigma) was activated by incubation for 30 min on ice in a solution containing 20 mM Tris pH 7.4, 4 mM MgCl2, 2 mM ATPgS, 1 mM DTT and 60 ug/mL 18mer ssDNA (sequence: 5'-TTG TTG TTG TTG TTG TTG-3', SEQ ID NO: 74). A solution of LexA (5 uM) containing 20 mM Tris pH 7.4, 5 mM MgCl2, 1 mM ATPgS, 2 mM DTT and no peptide or the indicated peptide (at 1.2 mM for peptide 1 (SEQ ID NO: 4), 1.8 mM for peptide 2 (SEQ ID NO: 5), 1.5 mM for peptide 3 (SEQ ID NO: 2)) was incubated at 37 degrees for 5 minutes. Cleavage of LexA was initiated by the addition of 0.25 uM activated RecA. The mixture was incubated at 37 degrees for 30 min. Aliquots were removed and quenched in aqueous acetonitrile containing 0.1% TFA.

Figure 20:
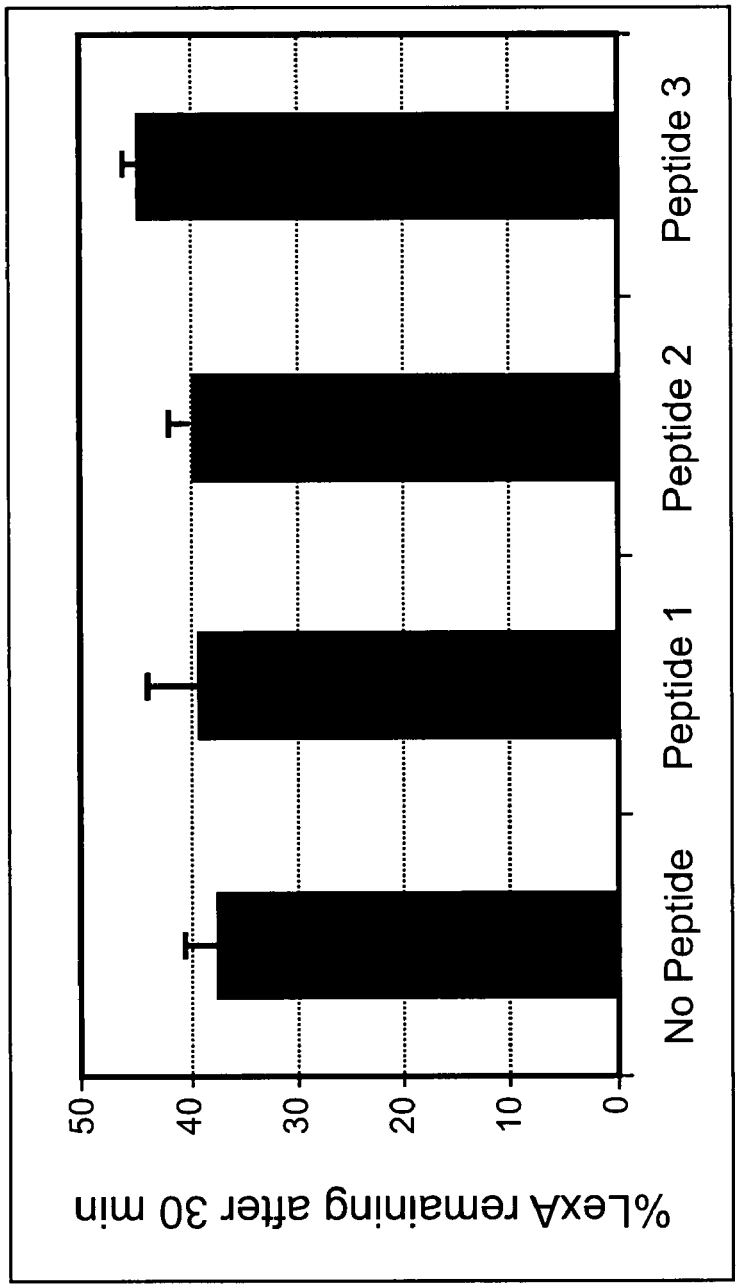
FIG. 20 illustrates inhibition of LexA's autocleavage by three peptides (peptide 1,SEQ ID NO: 4; peptide 2, SEQ ID NO: 5; and peptide 3 , SEQ ID NO: 2).
Figure 21:
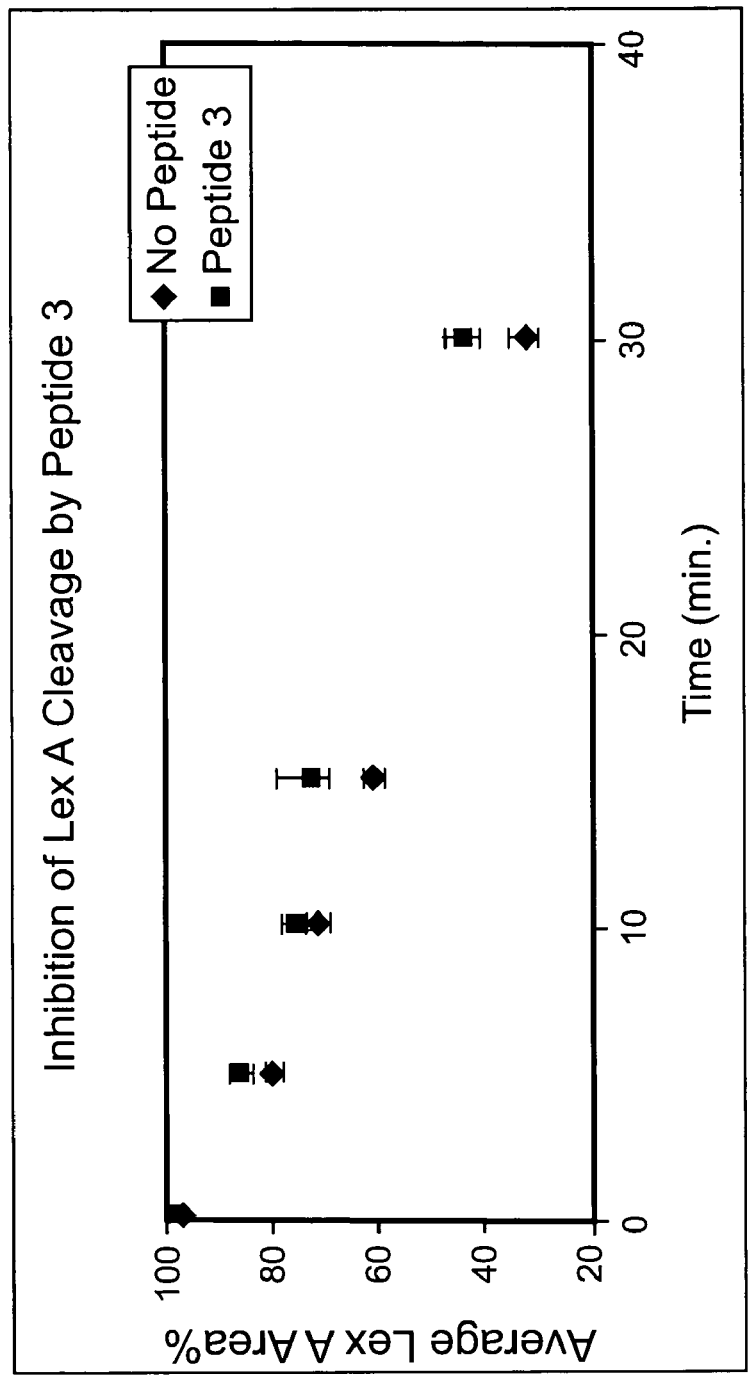
FIG. 21 illustrates a comparison of inhibition of LexA's autocleavage by peptide 3 and without peptide 3.

The cleavage of LexA protein was monitored by HPLC using a gradient of 30 to 90% buffer B (9.9% H$_2$O, 90% CH3CN, 0.1% TFA) in buffer A(98% H$_2$O, 1.9% CH3CN, 0.1% TFA) and recording absorbance at 214 nm. Results are illustrated in FIG. 20. Error bars represent one standard deviation of three separate experiments. FIG. 21 illustrates a comparison of LexA autocleavage inhibition by peptide 3 over a 30 minute period of time.

Example 10

Despite stringent hygiene practices, hospitals and eldercare facilities remain two of the major breeding grounds for antibiotic resistant bacteria, as well as ideal environments for their transmission. MRSA (Methicillin-resistant *Staphylococcus aureus*), VRE (Vancomycin-resistant *Enterococcus*), and MDR (multi-drug resistant) pneumonia are only a few of a spectrum of "hospital infections" that could be curbed with the aid of a resistance-suppressing agent.

It is quite common for already drug resistant bacterial strains (e.g., MRSA or VRE) to infect patients who initially come to a hospital free of infection. The present invention contemplates the use of an achaogen to kill dangerous multi-drug-resistant strains such as MRSA and VRE.

In particular, rifampin has fallen out of common clinical use, because rifampin resistance emerges within 24 hours from the initiation of treatment. See Example 10 above. Because the mutations that confer rifampin resistance impose a significant growth disadvantage on bacteria, resistant bacterial populations promptly revert to rifampin sensitivity within a few weeks of cessation of treatment. As such, nearly all MRSA and VRE strains encountered in hospitals are initially rifampin sensitive. The present invention contemplates the use of an achaogen in combination with rifampin to kill dangerous gram-positive organisms resistant to one or more other antibiotics, but, initially sensitive to rifampin. Preferably, an achaogen and rifampin are co-formulated to create an 'evergreen' drug to which resistance could not be maintained.

Example 11

Bacteria can be classified as gram-positive or gram-negative by the following Gram test steps. Bacterial cells are dried onto a glass slide and stained with crystal violet, then washed briefly in water. Iodine solution is added so that the iodine forms a complex with crystal violet in the cells. Alcohol or acetone is added to solubilise the crystal violet—iodine complex. The cells are counterstained with safranin, then rinsed and dried for microscopy. Gram-positive bacteria retain the crystal violet-iodine complex and thus appear purple (shown for *Bacillus cereus* in the left-hand image below). Gram-negative bacteria are decolourised by the alcohol or acetone treatment, but are then stained with safranin so they appear pink (shown for *Pseudomonas aeruginosa* in the right-hand image below). Thus, the essential difference between Gram-positive and Gram-negative cells is their ability to retain the crystal violet-iodine complex when treated with a solvent.

Examples of gram-negative bacilli include *E. coli*, (causes UTI and other infections) *Enterobacter* (causes UTI and other infections), *Pseudomonas aueruginosa* (UTI, pneumonia and bacteremia), *Salmonella* (causes typhoid fever, paratyphoid fever, bacteremia, and acute gastroenteritis), *Shigella* (acute gastroenteritis), *Campylobacter* (causes enteritis, bacteremia, endocarditis, and meningitis), *Vibrio cholerae* (causes cholera).

Examples of gram-positive include *B. anthracis* which causes anthrax and pneumonia Examples of gram negative cocci include *Neisseria*, which causes gonorrhea and meningitis.

Examples of gram positive cocci include *Staphylococci*, which causes abscesses, bacteremia, endocarditis, pneumonia, osteomyelitis, an dcellulitis.

All publications and patent applications mentioned in this specification are herein incorporated by reference to the same extent as if each individual publication or patent application was specifically and individually indicated to be incorporated by reference.

It will be apparent to one of ordinary skill in the art that many changes and modifications can be made thereto without departing from the spirit or scope of the appended claims.

All publications and patent applications mentioned in this specification are herein incorporated by reference to the same extent as if each individual publication or patent application was specifically and individually indicated to be incorporated by reference. It will be apparent to one of ordinary skill in the art that many changes and modifications can be made thereto without departing from the spirit or scope of the appended claims.

What is claimed is:

1. A method of inhibiting the evolution of resistance to a quinolone antibiotic in a bacteria comprising administering to the bacteria a quinolone and a composition comprising an agent that inhibits LexA, thereby inhibiting an SOS response pathway in the bacteria.

2. A method of inhibiting the evolution of resistance to a quinolone antibiotic in a bacteria comprising administering to the bacteria a quinolone and a composition comprising an agent that inhibits RecA or LexA, thereby inhibiting an SOS response pathway in the bacteria, wherein said agent comprises a peptide comprising a LexA cleavage sequence.

3. The method of claim 2, wherein said peptide comprises a dipeptide Ala-Ala or a tripeptide Val-Ala-Ala.

4. A method of inhibiting the evolution of resistance to a quinolone antibiotic in a bacteria comprising administering to the bacteria a quinolone and a composition comprising an agent that inhibits RecA or LexA, thereby inhibiting an SOS response pathway in the bacteria, wherein said agent is an isolated and purified PsiB, DinI or a variant or fragment thereof.

5. A method of inhibiting the evolution of resistance to a quinolone antibiotic in a bacteria comprising administering to the bacteria a quinolone and a composition comprising an agent that inhibits RecA or LexA, thereby inhibiting an SOS response pathway in the bacteria, wherein said agent is an antibody or antibody fragment that specifically binds to RecA or LexA.

* * * * *